(12) United States Patent  
Benson et al.

(10) Patent No.: US 7,807,471 B2
(45) Date of Patent: Oct. 5, 2010

(54) IL-23P40 SPECIFIC IMMUNOGLOBULIN DERIVED PROTEINS, COMPOSITIONS, EPITOPES, METHODS AND USES

(75) Inventors: Jacqueline Benson, Malvern, PA (US); Mark Cunningham, Kennett Square, PA (US); Jeffrey (Sinquan) Luo, Malvern, PA (US)

(73) Assignee: Centocor Ortho Biotech, Inc., Malvern, PA (US)

( * ) Notice: Subject to any disclaimer, the term of this patent is extended or adjusted under 35 U.S.C. 154(b) by 220 days.

(21) Appl. No.: 11/768,582

(22) Filed: Jun. 26, 2007

(65) Prior Publication Data

US 2008/0038831 A1 Feb. 14, 2008

Related U.S. Application Data

(62) Division of application No. 11/234,011, filed on Sep. 23, 2005, now Pat. No. 7,252,971.

(60) Provisional application No. 60/612,866, filed on Sep. 24, 2004, provisional application No. 60/616,832, filed on Oct. 7, 2004.

(51) Int. Cl.
  *G01N 33/00* (2006.01)
  *G01N 33/50* (2006.01)
  *C12P 21/06* (2006.01)
  *C12P 21/00* (2006.01)
(52) U.S. Cl. ......................................... 436/86; 435/69.1
(58) Field of Classification Search .................. None
  See application file for complete search history.

(56) References Cited

U.S. PATENT DOCUMENTS

| | | | |
|---|---|---|---|
| 5,350,836 A * | 9/1994 | Kopchick et al. | ........... 530/399 |
| 6,060,284 A | 5/2000 | Bazan | |
| 6,479,634 B1 | 11/2002 | Bazan | |
| 6,495,667 B1 | 12/2002 | Bazan | |
| 6,610,285 B1 | 8/2003 | Hirata | |
| 6,756,481 B2 | 6/2004 | Chirica et al. | |
| 6,800,460 B1 | 10/2004 | Oppmann et al. | |
| 6,835,825 B1 | 12/2004 | Bazan | |
| 2003/0162261 A1 | 8/2003 | Oppmann et al. | |

(Continued)

FOREIGN PATENT DOCUMENTS

WO  WO 99/05280 A1  2/1999

(Continued)

OTHER PUBLICATIONS

Peter J. Barnes, "Cytokine-directed therapies for the treatment of chronic airway diseases," Cytokine & Growth Factor Reviews 14 (2003): 511-522 (2003).

(Continued)

*Primary Examiner*—Cherie M Woodward
(74) *Attorney, Agent, or Firm*—Eric Dichter

(57) ABSTRACT

An anti-IL-23 specific human Ig derived protein, isolated nucleic acids that encode at least one anti-IL-23 Ig derived protein, vectors, host cells, transgenic animals or plants, and methods of making and using thereof are useful as therapeutic and diagnostic compositions, methods and devices. The anti-IL-23 Ig derived protein preferably binds to one or more of the Seg 1, Seg 2, and Seg 3 epitopes of the p40 subunit of IL-23.

10 Claims, 11 Drawing Sheets

U.S. PATENT DOCUMENTS

| | | |
|---|---|---|
| 2004/0223969 A1 | 11/2004 | Oft et al. |
| 2004/0258686 A1 | 12/2004 | Chirica et al. |
| 2005/0244874 A1 | 11/2005 | Kastelein et al. |

FOREIGN PATENT DOCUMENTS

| | | |
|---|---|---|
| WO | WO 99/40195 A1 | 8/1999 |
| WO | WO 00/09552 A1 | 2/2000 |
| WO | WO 00/53631 A1 | 9/2000 |
| WO | WO 00/70049 A2 | 11/2000 |
| WO | WO 01/18051 A2 | 3/2001 |
| WO | WO 01/85790 A2 | 11/2001 |
| WO | WO 2004/042009 A2 | 5/2004 |
| WO | WO 2004/058178 A2 | 7/2004 |
| WO | WO 2004/071517 A2 | 8/2004 |
| WO | WO 2004/081190 A2 | 9/2004 |

OTHER PUBLICATIONS

Trinchieri, et al., "The IL-12 Family of Heterodimeric Cytokines: New Players in the Regulation of T Cell Responses," Immunity, 19: 641-644 (2003).

Maguire van Seventer, et al., "Interferon-β differentially regulates expression of the IL-12 family members p35, p40, p19 and EB13 in activated human dendritic cells," Journal of Neuroimmunology, 133: 60-71 (2002).

Yadav, et al., "Cytokines and autoimmunity: redundancy defines their complex nature," Current Opinion in Immunology, 15: 697-703 (2003).

Murphy, et al., "Divergent Pro- and Antiinflammatory Roles for IL-23 and IL-12 in Joint Autoimmune Inflammation," Journal of Experimental Medicine, 198(12): 1951-1957 (2003).

David M. Frucht, "IL-23: A Cytokine That Acts on Memory T Cells," Science STKE, 114: 1-3 (2002).

Wiekowski, et al., "Ubiquitous Transgenic Expression of the IL-23 Subunit p19 Induces Multiorgan Inflammation, Runting, Infertility, and Premature Death," Journal of Immunology, 166: 7563-7570 (2001).

Belladonna, et al., "IL-23 and IL-12 Have Overlapping, but Distinct, Effects on Murine Dendritic Cells," The Journal of Immunology, 168: 5448-5454 (2002).

Parham, et al., "A Receptor for the Heterodimeric Cytokine IL-23 is Composed of IL-12Rβ1 and a Novel Cytokine Receptor Subunit, IL-23R," The Journal of Immunology, 168: 5699-5708 (2002).

Oppmann, et al., "Novel p19 Protein Engages IL-12p40 to Form a Cytokine, IL-23, with Biological Activities Similar as Well as Distinct from IL-12," Immunity, 13: 715-725 (2000).

Cua, et al., "Interleukin-23 rather than interleukin-12 is the critical cytokine for autoimmune inflammation of the brain," Nature, 421: 744-748 (2003).

D'Andrea, et al., "Production of Natural Killer Cell Stimulatory Factor (Interleukin 12) by Peripheral Blood Mononuclear Cells," Journal of Experimental Medicine, 176: 1387-1398 (1992).

GenBank Accession No. AF301620, Oppmann, et al., Dec. 4, 2000.
GenBank Accession No. AA418955, Hillier, et al., May 12, 1997.
GenBank Accession No. C06368, J. Takeda, Aug. 9, 1996.
GenBank Accession No. AA418747, Hillier, et al., May 12, 1997.
PCT International Search Report dated Oct. 26, 2006.

\* cited by examiner

FIGURE 6
Anti-IL-23 during established EAE:
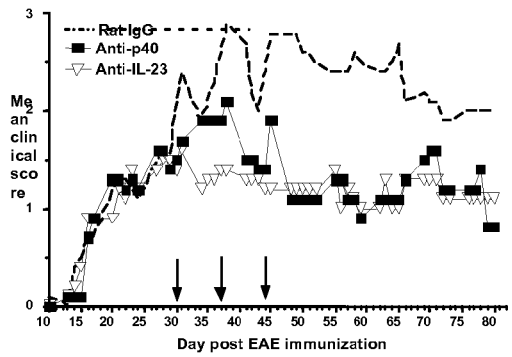
FIG. 6A
Anti-p40 vs Anti-IL-12 during L.major infection:
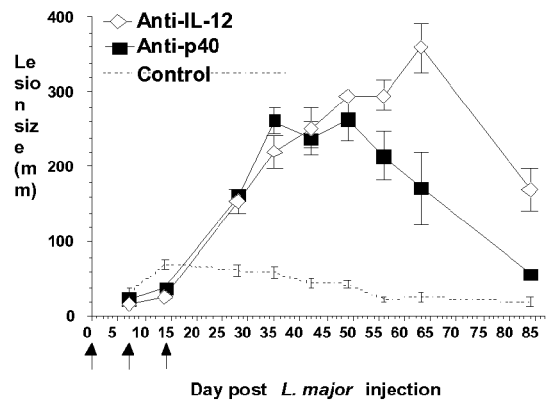
FIG. 6B
Anti-IL-23 during L.major infection:
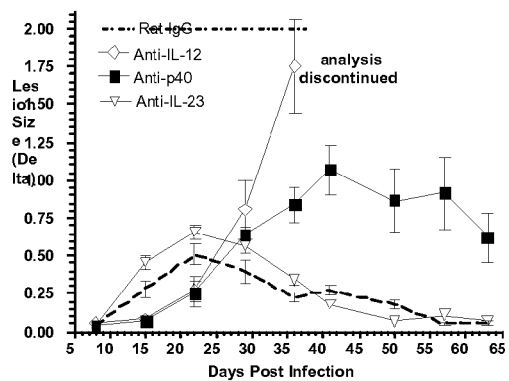
FIG. 6C

US 7,807,471 B2

IL-23P40 SPECIFIC IMMUNOGLOBULIN DERIVED PROTEINS, COMPOSITIONS, EPITOPES, METHODS AND USES

CROSS-REFERENCE TO RELATED APPLICATIONS

This application is a divisional application of U.S. Ser. No. 11/234,011, filed 23 Sep. 2005 now U.S. Pat. No. 7,252,971, which claims the benefit of priority to U.S. Provisional Application Ser. No. 60/612,866, filed Sep. 24, 2004, and U.S. Provisional Application Ser. No. 60/616,832, filed Oct. 7, 2004. The entire contents of each of the foregoing applications are incorporated herein by reference in their entirety.

FIELD OF THE INVENTION

The present invention relates to at least one IL-23p40 specific human Ig derived protein or fragment thereof, encoding and complementary nucleic acids, host cells, IL-23p40 specific epitopes, and methods of making and using thereof, including therapeutic formulations, administration and devices.

BACKGROUND OF THE INVENTION

Interleukin-23 (IL-23) is the name given to a factor that is composed of the p40 subunit of IL-12 (IL-12beta, IL-12-p40) and another protein of 19 kDa, designated p19. The p19 subunit is structurally related to IL-6, G-CSF, and the p35 subunit of IL-12. The p19 subunit by itself is biologically inactive while the complex of p19 with p40 is active. The active complex is secreted by antigen presenting cells after cell activation. Mouse memory T-cells (CD4 (+)CD45 Rb(low)) proliferate in response to IL-23 but not in response to IL-12. Human monocyte-derived macrophages produce IL-23 in response to virus infection (Sendai virus, but not Influenza A virus).

The IL-23 receptor complex consists of a receptor chain, termed IL23R, and the beta-1 subunit of the IL-12 receptor. IL-23 does not bind to the beta-2 subunit of the IL-12 receptor. The human IL-23R gene is on human chromosome 1 within 150 kb of the gene encoding IL-12Rbeta2. IL-23 activates the same signaling molecules as IL-12: JAK2, Tyk2, and STAT-1, STAT-3, STAT-4, and STAT-5. STAT-4 activation is substantially weaker and different DNA-binding STAT complexes form in response to IL-23 as compared to IL-12. IL-23R associates constitutively with JAK2 and in a ligand-dependent manner with STAT-3.

Expression of p19 in transgenic mice leads to runting, systemic inflammation, infertility, and death before 3 months of age. The animals show high serum concentrations of the pro-inflammatory cytokines TNF-alpha and IL-1. The number of circulating neutrophils is increased. Acute phase proteins are expressed constitutively. Animals expressing p 19 specifically in the liver do not show these abnormalities. Expression of p19 is most likely due to hematopoietic cells as bone marrow transplantation of cells expressing p19 causes the same phenotype as that observed in the transgenic animals.

Biologically active IL-12 exists as a heterodimer comprised of 2 covalently linked subunits of 35 (p35) and 40 (p40) kD. IL-12 acts by binding to both the IL-12beta 1 and beta 2 receptor proteins and thereby induces signaling in a cell presenting both of these receptors. Several lines of evidence have demonstrated that IL-12 can induce robust Th1 immune responses that are characterized by production of IFNγ and IL-2 from CD4$^+$ T cells. Inappropriate Th1 responses, and thus IL-12 expression, are believed to correlate with many autoimmune diseases, such as multiple sclerosis, rheumatoid arthritis, inflammatory bowel disease, insulin-dependent diabetes mellitus, and uveitis. In animal models, IL-12 neutralization was shown to ameliorate autoimmune disease. However, these studies neutralized both IL-12 and IL-23 through the shared p40 subunit.

IL-12 is thought to be important in the development of Th1, or "type 1," CD4+ T cell responses, whereas IL-23 is thought to be important for the activation of memory CD4+ T cells. Several studies suggest that IL-12 is responsible for generating effective immune responses to intracellular pathogens and tumor cells, while the function of IL-23 in these types of immune responses has yet to be fully described. Therefore, while inhibition of both IL-12 and IL-23 should provide significant therapy for immune-mediated disease, inhibition of IL-12 pathways could limit immunity to pathogens or tumor cells and result in an unwanted risk profile. In contrast, inhibition of only IL-23 could provide therapeutic benefit while leaving IL-12 pathways intact. Thus, effective therapy would be achieved concomitant with a lowered risk profile.

Non-human, chimeric, polyclonal (e.g., anti-sera) and/or monoclonal antibodies (Mabs) and fragments (e.g., proteolytic digestion products thereof) are potential therapeutic agents that are being developed in some cases to attempt to treat certain diseases. However, such antibodies that comprise non-human portions elicit an immune response when administered to humans. Such an immune response can result in an immune complex-mediated clearance of the antibodies from the circulation, and make repeated administration unsuitable for therapy, thereby reducing the therapeutic benefit to the patient and limiting the readministration of the Ig derived protein. For example, repeated administration of antibodies comprising non-human portions can lead to serum sickness and/or anaphalaxis. In order to avoid these and other such problems, a number of approaches have been taken to reduce the immunogenicity of such antibodies and portions thereof, including chimerization and "humanization," as well known in the art. These approaches have produced antibodies having reduced immunogenicity, but with other less desirable properties.

Accordingly, there is a need to provide anti-IL-23 antibodies or specified portions or variants, nucleic acids, host cells, compositions, and methods of making and using thereof, that overcome one more of these problems.

SUMMARY OF THE INVENTION

The present invention provides immunoglobulin (Ig) derived proteins that are specific for the p40 subunit of IL-23, ("anti-IL-23 Ig derived protein" or "IL-23 Ig derived protein"). Preferably, the IL-23 Ig proteins do not bind to the p40 subunit of IL-12, and/or inhibit binding of IL-12 to one or more of its receptors. Such Ig derived proteins, including antibodies, antagonists or receptor fusion proteins block the binding of IL-23 to at least one of its receptors by binding to the p40 subunit of IL-23. For example, they bind to human IL-23p40 and block binding of human IL-23 to at least one of its receptors. The present invention further provides compositions, formulations, methods, devices and uses of such anti-IL-23 Ig derived proteins, including for therapeutic and diagnostic uses.

In one embodiment, the present invention provides the predicted epitope regions for the human and murine IL-23p40 subunits. These epitopes are predicted to be available for binding on the IL-23p40 subunit (of the IL-23 dual subunit protein) and unavailable on the IL-12p40 subunit (alone or of the IL-12 dual subunit protein).

In a further embodiment, the present invention provides Ig derived proteins that selectively inhibit IL-23 related activities and, further do not inhibit IL-12 specific activities that are mediated by the binding of IL-12 to one or more of its receptors.

In another embodiment, the present invention provides Ig derived proteins that inhibit IL-23 activity in antigen presenting cells (APCs), such as but not limited to, macrophages, microglia, mesangial phagocytes, synovial A cells, stem cell precursors, Langerhans cells, Kuppfer cells, dendritic cells, B cells, and the like. Such APCs can be present in different tissues, e.g., but not limited to, skin, epidermis, liver, spleen, brain, spinal cord, thymus, bone marrow, joint synovial fluid, kidneys, blood, and the like. Such APCs can also be limited to outside or inside the blood brain barrier.

In a further embodiment, the present invention provides Ig derived proteins that are suitable for treating at least one IL-23 related condition by blocking IL-23 binding to one or more of its receptors, and, optionally, where the Ig derived proteins do not block IL-12 binding to one or more of its receptors such that no independent IL-12 function is impaired.

The present invention thus provides isolated human, primate, rodent, mammalian, chimeric, humanized and/or CDR-grafted anti-IL-23 Ig derived proteins (Ig derived proteins), including antibodies, immunoglobulins, receptor fusion proteins, cleavage products and other specified portions and variants thereof, as well as anti-IL-23 Ig derived protein compositions, encoding or complementary nucleic acids, vectors, host cells, compositions, formulations, devices, transgenic animals, transgenic plants, and methods of making and using thereof, as described and enabled herein, in combination with what is known in the art. Such anti-IL-23 Ig derived proteins act as antagonists to IL-23 proteins and/or IL-23 receptors and thus are useful for treating IL-23 pathologies. IL-23 proteins include, but are not limited to, IL-23, particularly, the p40 subunit of IL-23, as well as the p19 subunit of IL-23.

The present invention provides, in one aspect, isolated nucleic acid molecules comprising, complementary, or hybridizing to, a polynucleotide encoding specific IL-23 Ig derived proteins or specified portions or variants thereof, comprising at least one specified sequence, domain, portion or variant thereof. The present invention further provides recombinant vectors comprising said isolated IL-23 Ig derived protein nucleic acid molecules, host cells containing such nucleic acids and/or recombinant vectors, as well as methods of making and/or using such Ig derived protein nucleic acids, vectors and/or host cells.

At least one Ig derived protein or specified portion or variant of the invention binds at least one specified epitope specific to at least one IL-23 protein, receptor, subunit, fragment, portion or any combination thereof. The at least one epitope can comprise at least one Ig derived protein binding region that comprises at least one portion of the mature or the extracellular region of said protein and/or receptor. Non-limiting examples include 1, 2, 3, 4, 5, 6, 7, 8, 9, 10, 11, 12, 13 or 14 amino acids of at least one of, 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, 290-300, 300-306, 1-7, 14-21, 29-52, 56-73, 83-93, 96-105, 156-175, 194-204, 208-246, 254-273, 279-281, or 289-300 of SEQ ID NO: 1 as the human p40 subunit (306 amino acids). Preferred examples include 1, 2, 3, 4, 5, 6, 7, 8, 9 or 10 amino acids of the mature peptide or extracellular domain of human IL-23p40 (SEQ ID NO: 1). More specifically, the epitope regions are predicted to comprise all or a portion of Seg 1 (amino acids 97-101 of SEQ ID NO: 1), and/or Seg 2 (amino acids 138-145 of SEQ ID NO:1), and/or Seg 3 (amino acids 250-269 of SEQ ID NO:1) of SEQ ID NO:1. The murine counterparts (on the murine p40 subunit) for these epitope regions are Murineseg 1 (amino acids 97-98 of the murine sequence shown in Table 5 below without the signal sequence or amino acids 119-120 of the sequence containing the 22-amino acid signal sequence), Murineseg 2 (amino acids 135-142 of the murine sequence shown in Table 5 below without the signal sequence or amino acids 157-164 of the sequence containing the 22-amino acid signal sequence), Murineseg 3 (amino acids 247-274 of the murine sequence shown in Table 5 below without the signal sequence or amino acids 269-296 of the sequence containing the 22-amino acid signal sequence). The at least one Ig derived protein or specified portion or variant amino acid sequence can further optionally comprise at least one specified substitution, insertion or deletion.

The present invention also provides at least one composition comprising (a) an isolated IL-23 Ig derived protein or specified portion or variant encoding nucleic acid and/or Ig derived protein as described herein; and (b) a suitable carrier or diluent. The carrier or diluent can optionally be pharmaceutically acceptable, according to known methods. The composition can optionally further comprise at least one other compound, protein or composition.

The present invention also provides at least one method for expressing at least one IL-23 Ig derived protein or specified portion or variant in a host cell, comprising culturing a host cell as described herein and/or as known in the art under conditions wherein at least one IL-23 Ig derived protein or specified portion or variant is expressed in detectable and/or recoverable amounts.

The present invention further provides at least one IL-23 Ig derived protein, specified portion or variant in a method or composition, when administered in a therapeutically effective amount, for modulation, for treating or reducing the symptoms of immune, neurological, and related disorders, such as, but not limited to, multiple sclerosis, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to, asthenia, anemia, cachexia, and the like), chronic salicylate intoxication, acute or chronic bacterial infection, acute and chronic parasitic or infectious processes, including bacterial, viral and fungal infections, HIV infection/HIV neuropathy, meningitis, hepatitis (e.g., A, B or C, or the like), septic arthritis, peritonitis, pneumonia, epiglottitis, *e. Coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitis/epidydimitis, *legionella*, lyme disease, influenza a, epstein-barr virus, vital-associated hemaphagocytic syndrome, vital encephalitis/aseptic meningitis, neurodegenerative diseases, multiple sclerosis, migraine headache, AIDS dementia complex, demyelinating diseases, such as multiple sclerosis and acute transverse myelitis; extrapyramidal and cerebellar disorders, such as lesions of the corticospinal system; disorders of the basal ganglia; hyperkinetic movement disorders, such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi.system disorder); demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, neurotraumatic injury (e.g., but not limited to, spinal cord injury, brain injury, concussion, and repetitive concussion), pain, inflammatory pain, autism, depression, stroke, cognitive disorders, epilepsy, and the like, as needed in many different conditions, such as but not limited to, prior to, subsequent to, or during a related disease or treatment condition, as known in the art.

The present invention further provides at least one IL-23 Ig derived protein, specified portion or variant in a method or composition, when administered in a therapeutically effective amount, for modulation, for treating or reducing the symptoms of at least one IL-23 disease in a cell, tissue, organ, animal or patient and/or, as needed in many different conditions, such as but not limited to, prior to, subsequent to, or during a related disease or treatment condition, as known in the art and/or as described herein.

The present invention also provides at least one composition, device and/or method of delivery of a therapeutically or prophylactically effective amount of at least one IL-23 Ig derived protein or specified portion or variant, according to the present invention.

The present invention also provides at least one isolated IL-23 Ig derived protein, comprising at least one immunoglobulin complementarity determining region (CDR) or at least one ligand binding region (LBR) that specifically binds at least one IL-23 protein or receptor, wherein said IL-23 Ig derived protein specifically binds at least one epitope not available on the IL-12p40 subunit comprising at least 1-3 amino acids of the entire amino acid sequence (amino acids 1-306) of the IL-23p40 subunit (SEQ ID NO:1), such as but not limited to, 1, 2, 3, 4, 5, 6, 7, 8, 9, 10, 11, 12, 13 or 14 amino acids of at least one of, 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 280-290, 290-300, 300-306, 1-7, 14-21, 29-52, 56-73, 83-93, 96-105, 156-175, 194-204, 208-246, 254-273, 279-281, or 289-300 of SEQ ID NO:1. Preferred examples include 1, 2, 3, 4, 5, 6, 7, 8, 9 or 10 amino acids of the mature peptide or extracellular domain of human IL-23p40 (SEQ ID NO:1), comprised of SEQ ID NO:1, more specifically, the epitope regions are predicted to comprise Seg 1 (amino acids 97-101 of SEQ ID NO:1), and/or Seg 2 (amino acids 138-145 of SEQ ID NO:1), and/or Seg 3 (amino acids 250-269 of SEQ ID NO:1) of SEQ ID NO:1.

The invention also provides at least one isolated IL-23 human Ig derived protein encoding nucleic acid, comprising a nucleic acid that hybridizes under stringent conditions, or has at least 95% identity, to a nucleic acid encoding an IL-23 Ig derived protein. The invention further provides an isolated IL-23 human Ig derived protein, comprising an isolated human Ig derived protein encoded by such a nucleic acid. The invention further provides an IL-23 human Ig derived protein encoding nucleic acid composition, comprising such an isolated nucleic acid and a carrier or diluent. The invention further provides an Ig derived protein vector, comprising such a nucleic acid, wherein the vector optionally further comprises at least one promoter selected from the group consisting of a late or early SV40 promoter, a CMV promoter, an HSV tk promoter, a pgk (phosphoglycerate kinase) promoter, a human immunoglobulin promoter, and an EF-1 alpha promoter. Such a vector can optionally further comprise at least one selection gene or portion thereof selected from at least one of methotrexate (MTX), dihydrofolate reductase (DHFR), green fluorescent protein (GFP), neomycin (G418), or glutamine synthetase (GS). The invention further comprises a mammalian host cell comprising such an isolated nucleic acid, optionally, wherein said host cell is at least one selected from COS-1, COS-7, HEK293, BHK21, CHO, BSC-1, Hep G2, 653, SP2/0, 293, HeLa, myeloma, or lymphoma cells, or any derivative, immortalized or transformed cell thereof.

The invention also provides at least one method for producing at least one IL-23 human Ig derived protein, comprising translating such a nucleic acid or an endogenous nucleic acid that hybridizes thereto under stringent conditions, under conditions in vitro, in vivo or in situ, such that the IL-23 human Ig derived protein is expressed in detectable or recoverable amounts.

The invention also provides at least one IL-23 human Ig derived protein composition, comprising at least one isolated IL-23 human Ig derived protein and a carrier or diluent, optionally, further wherein said carrier or diluent is pharmaceutically acceptable, and/or further comprising at least one compound or protein selected from at least one of a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an IL-23 agent, a mineral, a nutritional, a thyroid agent, a vitamin, a calcium related hormone, an antidiarrheal, an antitussive, an antiemetic, an antiulcer, a laxative, an anticoagulant, an erythropieitin, a filgrastim, a sargramostim, an immunization, an immunoglobulin, an immunosuppressive, a growth hormone, a hormone replacement drug, an estrogen receptor modulator, a mydriatic, a cycloplegic, an alkylating agent, an antimetabolite, a mitotic inhibitor, a radiopharmaceutical, an antidepressant, an antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha, a cytokine, and a cytokine antagonist.

The present invention also provides at least one method for treating an IL-23 condition in a cell, tissue, organ or animal, comprising contacting or administering a immune related- or infectious related-condition modulating effective amount of at least one IL-23 human Ig derived protein with, or to, said cell, tissue, organ or animal, optionally, wherein said animal is a primate, optionally a monkey or a human. The method can further optionally include wherein said effective amount is about 0.001-100 mg/kilogram of said cells, tissue, organ or animal. Such a method can further include wherein said contacting or said administrating is by at least one mode selected from intravenous, intramuscular, bolus, intraperitoneal, subcutaneous, respiratory, inhalation, nasal, vaginal, rectal, buccal, sublingual, intranasal, subdermal, and transdermal. Such a method can further comprise administering, prior, concurrently or after said contacting or administering, at least one composition comprising a therapeutically effective amount of at least one compound or protein selected from at least one of a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an IL-23 agent, a mineral, a nutritional, a thyroid agent, a vitamin, a calcium related hormone, an antidiarrheal, an antitussive, an antiemetic, an antiulcer, a laxative, an anticoagulant, an erythropoietin, a filgrastim, a sargramostim, an immunization, an immunoglobulin, an immunosuppressive, a growth hormone, a hormone replacement drug, an estrogen receptor modulator, a mydriatic, a cycloplegic, an alkylating agent, an antimetabolite, a mitotic inhibitor, a radiopharmaceutical, an antidepressant, an antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha, a cytokine, and a cytokine antagonist.

The present invention also provides at least one medical device, comprising at least one IL-23 human Ig derived protein, wherein said device is suitable for contacting or administering said at least one IL-23 human Ig derived protein by at least one mode selected from intravenous, intramuscular, bolus, intraperitoneal, subcutaneous, respiratory, inhalation, nasal, vaginal, rectal, buccal, sublingual, intranasal, sub dermal, and trans dermal.

The present invention also provides at least one human immunoglobulin light chain IL-23 protein, comprising at least one portion of a variable region comprising at least one human Ig derived protein fragment of the invention.

The present invention also provides at least one human immunoglobulin heavy chain or portion thereof, comprising at least one portion of a variable region comprising at least one IL-23 human Ig derived protein fragment.

The invention also includes at least one human Ig derived protein, wherein said human Ig derived protein binds the same epitope or antigenic region as an IL-23 human Ig derived protein.

The invention also includes at least one formulation comprising at least one IL-23 human Ig derived protein, and at least one selected from sterile water, sterile buffered water, or at least one preservative selected from the group consisting of phenol, m-cresol, p-cresol, o-cresol, chlorocresol, benzyl alcohol, alkylparaben, benzalkonium chloride, benzethonium chloride, sodium dehydroacetate and thimerosal, or mixtures thereof in an aqueous diluent, optionally, wherein the concentration of IL-23 human Ig derived protein is about 0.1 mg/ml to about 100 mg/ml, further comprising at least one isotonicity agent or at least one physiologically acceptable buffer.

The invention also includes at least one formulation comprising at least one IL-23 human Ig derived protein in lyophilized form in a first container, and an optional second container comprising at least one of sterile water, sterile buffered water, or at least one preservative selected from the group consisting of phenol, m-cresol, p-cresol, o-cresol, chlorocresol, benzyl alcohol, alkylparaben, benzalkonium chloride, benzethonium chloride, sodium dehydroacetate and thimerosal, or mixtures thereof in an aqueous diluent, optionally further wherein the concentration of IL-23 human Ig derived protein is reconstituted to a concentration of about 0.1 mg/ml to about 500 mg/ml, further comprising an isotonicity agent, or further comprising a physiologically acceptable buffer.

The invention further provides at least one method of treating at least one IL-23 mediated condition, comprising administering to a patient in need thereof a formulation of the invention.

The invention also provides at least one article of manufacture for human pharmaceutical use, comprising packaging material and a container comprising a solution or a lyophilized form of at least one IL-23 human Ig derived protein of the invention, optionally, further wherein said container is a glass or plastic container having a stopper for multi-use administration, optionally, further wherein said container is a blister pack, capable of being punctured and used in intravenous, intramuscular, bolus, intraperitoneal, subcutaneous, respiratory, inhalation, nasal, vaginal, rectal, buccal, sublingual, intranasal, subdermal, or transdermal administration; said container is a component of an intravenous, intramuscular, bolus, intraperitoneal, subcutaneous, respiratory, inhalation, nasal, vaginal, rectal, buccal, sublingual, intranasal, subdermal, or transdermal delivery device or system; said container is a component of an injector or pen-injector device or system for intravenous, intramuscular, bolus, intraperitoneal, subcutaneous, respiratory, inhalation, nasal, vaginal, rectal, buccal, sublingual, intranasal, sub dermal, or trans dermal delivery.

The invention further provides at least one method for preparing a formulation of at least one IL-23 human Ig derived protein of the invention, comprising admixing at least one IL-23 human Ig derived protein in at least one buffer containing saline or a salt.

The invention also provides at least one method for producing at least one IL-23 human Ig derived protein of the invention, comprising providing a host cell, transgenic animal, transgenic plant or plant cell capable of expressing in recoverable amounts said human Ig derived protein, optionally, further wherein said host cell is a mammalian cell, a plant cell or a yeast cell; said transgenic animal is a mammal; said transgenic mammal is selected from a goat, a cow, a sheep, a horse, and a non-human primate.

The invention further provides at least one transgenic animal or plant expressing at least one human Ig derived protein of the invention.

The invention further provides at least one IL-23 human Ig derived protein produced by a method of the invention.

The invention further provides at least one method for treating at least one IL-23 mediated disorder, comprising at least one of (a) administering an effective amount of a composition or pharmaceutical composition comprising at least one IL-23 human Ig derived protein to a cell, tissue, organ, animal or patient in need of such modulation, treatment or therapy; and (b) further administering, before, concurrently, and/or after said administering in (a) above, at least one selected from an immune related therapeutic, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, a neurological agent, a mineral, a nutritional, a thyroid agent, a vitamin, a calcium related hormone, an antidiarrheal, an antitussive, an antiemetic, an antiulcer, a laxative, an anticoagulant, an erythropoietin, a filgrastim, a sargramostim, an immunizing agent, an immunoglobulin, an immunosuppressive, a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, adonepezil, a tacrine, an asthma medication, a beta agonist, an inhaled steroid, a leukotriene inhibitor, a methylxanthine, a cromolyn, an epinephrine or analog, a domase alpha, a cytokine, and a cytokine antagonist.

The present invention further comprises any invention described herein and is not limited to any particular description, embodiment or example provided herein.

BRIEF DESCRIPTION OF FIGURES

FIG. 6A shows the effect of anti-IL-23 and anti-p40 antibodies on EAE progression.

FIG. 6B shows the effect of anti-IL-12 and anti-p40 antibodies on *L. Major* infection.

FIG. 6C shows the effect of anti-IL-12, anti-IL-23, and anti-p40 antibodies on *L. Major* infection.

DESCRIPTION OF THE INVENTION

Figure 1A:
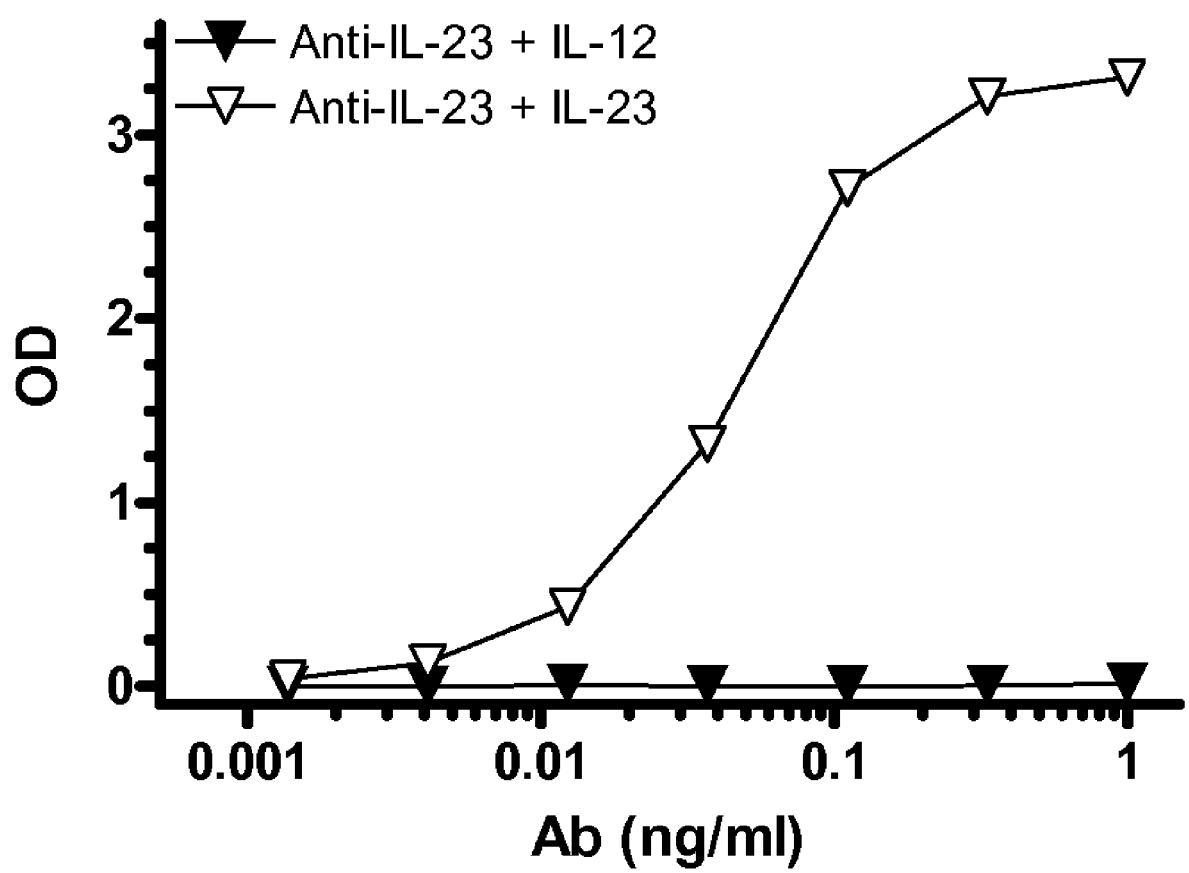
FIG. 1A is a graph showing the specificity of the anti-IL-23 antibody for IL-23.

The present invention provides immunoglobulin (Ig) derived proteins that are specific for the p40 subunit of IL-23 and which preferably do not bind to the p40 subunit of IL-12 or the IL-12 beta 2 receptor. Such Ig derived proteins include antibody and receptor fusion proteins that block the binding of IL-23 to at least one of its receptors (e.g., but not limited to, IL-23 receptor and/or IL-12 beta 1 receptor) by binding to the p19 or p40 subunits of IL-23 and/or the IL-23 receptors. Preferably, such anti-IL-23 Ig derived proteins do not bind and/or inhibit binding of IL-12 to one or more of its receptors, e.g., but not limited to IL-12 beta 1 receptor and/or IL-12 beta 2 receptor. The present invention further provides compositions, formulations, methods, devices and uses of such anti-IL-23 Ig derived proteins, including for therapeutic and diagnostic uses.

The present invention also provides Ig derived proteins that selectively inhibit IL-23 related activities and, further, do not inhibit IL-12 specific activities that are mediated by the binding of IL-12 to one or more of its receptors (e.g., but not limited to, IL-12 beta 1 receptor, or IL-12 beta 2 receptor).

The present invention further provides Ig derived proteins that are suitable for treating at least one IL-23 related condition by blocking IL-23 binding to one or more of its receptors, and where the Ig derived proteins do not block IL-12 binding to one or more of its receptors.

The present invention also provides Ig derived proteins that inhibit IL-23 activity in antigen presenting cells (APCs), such as but not limited to, macrophages, microglia, mesangial phagocytes, synovial A cells, stem cell precursors, Langerhans cells, Kuppfer cells, dendritic cells, B cells, and the like. Such APC's can be present in different tissues, e.g., but not limited to, skin, epidermis, liver, spleen, brain, spinal cord, thymus, bone marrow, joint synovial fluid, kidneys, blood, and the like. Such APC's can also be limited to outside or inside the blood brain barrier.

The present invention provides isolated, recombinant and/or synthetic IL-23 Ig derived proteins or specified portions or variants, as well as compositions and encoding nucleic acid molecules comprising at least one polynucleotide encoding at least one IL-23 Ig derived protein. Such Ig derived proteins or specified portions or variants of the present invention comprise specific full length Ig derived protein sequences, domains, fragments and specified variants thereof, and methods of making and using said nucleic acids and Ig derived proteins or specified portions or variants, including therapeutic compositions, methods and devices.

As used herein, an "anti-IL-23 Ig derived protein," "anti-IL-23 Ig derived protein portion," "anti-IL-23 Ig derived protein fragment," "anti-IL-23 Ig derived protein variant," "IL-23 Ig derived protein," "IL-23 Ig derived protein portion," or "IL-23 Ig derived protein fragment" and/or "IL-23 Ig derived protein variant" and the like decreases, blocks, inhibits, abrogates or interferes with IL-23 protein activity, binding or IL-23 protein receptor activity or binding in vitro, in situ and/or, preferably, in vivo. As used herein, "IL-12p40" or "IL-23p40" refers to the p40 subunit of IL-23, as well as active portions, fragments, isoforms, splice variants, and the like, as known in the art For example, a suitable IL-23 Ig derived protein, specified portion or variant of the present invention can bind at least one IL-23 protein or receptor and includes anti-IL-23 Ig derived proteins, antigen-binding fragments thereof, and specified portions, variants or domains thereof that bind specifically to IL-23 and/or one or more of its receptors. A suitable IL-23 Ig derived protein, specified portion, or variant can also decrease, block, abrogate, interfere, prevent and/or inhibit IL-23 protein RNA, DNA or protein synthesis, IL-23 protein release, IL-23 protein or receptor signaling, membrane IL-23 protein cleavage, IL-23 related activity, IL-23 protein production and/or synthesis, e.g., as described herein or as known in the art.

Anti-IL-23 Ig derived proteins (also termed anti-IL-23 Ig derived proteins) useful in the methods and compositions of the present invention are characterized by high affinity binding to IL-23 proteins and/or receptors, and, optionally and preferably, having low toxicity. In particular, an Ig derived protein, specified fragment or variant of the invention, where the individual components, such as the variable region, constant region and framework, individually and/or collectively, optionally and preferably possess low immunogenicity, is useful in the present invention. The Ig derived proteins that can be used in the invention are optionally characterized by their ability to treat patients for extended periods with good to excellent alleviation of symptoms and low toxicity. Low immunogenicity and/or high affinity, as well as other suitable properties, may contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably, less than about 100 measured with a double antigen enzyme immunoassay) (Elliott et al., *Lancet* 344: 1125-1127 (1994)), each of the above references entirely incorporated herein by reference.

Utility

The isolated nucleic acids of the present invention can be used for production of at least one IL-23 Ig derived protein, fragment or specified variant thereof, which can be used to effect in an cell, tissue, organ or animal (including mammals and humans), to modulate, treat, alleviate, help prevent the incidence of, or reduce the symptoms of, at least one IL-23 condition.

Such a method can comprise administering an effective amount of a composition or a pharmaceutical composition comprising at least one anti-IL-23 Ig derived protein or specified portion or variant to a cell, tissue, organ, animal or patient in need of such modulation, treatment, alleviation, prevention, or reduction in symptoms, effects or mechanisms. The effective amount can comprise an amount of about 0.001 to 500 mg/kg per single or multiple administration, or to achieve a serum concentration of 0.01-5000 µg/ml serum concentration per single or multiple administration, or any effective range or value therein, as done and determined using known methods, as described herein or known in the relevant arts.

Citations

All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. In addition to those specified herein, the following references are entirely incorporated herein by reference: Ausubel, et al., ed., Current Protocols in Molecular Biology, John Wiley & Sons, Inc., NY, N.Y. (1987-2003); Sambrook, et al., Molecular Cloning: A Laboratory Manual, $2^{nd}$ Edition, Cold Spring Harbor, N.Y. (1989); Harlow and Lane, Ig derived proteins, a Laboratory Manual, Cold Spring Harbor, N.Y. (1989); Colligan, et al., eds., Current Protocols in Immunology, John Wiley & Sons, Inc., NY (1994-2003); Colligan et al., Current Protocols in Protein Science, John Wiley & Sons, NY, N.Y., (1997-2003).

Ig Derived Proteins of the Present Invention

The term "Ig derived protein" is intended to encompass Ig derived proteins, digestion fragments, specified portions and variants thereof, including Ig derived protein mimetics or comprising portions of Ig derived proteins that mimic the structure and/or function of an antibody or specified fragment or portion thereof, including single chain Ig derived proteins and fragments thereof, and is also intended to encompass proteins that contain mimetics to therapeutic proteins, antibodies, and digestion fragments, specified portions and variants thereof, wherein the protein comprises at least one functional IL-23 protein or receptor ligand binding region (LBR) that optionally replaces at least one complementarity determining region (CDR) of the antibody from which the Ig-derived protein, portion or variant is derived. Such IL-23 IgG derived proteins, specified portions or variants include those that mimic the structure and/or function of at least one IL-23 protein antagonist, such as an IL-23 protein antibody, receptor, ligand protein, fragment or analog. Functional fragments include antigen-binding fragments that bind to human IL-23 proteins, receptors, or fragments thereof. For example, Ig derived protein fragments capable of binding to human IL-23 proteins, receptors, or fragments thereof, including, but not limited to, Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Ig derived proteins can also be produced in a variety of truncated forms using Ig derived protein genes in which one or more stop codons have been introduced upstream of the natural stop site. For example, a chimeric gene encoding a F(ab')$_2$ heavy chain portion can be designed to include DNA sequences encoding the $CH_1$, domain and/or hinge region of the heavy chain. The various portions of Ig derived proteins can be joined together chemically by conventional techniques, or can be prepared as a contiguous protein using genetic engineering techniques. For example, a nucleic acid encoding the variable and constant regions of a human Ig derived protein chain can be expressed to produce a contiguous protein. See, e.g., Colligan, Immunology, supra, sections 2.8 and 2.10, for fragmentation and Ladner et al., U.S. Pat. No. 4,946,778 and Bird, R. E. et al., Science, 242: 423-426 (1988), regarding single chain Ig derived proteins, each of which publications are entirely incorporated herein by reference.

As used herein, the term "human Ig derived protein" refers to an Ig derived protein in which substantially every part of the protein (e.g., CDR, LBR, framework, $C_L$, $C_H$ domains (e.g., $C_H1$, $C_H2$, $C_H3$), hinge, ($V_L$, $V_H$)) is substantially non-immunogenic, with only minor sequence changes or variations. Such changes or variations optionally and preferably retain or reduce the immunogenicity in humans relative to non-modified human Ig derived proteins. Thus, a human Ig derived protein is distinct from a chimeric or humanized Ig. It is pointed out that a human Ig derived protein can be produced by a non-human animal or prokaryotic or eukaryotic cell that is capable of expressing functionally rearranged human immunoglobulin (e.g., heavy chain and/or light chain) genes. Further, when a human Ig derived protein is a single chain Ig derived protein, it can comprise a linker peptide that is not found in native human Ig derived proteins. For example, an Fv can comprise a linker peptide, such as two to about eight glycine or other amino acid residues, which connects the variable region of the heavy chain and the variable region of the light chain. Such linker peptides are considered to be of human origin. IL-23 Ig derived proteins that comprise at least one IL-23 protein ligand or receptor thereof can be designed against an appropriate ligand, such as an isolated and/or IL-23 protein, receptor, or a portion thereof (including synthetic molecules, such as synthetic peptides). Preparation of such IL-23 Ig derived proteins are performed using known techniques to identify and characterize ligand binding regions or sequences of at least one IL-23 protein, receptor, or portion thereof.

Human Ig derived proteins that are specific for p40 subunit and/or IL-23 receptors can be raised against an appropriate immunogenic antigen, such as isolated IL-23 protein, receptor, or a portion thereof (including synthetic molecules, such as synthetic peptides). Preparation of immunogenic antigens, and monoclonal Ig derived protein production can be performed using any suitable technique. A variety of methods have been described (see e.g., Kohler et al., Nature, 256: 495-497 (1975) and Eur. J. Immunol. 6: 511-519 (1976); Milstein et al., Nature 266: 550-552 (1977); Koprowski et al, U.S. Pat. No. 4,172,124; Harlow, E. and D. Lane, 1988, Ig derived proteins: A Laboratory Manual, (Cold Spring Harbor Laboratory: Cold Spring Harbor, N.Y.); Current Protocols In Molecular Biology, Vol. 2 (e.g., Supplement 27, Summer '94), Ausubel, F. M. et al., Eds., (John Wiley & Sons: New York, N.Y.), Chapter 11, (1991-2003)), each of which is entirely incorporated herein by reference. Generally, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, or heteromyelomas, fusion products thereof, or any cell or fusion cell derived therefrom, or any other suitable cell line as known in the art, see, e.g., www.atcc.org, www.lifetech.com., and the like, each of which is entirely incorporated herein by reference) with Ig derived protein producing cells, such as, but not limited to, isolated or cloned spleen cells, or any other cells expressing heavy or light chain constant, variable, framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, each entirely incorporated herein by reference.

Ig derived protein producing cells can be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an Ig derived protein, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce Ig derived proteins with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, Del.; Biovation, Aberdeen, Scotland, UK; BioInvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350, 260(May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); WO96/13583, WO97/08320 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400;

(Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. 1 mm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)), each of which is entirely incorporated herein by reference.

Methods for humanizing non-human Ig derived proteins can also be used and are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature 321:522 (1986); Riechmann et al., Nature 332:323 (1988); Verhoeyen et al., Science 239:1534 (1988), each of which is entirely incorporated herein by reference), by substituting rodent CDRs for CDR sequences for the corresponding sequences of a human antibody. Accordingly, such "humanized" Ig derived proteins are chimeric Ig derived proteins (Cabilly et al., supra), wherein substantially less than an intact human variable domain has been substituted by the corresponding sequence from a non-human species. In practice, humanized Ig derived proteins are typically human Ig derived proteins in which some CDR residues and possibly some FR residues are substituted by residues from analogous sites in rodent Ig derived proteins.

The choice of human variable domains, both light and heavy, to be used in making the humanized Ig derived proteins can be used to reduce antigenicity. According to the so-called "best-fit" method, the sequence of the variable domain of a rodent antibody is screened against the entire library of known human variable-domain sequences. The human sequence that is closest to that of the rodent is then accepted as the human framework (FR) for the humanized antibody (Sims et al., J. Immunol. 151: 2296 (1993); Chothia and Lesk, J. Mol. Biol. 196:901 (1987), each of which is entirely incorporated herein by reference). Another method uses a particular framework derived from the consensus sequence of all human Ig derived proteins of a particular subgroup of light or heavy chains. The same framework can be used for several different humanized Ig derived proteins (Carter et al., Proc. Natl. Acad. Sci. U.S.A. 89:4285 (1992); Presta et al., J. Immunol. 151:2623 (1993), each of which is entirely incorporated herein by reference).

Ig derived proteins can also optionally be humanized with retention of high affinity for the antigen and other favorable biological properties. To achieve this goal, according to a preferred method, humanized Ig derived proteins are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Human monoclonal Ig derived proteins can be made by the hybridoma method. Human myeloma and mouse-human heteromyeloma cell lines for the production of human monoclonal Ig derived proteins have been described, for example, by Kozbor, J. Immunol. 133:3001 (1984); Brodeur et al., Monoclonal Antibody Production Techniques and Applications, pp. 51-63 (Marcel Dekker, Inc., New York, 1987); and Boerner et al., J. Immunol. 147:86 (1991), each of which is entirely incorporated herein by reference.

Alternatively, phage display technology, in addition to that presented above, can be used to produce human Ig derived proteins and antibody fragments in vitro, from immunoglobulin variable (V) domain gene repertoires from unimmunized donors. According to one non-limiting example of this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson et al., Current Opinion in Structural Biology 3:564 (1993), each of which is entirely incorporated herein by reference.

Several sources of V-gene segments can be used for phage display. Clackson et al., Nature 352:624 (1991) isolated a diverse array of anti-oxazolone Ig derived proteins from a small random combinatorial library of V genes derived from the spleens of immunized mice. A repertoire of V genes from unimmunized human donors can be constructed and Ig derived proteins to a diverse array of antigens (including self-antigens) can be isolated essentially following the techniques described by Marks et al., J. Mol. Biol. 222:581 (1991), or Griffith et al., EMBO J. 12:725 (1993), each of which is entirely incorporated herein by reference.

In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technol. 10:779 (1992)). In this method, the affinity of "primary" human Ig derived proteins obtained by phage display can be improved by sequentially replacing the heavy and light chain V region genes with repertoires of naturally occurring variants (repertoires) of V domain genes obtained from unimmunized donors. This technique allows the production of Ig derived proteins and antibody fragments with affinities in the nM range.

A strategy for making very large phage antibody repertoires has been described by Waterhouse et al., Nucl. Acids Res. 21:2265 (1993). Gene shuffling can also be used to derive human Ig derived proteins from rodent Ig derived proteins, where the human antibody has similar affinities and specificities to the starting rodent antibody. According to this method, which is also referred to as "epitope imprinting," the heavy or light chain V domain gene of rodent Ig derived proteins obtained by phage display technique is replaced with a repertoire of human V domain genes, creating rodent-human chimeras. Selection with antigen results in isolation of human variable domains capable of restoring a functional antigen-binding site, i.e. the epitope governs (imprints) the choice of partner. When the process is repeated in order to replace the remaining rodent V domain, a human antibody is obtained (see PCT WO 93/06213, published 1 Apr. 1993). Unlike traditional humanization of rodent Ig derived proteins by CDR grafting, this technique provides completely human Ig derived proteins, which have no framework or CDR residues of rodent origin.

Bispecific Ig derived proteins can also be used that are monoclonal, preferably human or humanized, Ig derived proteins that have binding specificities for at least two different antigens. In the present case, one of the binding specificities is for at least one IL-23 protein; the other one is for any other antigen. For example, bispecific Ig derived proteins specifically binding an IL-23 protein and at least one neurotrophic factor, or two different types of IL-23 polypeptides are within the scope of the present invention.

Methods for making bispecific Ig derived proteins are known in the art. Traditionally, the recombinant production of bispecific Ig derived proteins is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published 13 May 1993, and in Traunecker et al., EMBO J. 10:3655 (1991), entirely incorporated herein by reference.

According to a different and more preferred approach, antibody-variable domains with the desired binding specificities (antibody-antigen combining sites) are fused to immunoglobulin constant-domain sequences. The fusion preferably is with an immunoglobulin heavy-chain constant domain, comprising at least part of the hinge, the second heavy chain constant region (C.sub.H 2), and the third heavy chain constant region (C.sub.H 3). It is preferred to have the first heavy-chain constant region (C.sub.H 1), containing the site necessary for light-chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the production of at least two polypeptide chains in equal ratios results in high yields or when the ratios are of no particular significance. In a preferred embodiment of this approach, the bispecific Ig derived proteins are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. For further details of generating bispecific Ig derived proteins, see, for example, Suresh et al., Methods in Enzymology 121:210 (1986).

Heteroconjugate Ig derived proteins are also within the scope of the present invention. Heteroconjugate Ig derived proteins are composed of two covalently joined Ig derived proteins. Such Ig derived proteins have, for example, been proposed to target immune system cells to unwanted cells (U.S. Pat. No. 4,676,980), and for treatment of HIV infection (WO 91/00360; WO 92/00373; and EP 03089) Heteroconjugate Ig derived proteins can be made using any convenient cross-linking methods. Suitable cross-linking agents are well known in the art, and are disclosed in U.S. Pat. No. 4,676,980, along with a number of cross-linking techniques.

In a preferred embodiment, at least one anti-IL-23 Ig derived protein or specified portion or variant of the present invention is produced by a cell line, a mixed cell line, an immortalized cell or clonal population of immortalized cells. Immortalized IL-23 producing cells can be produced using suitable methods, for example, fusion of a human Ig derived protein-producing cell and a heteromyeloma or immortalization of an activated human B cell via infection with Epstein Barr virus (Niedbala et al., *Hybridoma*, 17(3):299-304 (1998); Zanella et al., *J Immunol Methods*, 156(2):205-215 (1992); Gustafsson et al., *Hum Ig derived proteins Hybridomas*, 2(1)26-32 (1991)). Preferably, the human anti-human IL-23 proteins, fragments, specified portions or variants are generated by immunization of a transgenic animal (e.g., mouse, rat, hamster, non-human primate, and the like) capable of producing a repertoire of human Ig derived proteins, as described herein and/or as known in the art. Cells that produce a human anti-IL-23 Ig derived protein can be isolated from such animals and immortalized using suitable methods, such as the methods described herein.

Transgenic mice that can produce a repertoire of human Ig derived proteins that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814259 A2, Lonberg et al. GB 2 272 440 A, Lonberg et al. *Nature* 368:856-859 (1994), Taylor et al., *Int. Immunol.* 6(4)579-591 (1994), Green et al., *Nature Genetics* 7:13-21 (1994), Mendez et al., *Nature Genetics* 15:146-156 (1997), Taylor et al., *Nucleic*

*Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce Ig derived proteins encoded by endogenous genes.

The term "functionally rearranged," as used herein refers to a segment of DNA from an immunoglobulin locus that has undergone V(D)J recombination, thereby producing an immunoglobulin gene that encodes an immunoglobulin chain (e.g., heavy chain, light chain), or any portion thereof. A functionally rearranged immunoglobulin gene can be directly or indirectly identified using suitable methods, such as, for example, nucleotide sequencing, hybridization (e.g., Southern blotting, Northern blotting) using probes that can anneal to coding joints between gene segments or enzymatic amplification of immunoglobulin genes (e.g., polymerase chain reaction) with primers that can anneal to coding joints between gene segments. Whether a cell produces an Ig derived protein comprising a particular variable region or a variable region comprising a particular sequence (e.g., at least one CDR sequence) can also be determined using suitable methods. In one example, mRNA can be isolated from an Ig derived protein-producing cell (e.g., a hybridoma or recombinant cell or other suitable source) and used to produce cDNA encoding the Ig derived protein or specified portion or variant thereof. The cDNA can be cloned and sequenced or can be amplified (e.g., by polymerase chain reactionor other known and suitable methods) using a first primer that anneals specifically to a portion of the variable region of interest (e.g., CDR, coding joint) and a second primer that anneals specifically to non-variable region sequences (e.g., $C_H1$, $V_H$).

Screening Ig derived protein or specified portion or variants for specific binding to similar proteins or fragments can be conveniently achieved using peptide display libraries. This method involves the screening of large collections of peptides for individual members having the desired function or structure. Ig derived protein screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278. Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge Ig derived protein Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; 5,223,409, 5,403,484, 5,571,698, 5,837,500, assigned to Dyax, 5,427,908, 5,580,717, assigned to Affymax; 5,885,793, assigned to Cambridge Ig derived protein Technologies; 5,750,373, assigned to Genentech, 5,618,920, 5,595,898, 5,576,195, 5,698,435, 5,693,493, 5,698,417, assigned to Xoma, Colligan, supra; Ausubel, supra; or Sambrook, supra, each of the above patents and publications entirely incorporated herein by reference.

Ig derived proteins, specified portions and variants of the present invention can also be prepared by providing at least one IL-23 Ig derived protein or specified portion or variant encoding nucleic acid to transgenic animals or mammals, such as goats, cows, horses, sheep, and the like, that produce such Ig derived proteins or specified portions or variants in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Ig derived proteins, specified portions and variants of the present invention can additionally be prepared using at least one IL-23 Ig derived protein or specified portion or variant encoding nucleic acid to provide transgenic plants and cultured plant cells (e.g., but not limited to, tobacco and maize) that produce such Ig derived proteins, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Ig derived proteins have also been produced in large amounts from transgenic plant seeds including Ig derived protein fragments, such as single chain Ig derived proteins (scFv's), including tobacco seeds and potato tubers. See, e.g., Conrad et al., Plant Mol. Biol. 38:101-109 (1998) and reference cited therein. Thus, Ig derived proteins, specified portions and variants of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The Ig derived proteins of the invention can bind human IL-23 proteins, receptors, and/or fragments with a wide range of affinities ($K_D$). In a preferred embodiment, at least one human mAb of the present invention can optionally bind human IL-23 proteins, receptors, and/or fragments with high affinity. For example, a human mAb can bind human IL-23 proteins, receptors, and/or fragments with a $K_D$ equal to or less than about $10^{-9}$ M or, more preferably, with a $K_D$ equal to or less than about 0.1-9.9 (or any range or value therein) X $10^{-10}$ M, $10^{-11}$, $10^{-12}$, $10^{-13}$ or any range or value therein.

The affinity or avidity of an Ig derived protein for an antigen can be determined experimentally using any suitable method. (See, for example, Berzofsky, et al., "Ig derived protein-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular Ig derived protein-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of Ig derived protein and antigen, and a standardized buffer, such as the buffer described herein.

Nucleic Acid Molecules

Using the information provided herein, such as the nucleotide sequences encoding at least 90-100% of the contiguous amino acids of at least one IL-23 Ig derived protein of the present invention, specified fragments, variants or consensus sequences thereof, or a deposited vector comprising at least one of these sequences, a nucleic acid molecule of the present invention encoding at least one IL-23 Ig derived protein or specified portion or variant can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain or light chain, respectively; nucleic acid molecules comprising the coding sequence for an IL-23 Ig derived protein or specified portion or variant; and nucleic acid molecules which comprise a nucleotide sequence substantially different from those described above but which, due to the degeneracy of the genetic code, still encode at least one IL-23 Ig derived protein as described herein and/or as known in the art. Of course, the genetic code is well known in the art. Thus, it would be routine for one skilled in the art to generate such degenerate nucleic acid variants that code for specific IL-23 Ig derived protein or specified portion or variants of the present invention. See, e.g., Ausubel, et al., supra, and such nucleic acid variants are included in the present invention.

As indicated herein, nucleic acid molecules of the present invention which comprise a nucleic acid encoding an IL-23 Ig derived protein or specified portion or variant can include, but are not limited to, those encoding the amino acid sequence of an Ig derived protein fragment, by itself; the coding sequence for the entire Ig derived protein or a portion thereof; the coding sequence for an Ig derived protein, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an Ig derived protein or specified portion or variant can be fused to a marker sequence, such as a sequence encoding a peptide that facilitates purification of the fused Ig derived protein or specified portion or variant comprising an Ig derived protein fragment or portion.

Polynucleotides Selectively Hybridizing to a Polynucleotide as Described Herein

The present invention provides isolated nucleic acids that hybridize under selective hybridization conditions to a polynucleotide encoding a IL-23 Ig derived protein of the present invention. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an Ig derived protein or specified portion or variant encoded by the polynucleotides described herein. The polynucleotides of this invention embrace nucleic acid sequences that can be employed for selective hybridization to a polynucleotide encoding an Ig derived protein or specified portion or variant of the present invention. See, e.g., Ausubel, supra; Colligan, supra, each entirely incorporated herein by reference.

Construction of Nucleic Acids

The isolated nucleic acids of the present invention can be made using (a) recombinant methods, (b) synthetic techniques, and (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 90-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; 5,142,033 to Innis; 5,122,464 to Wilson, et al.; 5,091,310 to Innis; 5,066,584 to Gyllensten, et al; 4,889,818 to Gelfand, et al; 4,994,370 to Silver, et al; 4,766,067 to Biswas; 4,656,134 to Ringold) and RNA mediated amplification that uses anti-sense RNA to the target sequence as a template for double-stranded DNA synthesis (U.S. Pat. No. 5,130,238 to Malek, et al., with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990).

Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example, a cDNA or a genomic sequence encoding an Ig derived protein or specified portion or variant of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

A polynucleotide of the present invention can be expressed in either sense or anti-sense orientation as desired. It will be appreciated that control of gene expression in either sense or anti-sense orientation can have a direct impact on the observable characteristics.

Another method of suppression is sense suppression. Introduction of nucleic acid configured in the sense orientation has been shown to be an effective means by which to block the transcription of target genes.

A variety of cross-linking agents, alkylating agents and radical generating species as pendant groups on polynucleotides of the present invention can be used to bind, label, detect and/or cleave nucleic acids. Knorre, et al., Biochimie 67:785-789 (1985); Vlassov, et al., Nucleic Acids Res. 14:4065-4076 (1986); Iverson and Dervan, J. Am. Chem. Soc. 109:1241-1243 (1987); Meyer, et al., J. Am. Chem. Soc. 111:8517-8519 (1989); Lee, et al., Biochemistry 27:3197-3203 (1988); Home, et al., J. Am. Chem. Soc. 112:2435-2437 (1990); Webb and Matteucci, J. Am. Chem. Soc. 108:2764-2765 (1986); Nucleic Acids Res. 14:7661-7674 (1986); Feteritz, et al., J. Am. Chem. Soc. 113:4000 (1991). Various compounds to bind, detect, label, and/or cleave nucleic acids are known in the art. See, for example, U.S. Pat. Nos. 5,543,507; 5,672,593; 5,484,908; 5,256,648; and 5,681,941, each entirely incorporated herein by reference.

Vectors And Host Cells

The present invention also relates to vectors that include isolated nucleic acid molecules of the present invention, host cells that are genetically engineered with the recombinant vectors, and the production of at least one IL-23 Ig derived protein or specified portion or variant by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; and 5,179,017, ampicillin, neomycin (G418), mycophenolic acid, or glutamine synthetase (GS, U.S. Pat. Nos. 5,122,464; 5,770,359; and 5,827,739) resistance for eukaryotic cell culture, and tetracycline or ampicillin resistance genes for culturing in E. coli and other bacteria or prokaryotics (the above patents are entirely incorporated herein by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one Ig derived protein or specified portion or variant of the present invention can be expressed in a modified form, such as a fusion protein, and can include not only secretion signals, but also additional heterologous functional regions. For instance, a region of additional amino acids, particularly charged amino acids, can be added to the N-terminus of an Ig derived protein or specified portion or variant to improve stability and persistence in the host cell, during purification, or during subsequent handling and storage. Also, peptide moieties can be added to an Ig derived protein or specified portion or variant of the present invention to facilitate purification. Such regions can be removed prior to final preparation of an Ig derived protein or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an Ig derived protein or specified portion or variant of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the Ig derived proteins, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Ig Derived Protein or Specified Portion or Variant Thereof

A IL-23 Ig derived protein or specified portion or variant can be recovered and purified from recombinant cell cultures by well-known methods, including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See e.g., Colligan, Current Protocols in Immunology, or Current Protocols in Protein Science, John Wiley & Sons, NY, N.Y., (1997-2003), e.g., Chapters 1, 4, 6, 8, 9, 10, each entirely incorporated herein by reference.

Ig derived proteins or specified portions or variants of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the Ig derived protein or specified portion or variant of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

IL-23 Ig Derived Proteins, Fragments and/or Variants

The isolated Ig derived proteins of the present invention comprise an Ig derived protein or specified portion or variant encoded by any one of the polynucleotides of the present invention as discussed more fully herein, or any isolated or prepared Ig derived protein or specified portion or variant thereof.

Preferably, the human Ig derived protein or antigen-binding fragment binds human IL-23 proteins, receptors, and/or fragments and, thereby substantially neutralizes the biological activity of the protein. An Ig derived protein, or specified portion or variant thereof, that partially or preferably substantially neutralizes at least one biological activity of at least one IL-23 protein or fragment can bind the protein, receptor and/or fragment and thereby inhibit activities mediated through the binding of IL-23 to at least one IL-23 receptor or through other IL-23-dependent or mediated mechanisms. As used herein, the term "neutralizing Ig derived protein" refers to an Ig derived protein that can inhibit human p40 or p19 protein or fragment related-dependent activity by about 20-120%, preferably by at least about 60, 70, 80, 90, 91, 92, 93, 94, 95, 96, 97, 98, 99, 100% or more depending on the assay. The capacity of anti-human IL-23 Ig derived protein or specified portion or variant to inhibit human IL-23 related-dependent activity is preferably assessed by at least one suitable IL-23 Ig derived protein or protein assay, as described herein and/or as known in the art. A human Ig derived protein or specified portion or variant of the invention can be of any class (IgG, IgA, IgM, IgE, IgD, etc.) or isotype and can comprise a kappa or lambda light chain. In one embodiment, the human Ig derived protein or specified portion or variant comprises an IgG heavy chain or defined fragment, for example, at least one of isotypes, IgG1, IgG2, IgG3 or IgG4. Ig derived proteins of this type can be prepared by employing a transgenic mouse or other trangenic non-human mammal comprising at least one human light chain (e.g., IgG, IgA and IgM) (e.g., γ1, γ2, γ3, γ4) transgene as described herein and/or as known in the art. In another embodiment, the anti-human IL-23 Ig derived protein or specified portion or variant thereof comprises an IgG1 heavy chain and an IgG1 light chain.

At least one Ig derived protein or specified portion or variant of the invention binds at least one specified epitope specific to at least one IL-23 protein, receptor, subunit, fragment, portion or any combination thereof. The at least one epitope can comprise at least one Ig derived protein binding region that comprises at least one portion of said protein, which epitope is preferably comprised of at least one extracellular, soluble, hydrophillic, external or cytoplasmic portion of said protein. As non-limiting examples, an IL-23 Ig derived protein or specified portion or variant specifically binds at least one epitope comprising (1) at least 1-3 amino acids of the entire amino acid sequence, selected from the group consisting of at least one p40 subunit of human IL-23, and (2) at least 1-3 amino acids of the entire amino acid sequence of one or more IL-23 receptors. The at least one specified epitope can comprise any combination of at least one amino acid of the p40 subunit of a human interleukin-23, such as but not limited to, 1, 2, 3, 4, 5, 6, 7, 8, 9, 10, 11, 12, 13 or 14 amino acids of at least one of, 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 280-290, 290-300, 300-306, 1-7, 14-21, 29-52, 56-73, 83-93, 96-105, 156-175, 194-204, 208-246, 254-273, 279-281, or 289-300 of SEQ ID NO: 1 (human p40 subunit, 306 amino acids). Preferred examples include 1, 2, 3, 4, 5, 6, 7, 8, 9 or 10 amino acids of the extracellular domain of human IL-23p40 (SEQ ID NO:1), comprised of SEQ ID NO: 1. More specifically, the epitope regions are predicted to comprise Seg 1 (amino acids 97-101 of SEQ ID NO:1), and/or Seg 2 (amino acids 138-145 of SEQ ID NO:1), and/or Seg 3 (amino acids 250-269 of SEQ ID NO:1) of SEQ ID NO:1.

These predicted epitopes are not available on the p40 subunit of IL-12, which is coupled to the p35 subunit of IL-12. These epitopes are available on the p40 subunit of IL-23, which is coupled to the p19 subunit of IL-23. Accordingly, the antibody of the present invention substantially does not react with IL-12 p40 and inhibits the interaction between IL-23 p40 and the IL-12Rβ1 receptor subunit Generally, the human Ig derived protein or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. As a non-limiting example, the Ig derived protein or antigen-binding portion or variant can comprise at least one of the heavy chain CDR3, and/or a light chain CDR3. In a particular embodiment, the Ig derived protein or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3. In another particular embodiment, the Ig derived protein or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3. Such Ig derived proteins can be prepared by chemically joining together the various portions (e.g., CDRs, framework) of the Ig derived protein using conventional techniques, by preparing and expressing a (i.e., one or more) nucleic acid molecule that encodes the Ig derived protein using conventional techniques of recombinant DNA technology or by using any other suitable method.

The anti-IL-23 Ig derived protein can comprise at least one of a heavy or light chain variable region having a defined amino acid sequence. For example, in a preferred embodiment, the anti-IL-23 Ig derived protein comprises at least one of at least one heavy chain variable region and/or at least one light chain variable region. Human Ig derived proteins that bind to human IL-23 proteins, receptors, and/or fragments and that comprise a defined heavy or light chain variable region can be prepared using suitable methods, such as phage display (Katsube, Y., et al., *Int J Mol Med*, 1(5):863-868

(1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human IL-23 proteins, receptors, and/or fragments thereof to elicit the production of Ig derived proteins. If desired, the Ig derived protein producing cells can be isolated and hybridomas or other immortalized Ig derived protein-producing cells can be prepared as described herein and/or as known in the art. Alternatively, the Ig derived protein, specified portion or variant can be expressed using the encoding nucleic acid or portion thereof in a suitable host cell.

The invention also relates to Ig derived proteins, antigen-binding fragments, immunoglobulin chains and CDRs comprising amino acids in a sequence that is substantially the same as an amino acid sequence described herein. Preferably, such Ig derived proteins or antigen-binding fragments and Ig derived proteins comprising such chains or CDRs can bind human IL-23 proteins, receptors, and/or fragments with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up IL-23 Ig derived proteins or specified portions or variants of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |

-continued

| SINGLE LETTER CODE | THREE LETTER CODE | NAME | THREE NUCLEOTIDE CODON(S) |
|---|---|---|---|
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

An IL-23 Ig derived protein or specified portion or variant of the present invention can include one or more amino acid substitutions, deletions or additions, either from natural mutations or human manipulation, as specified herein.

Of course, the number of amino acid substitutions a skilled artisan would make depends on many factors, including those described above. Generally speaking, the number of amino acid substitutions, insertions or deletions for any given IL-23 Ig derived polypeptide will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an IL-23 Ig derived protein or specified portion or variant of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one IL-23 neutralizing activity. Sites that are critical for Ig derived protein or specified portion or variant binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

The Ig derived proteins or specified portions or variants of the present invention, or specified variants thereof, can comprise any number of contiguous amino acid residues from an Ig derived protein or specified portion or variant of the present invention, wherein that number is selected from the group of integers consisting of from 10-100% of the number of contiguous residues in a IL-23 Ig derived protein or specified portion or variant. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active Ig derived protein or specified portion or variant of the present invention. Biologically active Ig derived proteins or specified portions or variants have a specific activity at least 20%, 30%, or 40%, and preferably at least 50%, 60%, or 70%, and most preferably at least 80%, 90%, or 95%-1000% of that of the native (non-synthetic), endogenous or related and known Ig derived protein or specified portion or variant. Methods of assaying and quantifying measures of enzymatic activity and substrate specificity, are well known to those of skill in the art.

In another aspect, the invention relates to human Ig derived proteins and antigen-binding fragments, as described herein, which are modified by the covalent attachment of an organic moiety.

Such modification can produce an Ig derived protein or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified Ig derived proteins and antigen-binding fragments of the invention can comprise one or more organic moieties that are covalently bonded, directly or indirectly, to the Ig derived protein or specified portion or variant. Each organic moiety that is bonded to an Ig derived protein or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an Ig derived protein modified by the covalent attachment of polylysine is encompassed by the invention. Hydrophilic polymers suitable for modifying Ig derived proteins of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the Ig derived protein of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used.

The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying Ig derived proteins of the invention can be saturated or can contain one or more units of unsaturation. Fatty acids that are suitable for modifying Ig derived proteins of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$-), n-tetracontanoate ($C_{40}$-), cis-$\Delta$9-octadecanoate ($C_{18}$, oleate), all cis-$\Delta$5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human Ig derived proteins and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example, a divalent $C_1$-$C_{12}$ group wherein one or more carbon atoms can be replaced by a heteroatom, such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified Ig derived proteins of the invention can be produced by reacting a human Ig derived protein or antigen-binding fragment with a modifying agent. For example, the organic moieties can be bonded to the Ig derived protein in a non-site specific manner by employing an amine-reactive modifying agent, for example, an NHS ester of PEG. Modified human Ig derived proteins or antigen-binding fragments can also be prepared by reducing disulfide bonds (e.g., intra-chain disulfide bonds) of an Ig derived protein or antigen-binding fragment. The reduced Ig derived protein or antigen-binding fragment can then be reacted with a thiol-reactive modifying agent to produce the modified Ig derived protein of the invention. Modified human Ig derived proteins and antigen-binding fragments comprising an organic moiety that is bonded to specific sites of an Ig derived protein or specified portion or variant of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Pro-* tein Sci. 6(10):2233-2241 (1997); Itoh et al., *Bioorg. Chem.*, 24(1): 59-68 (1996); Capellas et al., *Biotechnol Bioeng.*, 56(4):456-463 (1997)), and the methods described in Hermanson, G. T., *Bioconjugate Techniques*, Academic Press: San Diego, Calif. (1996).

Anti-Idiotype Antibodies to IL-23 Ig Derived Protein Compositions

In addition to IL-23 Ig derived proteins, the present invention is also directed to an anti-idiotypic (anti-Id) antibody specific for the IL-23 Ig derived protein of the invention. An anti-Id antibody is an antibody that recognizes unique determinants generally associated with the antigen-binding region of another antibody. The anti-Id can be prepared by immunizing an animal of the same species and genetic type (e.g., mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

The present invention also provides at least one IL-23 Ig derived protein composition comprising at least one, at least two, at least three, at least four, at least five, at least six or more anti-IL-1-23 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the IL-23 Ig derived protein amino acid sequence, or specified fragments, domains or variants thereof.

Antibody Compositions Comprising Further Therapeutically Active Ingredients

The antibody compositions of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

The anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The CV drug can be at least one selected from inotropics, antiarrhythmics, antianginals, antihypertensives, antilipemics, and miscellaneous cardiovascular drugs. The CNS drug can be at least one selected from normarcotic analgesics or at least one selected from antipyretics, nonsteroidal anti-inflammatory drugs, narcotic or at least one opiod analgesics, sedative-hypnotics, anticonvulsants, antidepressants, anti-anxiety drugs, antipsychotics, central nervous system stimulants, antiparkinsonians, and miscellaneous central nervous system drugs. The ANS drug can be at least one selected from cholinergics (parasympathomimetics), anticholinergics, adrenergics (sympathomimetics), adrenergic blockers (sympatholytics), skeletal muscle relaxants, and neuromuscular blockers. The respiratory tract drug can be at least one selected from antihistamines, bronchodilators, expectorants or at least one antitussive, and miscellaneous respiratory drugs. The GI tract drug can be at least one selected from antacids or at least one adsorbent or at least one antiflatulent, digestive enzyme or at least one gallstone solubilizer, antidiarrheals, laxatives, antiemetics, and antiulcer drugs. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The drug for fluid and electrolyte balance can be at least one selected from diuretics, electrolytes or at least one replacement solution, acidifier or at least one alkalinizer. The hematologic drug can be at least one selected from hematinics, anticoagulants, blood derivatives, and thrombolytic enzymes. The antineoplastics can be at least one selected from alkylating drugs, antimetabolites, antibiotic antineoplastics, antineoplastics that alter hormone balance, and miscellaneous antineoplastics. The immunomodulation drug can be at least one selected from immunosuppressants, vaccines or at least one toxoid, antitoxin or at least one antivenin, immune serum, and biological response modifier. The ophthalmic, otic, and nasal drugs can be at least one selected from ophthalmic anti-infectives, ophthalmic anti-inflammatories, miotics, mydriatics, ophthalmic vasoconstrictors, miscellaneous ophthalmics, otics, and nasal drugs. The topical drug can be at least one selected from local anti-infectives, scabicides or at least one pediculicide or topical corticosteroid. The nutritional drug can be at least one selected from vitamins, minerals, or calorics. See, e.g., contents of *Nursing* 2001 *Drug Handbook*, supra.

The at least one amebicide or antiprotozoal can be at least one selected from atovaquone, chloroquine hydrochloride, chloroquine phosphate, metronidazole, metronidazole hydrochloride, and pentamidine isethionate. The at least one anthelmintic can be at least one selected from mebendazole, pyrantel pamoate, and thiabendazole. The at least one antifungal can be at least one selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. The at least one antimalarial can be at least one selected from chloroquine hydrochloride, chloroquine phosphate, doxycycline, hydroxychloroquine sulfate, mefloquine hydrochloride, primaquine phosphate, pyrimethamine, and pyrimethamine with sulfadoxine. The at least one antituberculotic or antileprotic can be at least one selected from clofazimine, cycloserine, dapsone, ethambutol hydrochloride, isoniazid, pyrazinamide, rifabutin, rifampin, rifapentine, and streptomycin sulfate. The at least one aminoglycoside can be at least one selected from amikacin sulfate, gentamicin sulfate, neomycin sulfate, streptomycin sulfate, and tobramycin sulfate. The at least one penicillin can be at least one selected from amoxcillin/clavulanate potassium, amoxicillin trihydrate, ampicillin, ampicillin sodium, ampicillin trihydrate, ampicillin sodium/sulbactam sodium, cloxacillin sodium, dicloxacillin sodium, mezlocillin sodium, nafcillin sodium, oxacillin sodium, penicillin G benzathine, penicillin G potassium, penicillin G procaine, penicillin G sodium, penicillin V potassium, piperacillin sodium, piperacillin sodium/tazobactam sodium, ticarcillin disodium, and ticarcillin disodium/clavulanate potassium. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef The at least one tetracycline can be at least one selected from demeclocycline hydrochloride, doxycycline calcium, doxycycline hyclate, doxycycline hydrochloride, doxycycline monohydrate, minocycline hydrochloride, and tetracycline hydrochloride. The at least one sulfonamide can be at least one selected from co-trimoxazole, sulfadiazine, sulfamethoxazole, sulfisoxazole, and sulfisoxazole acetyl. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one antiviral can be at least one selected from abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine. The at least one macroline anti-infective can be at least one selected from azithromycin, clarithromycin, dirithromycin, erythromycin base, erythromycin estolate, erythromycin ethylsuccinate, erythromycin lactobionate, and erythromycin stearate. The at least one miscellaneous anti-infective can be at least one selected from aztreonam, bacitracin, chloramphenicol sodium sucinate, clindamycin hydrochloride, clindamycin palmitate hydrochloride, clindamycin phosphate, imipenem and cilastatin sodium, meropenem, nitrofurantoin macrocrystals, nitrofurantoin microcrystals, quinupristin/dalfopristin, spectinomycin hydrochloride, trimethoprim, and vancomycin hydrochloride. (See, e.g., pp. 24-214 of Nursing 2001 Drug Handbook.)

The at least one inotropic can be at least one selected from aminone lactate, digoxin, and milrinone lactate. The at least one antiarrhythmic can be at least one selected from adenosine, amiodarone hydrochloride, atropine sulfate, bretylium tosylate, diltiazem hydrochloride, disopyramide, disopyramide phosphate, esmolol hydrochloride, flecamide acetate, ibutilide fumarate, lidocaine hydrochloride, mexiletine hydrochloride, moricizine hydrochloride, phenyloin, phenyloin sodium, procainamide hydrochloride, propafenone hydrochloride, propranolol hydrochloride, quinidine bisulfate, quinidine gluconate, quinidine polygalacturonate, quinidine sulfate, sotalol, tocamide hydrochloride, and verapamil hydrochloride. The at least one antianginal can be at least one selected from amlodipidine besylate, amyl nitrite, bepridil hydrochloride, diltiazem hydrochloride, isosorbide dinitrate, isosorbide mononitrate, nadolol, nicardipine hydrochloride, nifedipine, nitroglycerin, propranolol hydrochloride, verapamil, and verapamil hydrochloride. The at least one antihypertensive can be at least one selected from acebutolol hydrochloride, amlodipine besylate, atenolol, benazepril hydrochloride, betaxolol hydrochloride, bisoprolol fumarate, candesartan cilexetil, captopril, carteolol hydrochloride, carvedilol, clonidine, clonidine hydrochloride, diazoxide, diltiazem hydrochloride, doxazosin mesylate, enalaprilat, enalapril maleate, eprosartan mesylate, felodipine, fenoldopam mesylate, fosinopril sodium, guanabenz acetate, guanadrel sulfate, guanfacine hydrochloride, hydralazine hydrochloride, irbesartan, isradipine, labetalol hydrchloride, lisinopril, losartan potassium, methyldopa, methyldopate hydrochloride, metoprolol succinate, metoprolol tartrate, minoxidil, moexipril hydrochloride, nadolol, nicardipine hydrochloride, nifedipine, nisoldipine, nitroprusside sodium, penbutolol sulfate, perindopril erbumine, phentolamine mesylate, pindolol, prazosin hydrochloride, propranolol hydrochloride, quinapril hydrochloride, ramipril, telmisartan, terazosin hydrochloride, timolol maleate, trandolapril, valsartan, and verapamil hydrochloride. The at least one antilipemic can be at least one selected from atorvastatin calcium, cerivastatin sodium, cholestyramine, colestipol hydrochloride, fenofibrate (micronized), fluvastatin sodium, gemfibrozil, lovastatin, niacin, pravastatin sodium, and simvastatin. The at least one miscellaneous CV drug can be at least one selected from abciximab, alprostadil, arbutamine hydrochloride, cilostazol, clopidogrel bisulfate, dipyridamole, eptifibatide, midodrine hydrochloride, pentoxifylline, ticlopidine hydrochloride, and tirofiban hydrochloride. (See, e.g., pp. 215-336 of Nursing 2001 Drug Handbook.)

The at least one normarcotic analgesic or antipyretic can be at least one selected from acetaminophen, aspirin, choline magnesium trisalicylate, diflunisal, and magnesium salicylate. The at least one nonsteroidal anti-inflammatory drug can be at least one selected from celecoxib, diclofenac potassium, diclofenac sodium, etodolac, fenoprofen calcium, flurbiprofen, ibuprofen, indomethacin, indomethacin sodium trihydrate, ketoprofen, ketorolac tromethamine, nabumetone, naproxen, naproxen sodium, oxaprozin, piroxicam, rofecoxib, and sulindac. The at least one narcotic or opiod analgesic can be at least one selected from alfentanil hydrochloride, buprenorphine hydrochloride, butorphanol tartrate, codeine phosphate, codeine sulfate, fentanyl citrate, fentanyl transdermal system, fentanyl transmucosal, hydromorphone hydrochloride, meperidine hydrochloride, methadone hydrochloride, morphine hydrochloride, morphine sulfate, morphine tartrate, nalbuphine hydrochloride, oxycodone hydrochloride, oxycodone pectinate, oxymorphone hydrochloride, pentazocine hydrochloride, pentazocine hydrochloride and naloxone hydrochloride, pentazocine lactate, propoxyphene hydrochloride, propoxyphene napsylate, remifentanil hydrochloride, sufentanil citrate, and tramadol hydrochloride. The at least one sedative-hypnotic can be at least one selected from chloral hydrate, estazolam, flurazepam hydrochloride, pentobarbital, pentobarbital sodium, phenobarbital sodium, secobarbital sodium, temazepam, triazolam, zaleplon, and zolpidem tartrate. The at least one anticonvulsant can be at least one selected from acetazolamide sodium, carbamazepine, clonazepam, clorazepate dipotassium, diazepam, divalproex sodium, ethosuximde, fosphenyloin sodium, gabapentin, lamotrigine, magnesium sulfate, phenobarbital, phenobarbital sodium, phenyloin, phenyloin sodium, phenyloin sodium (extended), primidone, tiagabine hydrochloride, topiramate, valproate sodium, and valproic acid. The at least one antidepressant can be at least one selected from amitriptyline hydrochloride, amitriptyline pamoate, amoxapine, bupropion hydrochloride, citalopram hydrobromide, clomipramine hydrochloride, desipramine hydrochloride, doxepin hydrochloride, fluoxetine hydrochloride, imipramine hydrochloride, imipramine pamoate, mirtazapine, nefazodone hydrochloride, nortriptyline hydrochloride, paroxetine hydrochloride, phenelzine sulfate, sertraline hydrochloride, tranylcypromine sulfate, trimipramine maleate, and venlafaxine hydrochloride. The at least one antianxiety drug can be at least one selected from alprazolam, buspirone hydrochloride, chlordiazepoxide, chlordiazepoxide hydrochloride, clorazepate dipotassium, diazepam, doxepin hydrochloride, hydroxyzine embonate, hydroxyzine hydrochloride, hydroxyzine pamoate, lorazepam, mephrobamate, midazolam hydrochloride, and oxazepam. The at least one antipsychotic drug can be at least one selected from chlorpromazine hydrochloride, clozapine, fluphenazine decanoate, fluephenazine enanthate, fluphenazine hydrochloride, haloperidol, haloperidol decanoate, haloperidol lactate, loxapine hydrochloride, loxapine succinate, mesoridazine besylate, molindone hydrochloride, olanzapine, perphenazine, pimozide, prochlorperazine, quetiapine fumarate, risperidone, thioridazine hydrochloride, thiothixene, thiothixene hydrochloride, and trifluoperazine hydrochloride. The at least one central nervous system stimulant can be at least one selected from amphetamine sulfate, caffeine, dextroamphetamine sulfate, doxapram hydrochloride, methamphetamine hydrochloride, methylphenidate hydrochloride, modafinil, pemoline, and phentermine hydrochloride. The at least one antiparkinsonian can be at least one selected from amantadine hydrochloride, benztropine mesylate, biperiden hydrochloride, biperiden lactate, bromocriptine mesylate, carbidopa-levodopa, entacapone, levodopa, pergolide mesylate, pramipexole dihydrochloride, ropinirole hydrochloride, selegiline hydrochloride, tolcapone, and trihexyphenidyl hydrochloride. The at least one miscellaneous central nervous system drug can be at least one selected from bupropion hydrochloride, donepezil hydrochloride, droperidol, fluvoxamine maleate, lithium carbonate, lithium citrate, naratriptan hydrochloride, nicotine polacrilex, nicotine transdermal system, propofol, rizatriptan benzoate, sibutramine hydrochloride monohydrate, sumatriptan succinate, tacrine hydrochloride, and zolmitriptan. (See, e.g., pp. 337-530 of *Nursing* 2001 *Drug Handbook*.)

The at least one cholinergic (e.g., parasymathomimetic) can be at least one selected from bethanechol chloride, edrophonium chloride, neostigmine bromide, neostigmine methylsulfate, physostigmine salicylate, and pyridostigmine bromide. The at least one anticholinergic can be at least one selected from atropine sulfate, dicyclomine hydrochloride, glycopyrrolate, hyoscyamine, hyoscyamine sulfate, propantheline bromide, scopolamine, scopolamine butylbromide, and scopolamine hydrobromide. The at least one adrenergic (sympathomimetics) can be at least one selected from dobutamine hydrochloride, dopamine hydrochloride, metaraminol bitartrate, norepinephrine bitartrate, phenylephrine hydrochloride, pseudoephedrine hydrochloride, and pseudoephedrine sulfate. The at least one adrenergic blocker (sympatholytic) can be at least one selected from dihydroergotamine mesylate, ergotamine tartrate, methysergide maleate, and propranolol hydrochloride. The at least one skeletal muscle relaxant can be at least one selected from baclofen, carisoprodol, chlorzoxazone, cyclobenzaprine hydrochloride, dantrolene sodium, methocarbamol, and tizanidine hydrochloride. The at least one neuromuscular blocker can be at least one selected from atracurium besylate, cisatracurium besylate, doxacurium chloride, mivacurium chloride, pancuronium bromide, pipecuronium bromide, rapacuronium bromide, rocuronium bromide, succinylcholine chloride, tubocurarine chloride, and vecuronium bromide. (See, e.g., pp. 531-84 of *Nursing* 2001 *Drug Handbook*.)

The at least one antihistamine can be at least one selected from brompheniramine maleate, cetirizine hydrochloride, chlorpheniramine maleate, clemastine fumarate, cyproheptadine hydrochloride, diphenhydramine hydrochloride, fexofenadine hydrochloride, loratadine, promethazine hydrochloride, promethazine theoclate, and triprolidine hydrochloride. The at least one bronchodilator can be at least one selected from albuterol, albuterol sulfate, aminophylline, atropine sulfate, ephedrine sulfate, epinephrine, epinephrine bitartrate, epinephrine hydrochloride, ipratropium bromide, isoproterenol, isoproterenol hydrochloride, isoproterenol sulfate, levalbuterol hydrochloride, metaproterenol sulfate, oxtriphylline, pirbuterol acetate, salmeterol xinafoate, terbutaline sulfate, and theophylline. The at least one expectorant or antitussive can be at least one selected from benzonatate, codeine phosphate, codeine sulfate, dextramethorphan hydrobromide, diphenhydramine hydrochloride, guaifenesin, and hydromorphone hydrochloride. The at least one miscellaneous respiratory drug can be at least one selected from acetylcysteine, beclomethasone dipropionate, beractant, budesonide, calfactant, cromolyn sodium, domase alfa, epoprostenol sodium, flunisolide, fluticasone propionate, montelukast sodium, nedocromil sodium, palivizumab, triamcinolone acetonide, zafirlukast, and zileuton. (See, e.g., pp. 585-642 of *Nursing* 2001 *Drug Handbook*.)

The at least one antacid, adsorbent, or antiflatulent can be at least one selected from aluminum carbonate, aluminum hydroxide, calcium carbonate, magaldrate, magnesium hydroxide, magnesium oxide, simethicone, and sodium bicarbonate. The at least one digestive enzyme or gallstone solubilizer can be at least one selected from pancreatin, pancrelipase, and ursodiol. The at least one antidiarrheal can be at least one selected from attapulgite, bismuth subsalicylate, calcium polycarbophil, diphenoxylate hydrochloride and atropine sulfate, loperamide, octreotide acetate, opium tincture, and opium tincure (camphorated). The at least one laxative can be at least one selected from bisocodyl, calcium polycarbophil, cascara sagrada, cascara sagrada aromatic fluidextract, cascara sagrada fluidextract, castor oil, docusate calcium, docusate sodium, glycerin, lactulose, magnesium citrate, magnesium hydroxide, magnesium sulfate, methylcellulose, mineral oil, polyethylene glycol or electrolyte solution, psyllium, senna, and sodium phosphates. The at least one antiemetic can be at least one selected from chlorpromazine hydrochloride, dimenhydrinate, dolasetron mesylate, dronabinol, granisetron hydrochloride, meclizine hydrochloride, metoclopromaide hydrochloride, ondansetron hydrochloride, perphenazine, prochlorperazine, prochlorperazine edisylate, prochlorperazine maleate, promethazine hydrochloride, scopolamine, thiethylperazine maleate, and trimethobenzamide hydrochloride. The at least one antiulcer drug can be at least one selected from cimetidine, cimetidine hydrochloride, famotidine, lansoprazole, misoprostol, nizatidine, omeprazole, rabeprozole sodium, rantidine bismuth citrate, ranitidine hydrochloride, and sucralfate. (See, e.g., pp. 643-95 of *Nursing* 2001 *Drug Handbook*.)

The at least one coricosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcino lone, triamcino lone acetonide, and triamcino lone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system. The at least one estrogen or progestin can be at least one selected from esterified estrogens, estradiol, estradiol cypionate, estradiol/norethindrone acetate transdermal system, estradiol valerate, estrogens (conjugated), estropipate, ethinyl estradiol, ethinyl estradiol and desogestrel, ethinyl estradiol and ethynodiol diacetate, ethinyl estradiol and desogestrel, ethinyl estradiol and ethynodiol diacetate, ethinyl estradiol and levonorgestrel, ethinyl estradiol and norethindrone, ethinyl estradiol and norethindrone acetate, ethinyl estradiol and norgestimate, ethinyl estradiol and norgestrel, ethinyl estradiol and norethindrone and acetate and ferrous fumarate, levonorgestrel, medroxyprogesterone acetate, mestranol and norethindron, norethindrone, norethindrone acetate, norgestrel, and progesterone. The at least one gonadroptropin can be at least one selected from ganirelix acetate, gonadoreline acetate, histrelin acetate, and menotropins. The at least one antidiabetic or glucaon can be at least one selected from acarbose, chlorpropamide, glimepiride, glipizide, glucagon, glyburide, insulins, metformin hydrochloride, miglitol, pioglitazone hydrochloride, repaglinide, rosiglitazone maleate, and troglitazone. The at least one thyroid hormone can be at least one selected from levothyroxine sodium, liothyronine sodium, liotrix, and thyroid. The at least one thyroid hormone antagonist can be at least one selected from methimazole, potassium iodide, potassium iodide (saturated solution), propylthiouracil, radioactive iodine (sodium iodide $^{131}$I), and strong iodine solution. The at least one pituitary hormone can be at least one selected from corticotropin, cosyntropin, desmophressin acetate, leuprolide acetate, repository corticotropin, somatrem, somatropin, and vasopressin. The at least one parathyroid-like drug can be at least one selected from calcifediol, calcitonin (human), calcitonin (salmon), calcitriol, dihydrotachysterol, and etidronate disodium. (See, e.g., pp. 696-796 of Nursing 2001 Drug Handbook.)

The at least one diuretic can be at least one selected from acetazolamide, acetazolamide sodium, amiloride hydrochloride, bumetanide, chlorthalidone, ethacrynate sodium, ethacrynic acid, furosemide, hydrochlorothiazide, indapamide, mannitol, metolazone, spironolactone, torsemide, triamterene, and urea. The at least one electrolyte or replacement solution can be at least one selected from calcium acetate, calcium carbonate, calcium chloride, calcium citrate, calcium glubionate, calcium gluceptate, calcium gluconate, calcium lactate, calcium phosphate (dibasic), calcium phosphate (tribasic), dextran (high-molecular-weight), dextran (low-molecular-weight), hetastarch, magnesium chloride, magnesium sulfate, potassium acetate, potassium bicarbonate, potassium chloride, potassium gluconate, Ringer's injection, Ringer's injection (lactated), and sodium chloride. The at least one acidifier or alkalinizer can be at least one selected from sodium bicarbonate, sodium lactate, and tromethamine. (See, e.g., pp. 797-833 of Nursing 2001 Drug Handbook.)

The at least one hematinic can be at least one selected from ferrous fumarate, ferrous gluconate, ferrous sulfate, ferrous sulfate (dried), iron dextran, iron sorbitol, polysaccharide-iron complex, and sodium ferric gluconate complex. The at least one anticoagulant can be at least one selected from ardeparin sodium, dalteparin sodium, danaparoid sodium, enoxaparin sodium, heparin calcium, heparin sodium, and warfarin sodium. The at least one blood derivative can be at least one selected from albumin 5%, albumin 25%, antihemophilic factor, anti-inhibitor coagulant complex, antithrombin III (human), factor IX (human), factor IX complex, and plasma protein fractions. The at least one thrombolytic enzyme can be at least one selected from alteplase, anistreplase, reteplase (recombinant), streptokinase, and urokinase. (See, e.g., pp. 834-66 of Nursing 2001 Drug Handbook.)

The at least one alkylating drug can be at least one selected from busulfan, carboplatin, carmustine, chlorambucil, cisplatin, cyclophosphamide, ifosfamide, lomustine, mechlorethamine hydrochloride, melphalan, melphalan hydrochloride, streptozocin, temozolomide, and thiotepa. The at least one antimetabolite can be at least one selected from capecitabine, cladribine, cytarabine, floxuridine, fludarabine phosphate, fluorouracil, hydroxyurea, mercaptopurine, methotrexate, methotrexate sodium, and thioguanine. The at least one antibiotic antineoplastic can be at least one selected from bleomycin sulfate, dactinomycin, daunorubicin citrate liposomal, daunorubicin hydrochloride, doxorubicin hydrochloride, doxorubicin hydrochloride liposomal, epirubicin hydrochloride, idarubicin hydrochloride, mitomycin, pentostatin, plicamycin, and valrubicin. The at least one antineoplastic that alters hormone balance can be at least one selected from anastrozole, bicalutamide, estramustine phosphate sodium, exemestane, flutamide, goserelin acetate, letrozole, leuprolide acetate, megestrol acetate, nilutamide, tamoxifen citrate, testolactone, and toremifene citrate. The at least one miscellaneous antineoplastic can be at least one selected from asparaginase, *bacillus Calmette-Guerin* (BCG) (live intravesical), dacarbazine, docetaxel, etoposide, etoposide phosphate, gemcitabine hydrochloride, irinotecan hydrochloride, mitotane, mitoxantrone hydrochloride, paclitaxel, pegaspargase, porfimer sodium, procarbazine hydrochloride, rituximab, teniposide, topotecan hydrochloride, trastuzumab, tretinoin, vinblastine sulfate, vincristine sulfate, and vinorelbine tartrate. (See, e.g., pp. 867-963 of Nursing 2001 Drug Handbook.)

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus. The at least one vaccine or toxoid can be at least one selected from BCG vaccine, cholera vaccine, diphtheria and tetanus toxoids (adsorbed), diphtheria and tetanus toxoids and acellular pertussis vaccine adsorbed, diphtheria and tetanus toxoids and whole-cell pertussis vaccine, *Haemophilus* b conjugate vaccines, hepatitis A vaccine (inactivated), hepatitis B vaccine (recombinant), influenza virus vaccine 1999-2000 trivalent types A & B (purified surface antigen), influenza virus vaccine 1999-2000 trivalent types A & B (subvirion or purified subvirion), influenza virus vaccine 1999-2000 trivalent types A & B (whole virion), Japanese encephalitis virus vaccine (inactivated), Lyme disease vaccine (recombinant OspA), measles and mumps and rubella virus vaccine (live), measles and mumps and rubella virus vaccine (live attenuated), measles virus vaccine (live attenuated), meningococcal polysaccharide vaccine, mumps virus vaccine (live), plague vaccine, pneumococcal vaccine (polyvalent), poliovirus vaccine (inactivated), poliovirus vaccine (live, oral, trivalent), rabies vaccine (adsorbed), rabies vaccine (human diploid cell), rubella and mumps virus vaccine (live), rubella virus vaccine (live, attenuated), tetanus toxoid (adsorbed), tetanus toxoid (fluid), typhoid vaccine (oral), typhoid vaccine (parenteral), typhoid Vi polysaccharide vaccine, varicella virus vaccine, and yellow fever vaccine. The at least one antitoxin or antivenin can be at least one selected from black widow spider antivenin, Crotalidae antivenom (polyvalent), diphtheria antitoxin (equine), and *Micrurus fulvius* antivenin. The at least one immune serum can be at least one selected from cytomegalovirus immune globulin (intraveneous), hepatitis B immune globulin (human), immune globulin intramuscular, immune globulin intravenous, rabies immune globulin (human), respiratory syncytial virus immune globulin intravenous (human), Rh$_0$(D) immune globulin (human), Rh$_0$(D) immune globulin intravenous (human), tetanus immune globulin (human), and varicella-zoster immune globulin. The at least one biological response modifier can be at least one selected from aldesleukin, epoetin alfa, filgrastim, glatiramer acetate for injection, interferon alfacon-1, interferon alfa-2a (recombinant), interferon alfa-2b (recombinant), interferon beta-1a, interferon beta-1b (recombinant), interferon gamma-1b, levamisole hydrochloride, oprelvekin, and sargramostim. (See, e.g., pp. 964-1040 of *Nursing* 2001 *Drug Handbook.*)

The at least one ophthalmic anti-infective can be selected form bacitracin, chloramphenicol, ciprofloxacin hydrochloride, erythromycin, gentamicin sulfate, ofloxacin 0.3%, polymyxin B sulfate, sulfacetamide sodium 10%, sulfacetamide sodium 15%, sulfacetamide sodium 30%, tobramycin, and vidarabine. The at least one ophthalmic anti-inflammatory can be at least one selected from dexamethasone, dexamethasone sodium phosphate, diclofenac sodium 0.1%, fluorometholone, flurbiprofen sodium, ketorolac tromethamine, prednisolone acetate (suspension) and prednisolone sodium phosphate (solution). The at least one miotic can be at least one selected from acetylocholine chloride, carbachol (intraocular), carbachol (topical), echothiophate iodide, pilocarpine, pilocarpine hydrochloride, and pilocarpine nitrate. The at least one mydriatic can be at least one selected from atropine sulfate, cyclopentolate hydrochloride, epinephrine hydrochloride, epinephryl borate, homatropine hydrobromide, phenylephrine hydrochloride, scopolamine hydrobromide, and tropicamide. The at least one ophthalmic vasoconstrictor can be at least one selected from naphazoline hydrochloride, oxymetazoline hydrochloride, and tetrahydrozoline hydrochloride. The at least one miscellaneous ophthalmic can be at least one selected from apraclonidine hydrochloride, betaxolol hydrochloride, brimonidine tartrate, carteolol hydrochloride, dipivefrin hydrochloride, dorzolamide hydrochloride, emedastine difumarate, fluorescein sodium, ketotifen fumarate, latanoprost, levobunolol hydrochloride, metipranolol hydrochloride, sodium chloride (hypertonic), and timolol maleate. The at least one otic can be at least one selected from boric acid, carbamide peroxide, chloramphenicol, and triethanolamine polypeptide oleate-condensate. The at least one nasal drug can be at least one selected from beclomethasone dipropionate, budesonide, ephedrine sulfate, epinephrine hydrochloride, flunisolide, fluticasone propionate, naphazoline hydrochloride, oxymetazoline hydrochloride, phenylephrine hydrochloride, tetrahydrozoline hydrochloride, triamcinolone acetonide, and xylometazoline hydrochloride. (See, e.g., pp. 1041-97 of *Nursing* 2001 *Drug Handbook.*)

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of *Nursing* 2001 *Drug Handbook.*)

The at least one vitamin or mineral can be at least one selected from vitamin A, vitamin B complex, cyanocobalamin, folic acid, hydroxocobalamin, leucovorin calcium, niacin, niacinamide, pyridoxine hydrochloride, riboflavin, thiamine hydrochloride, vitamin C, vitamin D, cholecalciferol, ergocalciferol, vitamin D analogue, doxercalciferol, paricalcitol, vitamin E, vitamin K analogue, phytonadione, sodium fluoride, sodium fluoride (topical), trace elements, chromium, copper, iodine, manganese, selenium, and zinc. The at least one caloric can be at least one selected from amino acid infusions (crystalline), amino acid infusions in dextrose, amino acid infusions with electrolytes, amino acid infusions with electrolytes in dextrose, amino acid infusions for hepatic failure, amino acid infusions for high metabolic stress, amino acid infusions for renal failure, dextrose, fat emulsions, and medium-chain triglycerides. (See, e.g., pp. 1137-63 of *Nursing* 2001 *Drug Handbook.*)

IL-23 Ig Derived Protein or Specified Portion or Variant Compositions

The present invention also provides at least one IL-23 Ig derived protein or specified portion or variant composition comprising at least one, at least two, at least three, at least four, at least five, at least six or more IL-23 Ig derived proteins or specified portions or variants thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the IL-23 Ig derived protein amino acid sequence, or specified fragments, domains or variants thereof. Such composition percentages are by weight, volume, concentration, molarity, or molality as liquid or dry solutions, mixtures, suspension, emulsions or colloids, as known in the art or as described herein.

IL-23 Ig derived protein or specified portion or variant compositions of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences*, 18th Edition, Mack Publishing Co. (Easton, Pa.) 1990. Pharmaceutically acceptable carriers can be routinely selected that are suitable for the mode of administration, solubility and/or stability of the IL-23 composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/Ig derived protein or specified portion or variant components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

IL-23 Ig derived protein compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, the IL-23 Ig derived protein or specified portion or variant compositions of the invention can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the IL-23 Ig protein compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

Formulations

As noted above, the invention provides for stable formulations, which comprise preferably a phosphate buffer with saline or a chosen salt, as well as preserved solutions and formulations containing a preservative, as well as multi-use preserved formulations suitable for pharmaceutical or veterinary use, comprising at least one IL-23 Ig derived protein or specified portion or variant in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1., 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one IL-23 Ig derived protein or specified portion or variant with the prescribed buffers and/or preservatives, optionally, in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising in lyophilized form at least one IL-23 Ig derived protein or specified portion or variant, and a second vial comprising an aqueous diluent of prescribed buffer or preservative, wherein said packaging material comprises a label that instructs a patient to reconstitute the at least one IL-23 Ig derived protein or specified portion or variant in the aqueous diluent to form a solution that can be held over a period of twenty-four hours or greater.

The at least one IL-23 Ig derived protein or specified portion or variant used in accordance with the present invention can be produced by recombinant means, including from mammalian cell or transgenic preparations, or can be purified from other biological sources, as described herein or as known in the art.

The range of at least one IL-23 Ig derived protein or specified portion or variant in the product of the present invention includes amounts yielding upon reconstitution, if in a wet/dry system, concentrations from about 1.0 pg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyls, other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one IL-23 Ig derived protein or specified portion or variant and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one IL-23 Ig derived protein or specified portion or variant and preservative in an aqueous diluent is carried out using conventional dissolution and mixing procedures. To prepare a suitable formulation, for example, a measured amount of at least one IL-23 Ig derived protein or specified portion or variant in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that may be optimized for the concentration and means of administration used.

The claimed formulations can be provided to patients as clear solutions or as dual vials comprising a vial of lyophilized, at least one IL-23 Ig derived protein or specified portion or variant that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period ranging from immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one IL-23 Ig derived protein or specified portion or variant in the invention can be prepared by a process that comprises mixing at least one Ig derived protein or specified portion or variant in an aqueous diluent. Mixing is carried out using conventional dissolution and mixing procedures. To prepare a suitable diluent, for example, a measured amount of at least one Ig derived protein or specified portion or variant in water or buffer is combined in quantities sufficient to provide the protein and, optionally, a preservative or buffer at the desired concentrations. Variations of this process would be recognized by one of ordinary skill in the art. For example, the order in which the components are added, whether additional additives are used, the temperature and pH at which the formulation is prepared, are all factors that may be optimized for the concentration and means of administration used.

The claimed products can be provided to patients as clear solutions or as dual vials comprising a vial of lyophilized, at least one IL-23 Ig derived protein or specified portion or variant that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized, at least one IL-23 Ig derived protein or specified portion or variant that is reconstituted with a second vial containing the aqueous diluent. The clear solution in this case can be up to one liter or even larger in size, providing a large reservoir from which smaller portions of the at least one Ig derived protein or specified portion or variant solution can be retrieved one or multiple times for transfer into smaller vials and provided by the pharmacy or clinic to their customers and/or patients.

Recognized devices comprising these single vial systems include those pen-injector devices for delivery of a solution, such as BD Pens, BD Autojecto®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free injector®, Intraject®, Medi-Ject®, e.g., as made or developed by Becton Dickenson (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com). Recognized devices comprising a dual vial system include those pen-injector systems for reconstituting a lyophilized drug in a cartridge for delivery of the reconstituted solution, such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one IL-23 Ig derived protein or specified portion or variant in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one IL-23 Ig derived protein or specified portion or variant and a selected buffer, preferably, a phosphate buffer containing saline or a chosen salt. Mixing the at least one Ig derived protein or specified portion or variant and buffer in an aqueous diluent is carried out using conventional dissolution and mixing procedures. To prepare a suitable formulation, for example, a measured amount of at least one Ig derived protein or specified portion or variant in water or buffer is combined with the desired buffering agent in water in quantities sufficient to provide the protein and buffer at the desired concentrations. Variations of this process would be recognized by one of ordinary skill in the art. For example, the order in which the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized, at least one IL-23 Ig derived protein or specified portion or variant that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one IL-23 Ig derived protein or specified portion or variant in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating IL-23 conditions or diseases, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalmic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to, asthenia, anemia, cachexia, and the like), chronic salicylate intoxication, acute or chronic bacterial infection, acute and chronic parasitic or infectious processes, including bacterial, viral and fungal infections, HIV infection/HIV neuropathy, meningitis, hepatitis (e.g., A, B or C, or the like), septic arthritis, peritonitis, pneumonia, epiglottitis, *e. Coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium* intracellulare, *pneumocystis carinii* pneumonia, pelvic inflammatory disease, orchitis/epidymitis, *legionella*, lyme disease, influenza a, epstein-barr virus, vital-associated hemaphagocytic syndrome, vital encephalitis/aseptic meningitis, neurodegenerative diseases, multiple sclerosis, migraine headache, AIDS dementia complex, demyelinating diseases, such as multiple sclerosis and acute transverse myelitis; extrapyramidal and cerebellar disorders, such as lesions of the corticospinal system; disorders of the basal ganglia or cerebellar disorders; hyperkinetic movement disorders, such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi-system disorder); demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, neurotraumatic injury (e.g., but not limited to, spinal cord injury, brain injury, concussion, and repetitive concussion), pain, inflammatory pain, autism, depression, stroke, cognitive disorders, epilepsy, and the like. Such a method can optionally comprise administering an effective amount of at least one composition or pharmaceutical composition comprising at least one IL-23 Ig derived protein or specified portion or variant to a cell, tissue, organ, animal or patient in need of such modulation, treatment or therapy.

Any method of the present invention can comprise administering an effective amount of a composition or pharmaceutical composition comprising at least one IL-23 Ig derived protein or specified portion or variant to a cell, tissue, organ, animal or patient in need of such modulation, treatment or therapy. Such a method can optionally further comprise co-administration or combination therapy for treating such immune diseases, wherein the administering of said at least one IL-23 Ig derived protein, specified portion or variant thereof, further comprises administering, before, concurrently, and/or after, at least one selected from at least one multiple sclerosis therapeutic (including but not limited to, beta-interferon 1a and beta-interferon 1b (e.g., Avonex™, RebifrM™, Betaseon™), glutiramer acetate (e.g., Copaxone), cyclophasphamide, azathioprine, glucocorticosteroids, methotrexate, Paclitaxel, 2-chlorodeoxyadenosine, mitoxantrone, IL-10, TGBb, CD4, CD52, antegren, CD11, CD18, TNFalpha, IL-1, IL-2, and/or CD4 antibody or antibody receptor fusion, interferon alpha, immunoglobulin, Lismide (Requinimax™), insulin-like growth factor-1 (IGF-1), elprodil, pirfenidone, oral myelin, or compounds that act on one or more of at least one of: autoimmune suppression of myelin destruction, immune regulation, activation, proliferation, migration and/or suppressor cell function of T-cells, inhibition of T cell receptor/peptide/MHC-11 interaction, induction of T cell anergy, deletion of autoreactive T cells, reduction of trafficking across blood brain barrier, alteration of balance of pro-inflammatory (Th1) and immunomodulatory (Th2) cytokines, inhibition of matrix metalloprotease inhibitors, neuroprotection, reduction of gliosis, promotion of re-myelination), TNF antagonist (e.g., but not limited to a TNF Ig derived protein or fragment, a soluble TNF receptor or fragment, fusion proteins thereof, or a small molecule TNF antagonist), an antirheumatic, a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, an IL-23 agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

TNF antagonists suitable for compositions, combination therapy, co-administration, devices and/or methods of the present invention (further comprising at least one antibody, specified portion and variant thereof, of the present invention), include, but are not limited to, anti-TNF Ig derived proteins, antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor Ig derived protein," "TNF Ig derived protein," "TNFα Ig derived protein," or fragment and the like decreases, blocks, inhibits, abrogates or interferes with TNFα activity in vitro, in situ and/or preferably in vivo. For example, a suitable TNF human Ig derived protein of the present invention can bind TNFα and includes anti-TNF Ig derived proteins, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

Chimeric Ig derived protein cA2 consists of the antigen binding variable region of the high-affinity neutralizing mouse anti-human TNFα IgG 1 Ig derived protein, designated A2, and the constant regions of a human IgG1, kappa immunoglobulin. The human IgG1 Fc region improves allogeneic Ig derived protein effector function, increases the circulating serum half-life and decreases the immunogenicity of the Ig derived protein. The avidity and epitope specificity of the chimeric Ig derived protein cA2 is derived from the variable region of the murine Ig derived protein A2. In a particular embodiment, a preferred source for nucleic acids encoding the variable region of the murine Ig derived protein A2 is the A2 hybridoma cell line.

Chimeric A2 (cA2) neutralizes the cytotoxic effect of both natural and recombinant human TNFα in a dose dependent manner. From binding assays of chimeric Ig derived protein cA2 and recombinant human TNFα, the affinity constant of chimeric Ig derived protein cA2 was calculated to be $1.04 \times 10^{10} M^{-1}$. Preferred methods for determining monoclonal Ig derived protein specificity and affinity by competitive inhibition can be found in Harlow, et al., *Ig derived proteins: A Laboratory Manual*, Cold Spring Harbor Laboratory Press, Cold Spring Harbor, N.Y., 1988; Colligan et al., eds., *Current Protocols in Immunology*, Greene Publishing Assoc. and Wiley Interscience, New York, (1992-2003); Kozbor et al., *Immunol. Today*, 4:72-79 (1983); Ausubel et al., eds. *Current Protocols in Molecular Biology*, Wiley Interscience, New York (1987-2003); and Muller, *Meth. Enzymol.*, 92:589-601 (1983), which references are entirely incorporated herein by reference.

In a particular embodiment, murine monoclonal Ig derived protein A2 is produced by a cell line designated c134A. Chimeric Ig derived protein cA2 is produced by a cell line designated c168A.

Additional examples of monoclonal anti-TNF Ig derived proteins that can be used in the present invention are described in the art (see, e.g., U.S. Pat. No. 5,231,024; Möller, A. et al., *Cytokine* 2(3):162-169 (1990); U.S. application Ser. No. 07/943,852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); and Hirai, et al., *J. Immunol. Meth.* 96:57-62 (1987), which references are entirely incorporated herein by reference).

TNF Receptor Molecules

Preferred TNF receptor molecules useful in the present invention are those that bind TNFα with high affinity (see, e.g., Feldmann et al., International Publication No. WO 92/07076 (published Apr. 30, 1992); Schall et al., *Cell* 61:361-370 (1990); and Loetscher et al., *Cell* 61:351-359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., *Eur. J. Biochem.* 223:831-840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., *J. Biol. Chem.* 265:1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterized by their ability to treat patients for extended periods with good to excellent alleviation of symptoms and low toxicity. Low immunogenicity and/or high affinity, as well as other undefined properties, may contribute to the therapeutic results achieved.

TNF receptor multimeric molecules useful in the present invention comprise all or a functional portion of the ECD of two or more TNF receptors linked via one or more polypeptide linkers or other nonpeptide linkers, such as polyethylene glycol (PEG). The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539 (1991); Peppel et al., *J. Exp. Med.* 174:1483-1489 (1991); Kolls et al., *Proc. Natl. Acad. Sci. USA* 91:215-219 (1994); Butler et al., *Cytokine* 6(6):616-623 (1994); Baker et al., *Eur. J. Immunol.* 24:2040-2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116,964; Capon et al., U.S. Pat. No. 5,225,538; and Capon et al., *Nature* 337:525-531 (1989), which references are entirely incorporated herein by reference.

A functional equivalent, derivative, fragment or region of TNF receptor molecule refers to the portion of the TNF receptor molecule, or the portion of the TNF receptor molecule sequence which encodes TNF receptor molecule, that is of sufficient size and sequences to functionally resemble TNF receptor molecules that can be used in the present invention (e.g., bind TNFα with high affinity and possess low immunogenicity). A functional equivalent of TNF receptor molecule also includes modified TNF receptor molecules that functionally resemble TNF receptor molecules that can be used in the present invention (e.g., bind TNFα with high affinity and possess low immunogenicity). For example, a functional equivalent of TNF receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., *Current Protocols in Molecular Biology*, Greene Publishing Assoc. and Wiley-Interscience, New York (1987-2003).

Cytokines include any known cytokine. See, e.g., CopewithCytokines.com. Cytokine antagonists include, but are not limited to, any Ig derived protein, fragment or mimetic, any soluble receptor, fragment or mimetic, any small molecule antagonist, or any combination thereof.

Therapeutic Treatments

Any method of the present invention can comprise a method for treating a IL-23 mediated disorder, comprising administering an effective amount of a composition or pharmaceutical composition comprising at least one IL-23 Ig derived protein or specified portion or variant to a cell, tissue, organ, animal or patient in need of such modulation, treatment or therapy.

Typically, treatment of pathologic conditions is effected by administering an effective amount or dosage of at least one IL-23 Ig related protein composition that total, on average, a range from at least about 0.01 to 500 milligrams of at least one IL-23 Ig derived protein or specified portion or variant/kilogram of patient per dose, and, preferably, from at least about 0.1 to 100 milligrams of Ig derived protein or specified portion or variant/kilogram of patient per single or multiple administration, depending upon the specific activity of contained in the composition. Alternatively, the effective serum concentration can comprise 0.1-5000 μg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually, a dosage of active ingredient can be about 0.1 to 100 milligrams per kilogram of body weight. Ordinarily, 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one Ig derived protein or specified portion or variant of the present invention, 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or, alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or, alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions, the active ingredient will ordinarily be present in an amount of about 0.5-99.999% by weight based on the total weight of the composition.

For parenteral administration, the Ig derived protein or specified portion or variant can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles, such as fixed oils, may also be used. The vehicle or lyophilized powder may contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of at least one IL-23 Ig derived protein or specified portion or variant according to the present invention. While pulmonary administration is used in the following description, other modes of administration can be used according to the present invention with suitable results.

IL-23 Ig derived proteins of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides. Parenteral administration is known in the art and includes, but is not limited to, conventional means of injections, a gas pressured needle-less injection device as described in U.S. Pat. No. 5,851,198, and a laser perforator device as described in U.S. Pat. No. 5,839,446, entirely incorporated herein by reference.

Alternative Delivery

The invention further relates to the administration of at least one IL-23 Ig derived protein or specified portion or variant by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. An anti-IL-23 Ig derived protein or specified portion or variant compositions can be prepared for use for parenteral (subcutaneous, intramuscular, intravenous, intrarticular, etc.) administration particularly in the form of liquid solutions or suspensions; for use in vaginal or rectal administration particularly in semisolid forms, such as creams and suppositories; for buccal, or sublingual administration particularly in the form of tablets or capsules; or intranasally particularly in the form of powders, nasal drops or aerosols or certain agents; or transdermally particularly in the form of a gel, ointment, lotion, suspension or patch delivery system with chemical enhancers, such as dimethyl sulfoxide, to either modify the skin structure or to increase the drug concentration in the transdermal patch (Junginger, et al. In "Drug Permeation Enhancement"; Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin such as iontophoresis, or application of ultrasound, such as sonophoresis (U.S. Pat. Nos. 4,309,989 and 4,767,402) (the above publications and patents being entirely incorporated herein by reference).

Pulmonary/Nasal Administration

For pulmonary administration, preferably, at least one IL-23 Ig derived protein or specified portion or variant composition is delivered in a particle size effective for reaching the lower airways of the lung or sinuses. According to the invention, at least one IL-23 Ig derived protein or specified portion or variant can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of Ig derived protein or specified portion or variants are also known in the art. All such devices can use formulations suitable for the administration for the dispensing of Ig derived protein or specified portion or variant in an aerosol. Such aerosols can be comprised of either solutions (both aqueous and non aqueous) or solid particles. Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be representative of specific devices suitable for the practice of this invention, and are not intended as limiting the scope of the invention. Preferably, a composition comprising at least one IL-23 Ig derived protein or specified portion or variant is delivered by a dry powder inhaler or a sprayer. There are several desirable features of an inhalation device for administering at least one Ig derived protein or specified portion or variant of the present invention. For example, delivery by the inhalation device is advantageously reliable, reproducible, and accurate. The inhalation device can optionally deliver small dry particles, e.g. less than about 10 μm, preferably about 1-5 μm, for good respirability.

Administration of IL-23 Ig Derived Protein or Specified Portion or Variant Compositions as a Spray A spray including IL-23 Ig derived protein or specified portion or variant composition can be produced by forcing a suspension or solution of at least one IL-23 Ig derived protein or specified portion or variant through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one IL-23 Ig derived protein or specified portion or variant composition protein delivered by a sprayer have a particle size less than about 10 μm, preferably, in the range of about 1 μm to about 5 μm, and, most preferably, about 2 μm to about 3 μm.

Formulations of at least one IL-23 Ig derived protein or specified portion or variant composition protein suitable for use with a sprayer typically include Ig derived protein or specified portion or variant composition protein in an aqueous solution at a concentration of about 0.1 mg to about 100 mg of at least one IL-23 Ig derived protein or specified portion or variant composition protein per ml of solution or mg/gm, or any range or value therein, e.g., but not lmited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents, such as an excipient, a buffer, an isotonicity agent, a preservative, a surfactant, and, preferably, zinc. The formulation can also include an excipient or agent for stabilization of the Ig derived protein or specified portion or variant composition protein, such as a buffer, a reducing agent, a bulk protein, or a carbohydrate. Bulk proteins useful in formulating Ig derived protein or specified portion or variant composition proteins include albumin, protamine, or the like. Typical carbohydrates useful in formulating Ig derived protein or specified portion or variant composition proteins include sucrose, mannitol, lactose, trehalose, glucose, or the like. The Ig derived protein or specified portion or variant composition protein formulation can also include a surfactant, which can reduce or prevent surface-induced aggregation of the Ig derived protein or specified portion or variant composition protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation.

Especially preferred surfactants for purposes of this invention are polyoxyethylene sorbitan monooleate, polysorbate 80, polysorbate 20, or the like. Additional agents known in the art for formulation of a protein, such as an IL-23 Ig derived proteins or specified portions or variants, can also be included in the formulation.

Administration of IL-23 Ig Derived Protein or Specified Portion or Variant Compositions by a Nebulizer Ig derived protein or specified portion or variant composition can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of Ig derived protein or specified portion or variant composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of Ig derived protein or specified portion or variant composition protein either directly or through a coupling fluid, creating an aerosol including the Ig derived protein or specified portion or variant composition protein. Advantageously, particles of Ig derived protein or specified portion or variant composition protein delivered by a nebulizer have a particle size less than about 10 µm, preferably, in the range of about 1 µm to about 5 µm, and, most preferably, about 2 µm to about 3 µm.

Formulations of at least one IL-23 Ig derived protein or specified portion or variant suitable for use with a nebulizer, either jet or ultrasonic, typically include a concentration of about 0.1 mg to about 100 mg of at least one IL-23 Ig derived protein or specified portion or variant protein per ml of solution. The formulation can include agents, such as an excipient, a buffer, an isotonicity agent, a preservative, a surfactant, and, preferably, zinc. The formulation can also include an excipient or agent for stabilization of the at least one IL-23 Ig derived protein or specified portion or variant composition protein, such as a buffer, a reducing agent, a bulk protein, or a carbohydrate. Bulk proteins useful in formulating at least one IL-23 Ig derived protein or specified portion or variant composition proteins include albumin, protamine, or the like. Typical carbohydrates useful in formulating at least one IL-23 Ig derived protein or specified portion or variant include sucrose, mannitol, lactose, trehalose, glucose, or the like. The at least one IL-23 Ig derived protein or specified portion or variant formulation can also include a surfactant, which can reduce or prevent surface-induced aggregation of the at least one IL-23 Ig derived protein or specified portion or variant caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as Ig derived protein or specified portion or variant protein can also be included in the formulation.

Administration of IL-23 Ig Derived Protein or Specified Portion or Variant Compositions by a Metered Dose Inhaler In a metered dose inhaler (MDI), a propellant, at least one IL-23 Ig derived protein or specified portion or variant, and any excipients or other additives are contained in a canister as a mixture including a liquefied compressed gas. Actuation of the metering valve releases the mixture as an aerosol, preferably, containing particles in the size range of less than about 10 µm, preferably, about 1 µm to about 5 µm, and, most preferably, about 2 µm to about 3 µm. The desired aerosol particle size can be obtained by employing a formulation of Ig derived protein or specified portion or variant composition produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one IL-23 Ig derived protein or specified portion or variant for use with a metered-dose inhaler device will generally include a finely divided powder containing at least one IL-23 Ig derived protein or specified portion or variant as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. Preferably, the propellant is a hydrofluorocarbon. The surfactant can be chosen to stabilize the at least one IL-23 Ig derived protein or specified portion or variant as a suspension in the propellant, to protect the active agent against chemical degradation, and the like. Suitable surfactants include sorbitan trioleate, soya lecithin, oleic acid, or the like. In some cases solution aerosols are preferred using solvents, such as ethanol. Additional agents known in the art for formulation of a protein can also be included in the formulation.

One of ordinary skill in the art will recognize that the methods of the current invention can be achieved by pulmonary administration of at least one IL-23 Ig derived protein or specified portion or variant compositions via devices not described herein.

Oral Formulations and Administration

Formulations for oral administration rely on the co-administration of adjuvants (e.g., resorcinols and nonionic surfactants, such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant, such as magnesium stearate, paraben, preserving agent, such as sorbic acid, ascorbic acid, .alpha.-tocopherol, antioxidant, such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations may contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925, 673). Furthermore, carrier compounds described in U.S. Pat. No. 5,879,681 and U.S. Pat. No. 5,871,753 are used to deliver biologically active agents orally and are known in the art.

Mucosal Formulations and Administration

For absorption through mucosal surfaces, compositions and methods of administering at least one IL-23 Ig derived protein or specified portion or variant include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration, excipients include sugars, calcium stearate, magnesium stearate, pregelinatined starch, and the like (U.S. Pat. No. 5,849,695).

Transdermal Formulations and Administration

For transdermal administration, the at least one IL-23 Ig derived protein or specified portion or variant is encapsulated in a delivery device, such as a liposome or polymeric nanoparticles, microparticle, microcapsule, or microspheres (referred to collectively as microparticles unless otherwise stated). A number of suitable devices are known, including microparticles made of synthetic polymers, such as polyhydroxy acids, such as polylactic acid, polyglycolic acid and copolymers thereof, polyorthoesters, polyanhydrides, and polyphosphazenes, and natural polymers, such as collagen, polyamino acids, albumin and other proteins, alginate and other polysaccharides, and combinations thereof (U.S. Pat. Nos. 5,814,599).

Prolonged Administration and Formulations

It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid, such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation, such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g., a zinc tannate salt. Additionally, the compounds of the present invention or, preferably, a relatively insoluble salt, such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulation in a slow degrading, non-toxic, non-antigenic polymer, such as a polylactic acid/polyglycolic acid polymer, for example, as described in U.S. Pat. No. 3,773,919. The compounds or, preferably, relatively insoluble salts, such as those described above, can also be formulated in cholesterol matrix silastic pellets, particularly for use in animals. Additional slow release, depot or implant formulations, e.g., gas or liquid liposomes, are known in the literature (U.S. Pat. No. 5,770, 222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

EXAMPLES OF THE INVENTION

Example 1

Generation, Cloning and Expression of an Anti-IL-23 Immunoglobulin Derived Protein in Mammalian Cells Anti-IL-23 Ig derived proteins are generated using known methods, such as murine or transgenic mice expressing human antibodies that are immunized with human IL-23, and for which B cells are isolated, cloned and selected for specificity and inhibiting activity for IL-23 (preferably with little or no inhibition of IL-12 activity) using known methods and assays, e.g., as known in the art and as described herein (see, e.g., www.copewithcytokines.de, under IL-23 and IL-12, for description and references to IL-23 proteins, IL-23 assays and IL-12 assays, entirely incorporated herein by reference, as known in the art). Alternatively, portions of the IL-12 beta 1 receptor are cloned and fused with antibody fragments to generate receptor fusion proteins that block binding of IL-23 to its receptors but which do not inhibit binding of IL-12 to its receptors, as known in the art.

Clones expressing IL-23 specific antibodies or fusion proteins, such as the anti-IL-23 Ig derived proteins of the present invention are selected so that they neutralize or inhibit at least one IL-23 activity and which do not substantially inhibit at least one IL-12 activity.

The heavy chain, light chain CDRs, variable regions, or variable and constant regions are cloned and put into appropriate expression vectors. A typical mammalian expression vector contains at least one promoter element, which mediates the initiation of transcription of mRNA, the Ig derived protein or specified portion or variant coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors, such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded Ig derived protein or specified portion or variant. The DHFR (dihydrofolate reductase) marker is useful to develop cell lines that carry several hundred or even several thousand copies of the gene of interest.

Another useful selection marker is the enzyme glutamine synthase (GS) (Murphy, et al., Biochem. J. 227:277-279 (1991); Bebbington, et al., Bio/Technology 10: 169-175

(1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of Ig derived protein or specified portion or variants.

Cloning and Expression in CHO Cells

The vector pC4 is used for the expression of IL-23 Ig derived protein or specified portion or variant. Plasmid pC4 is a derivative of the plasmid pSV2-dhfr (ATCC Accession No. 37146). The plasmid contains the mouse DHFR gene under control of the SV40 early promoter. Chinese hamster ovary— or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990); and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

The plasmid pC4 (and also pC1) contains for expressing the gene of interest the strong promoter of the long terminal repeat (LTR) of the Rous Sarcoma Virus (Cullen, et al., Molec. Cell. Biol. 5:438-447 (1985)) plus a fragment isolated from the enhancer of the immediate early gene of human cytomegalovirus (CMV) (Boshart, et al., Cell 41:521-530 (1985)). Downstream of the promoter are BamHI, XbaI, and Asp718 restriction enzyme cleavage sites that allow integration of the genes; the multiple cloning sites facilitate cloning of the gene of interest. Behind these cloning sites, the plasmid contains the 3' intron and polyadenylation site and termination signal of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the IL-23 in a regulated way in mammalian cells (M. Gossen, and H. Bujard, Proc. Natl. Acad. Sci. USA 89: 5547-5551 (1992)). For the polyadenylation of the mRNA other signals, e.g., from the human growth hormone or globin genes, can be used as well. Stable cell lines carrying a gene of interest integrated into the chromosomes can also be selected upon co-transfection with a selectable marker, such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The DNA sequence encoding the complete IL-23 Ig derived protein or specified portion or variant is used, corresponding to HC and LC variable regions of an IL-23 Ig derived protein of the present invention, according to known method steps. Isolated nucleic acid encoding a suitable human constant region (i.e., HC and LC regions) is also used in this construct (e.g., as provided in vector p1351).

The isolated variable and constant region encoding DNA and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 μg of the expression plasmid pC4 is cotransfected with 0.5 μg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 μg/ml G418. After 2 days, the cells are trypsinized and seeded in hybridoma cloning plates (Greiner, Germany) in alpha minus MEM supplemented with 10, 25, or 50 ng/ml of methotrexate plus 1 μg/ml G418. After about 10-14 days, single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot or by reverse phase HPLC analysis.

The completely human anti-IL-23 protein Ig derived proteins are further characterized. Several of the generated Ig derived proteins are expected to have affinity constants between $1\times10^9$ and $9\times10^{12}$. Such high affinities of these fully human monoclonal Ig derived proteins make them suitable for therapeutic applications in IL-23 protein-dependent diseases, pathologies or related conditions.

Example 2

Comparison of the Therapeutic Efficacy of Anti-IL-12P35 and Anti-IL-12/23P40 Antibodies in Murine Experimental Autoimmune Encephalomyelitis (EAE)

Summary: This set of studies was performed to investigate the therapeutic efficacy of IL-12 or IL-12/IL-23 specific neutralization in a mouse model for multiple sclerosis, experimental autoimmune encephalomyelitis (EAE). Neutralizing rat anti-mouse monoclonal antibodies (mAbs) specific for the p35 subunit of IL-12 or the p40 subunit that is shared between IL-12 and IL-23 were administered either prior to disease induction, prior to disease onset, or after disease was ongoing. In all cases, only anti-p40 demonstrated therapeutic potential. These data suggest that IL-23 is the predominant contributor to disease pathogenesis in this autoimmune model.

| Abbreviations: | |
| --- | --- |
| IL | Interleukin |
| mAb | Monoclonal antibody |
| EAE | Experimental autoimmune encephalomyelitis |
| Th | T helper cell |
| IFNγ | Interferon gamma |

-continued

| Abbreviations: | |
|---|---|
| cs | Clinical score |
| MBP | Myelin basic protein |
| PK | Pharmacokinetics |

Introduction: Biologically active IL-12 exists as a heterodimer comprised of 2 covalently linked subunits of 35 (p35) and 40 (p40) kilo Daltons. Several lines of evidence have demonstrated that IL-12 can induce robust Th1 immune responses that are characterized by production of IFNγ and IL-2 from $CD4^+$ T cells. Inappropriate Th1 responses, and thus IL-12 expression, are believed to correlate with many immune-mediated diseases, such as multiple sclerosis, rheumatoid arthritis, inflammatory bowel disease, insulin-dependent diabetes mellitus, and uveitis. In animal models, IL-12 neutralization was shown to ameliorate immune-mediated disease. However, these studies neutralized IL-12 through its p40 subunit. The recent description of IL-23 (1), a heterodimeric cytokine that shares the p40 subunit, made it important to determine whether previous findings were due to IL-12 or IL-23 activity. Therefore, p35 and p40 specific neutralization were compared in a mouse model of autoimmunity, experimental autoimmune encephalomyelitis (EAE). Neutralizing antibodies specific for IL-12p35 had no effect on EAE progression. In contrast, neutralization of both IL-12 and IL-23 with an anti-p40 mAb suppressed clinical signs of EAE, whether antibody was administered before or after Th1 differentiation. This data suggests that the activity of anti-p40 treatment in EAE is based solely on neutralization of IL-23.

Methods and Materials:

Mice:

Female C3H/HEB/FEJ mice (Jackson Laboratories, Bar Harbor, Me.) were used in pharmacokinetic analyses. For EAE studies, female B10.PL ($H-2^u$) mice were purchased from the Jackson Laboratories, and were used between 6-8 weeks of age. All animals were maintained according to IACUC guidelines under approved protocols.

Antibodies:

C17.8 (rat anti-mouse IL-12/IL-23p40, IgG2a), and C18.2 (rat anti mouse IL-12p35, IgG2a) hybridomas provided by Dr. Giorgio Trinchieri and the Wistar Institute (Philadelphia, Pa.). Ascites was generated at Harlan Bioproducts (Indianapolis, Ind.) and purified by protein G affinity.

Serum PK of Rat Anti-Mouse Antibodies:

Female C3H/HEB/FEJ mice, approximately 20-25 grams, were individually weighed and treated with a single 5 mg/kg intraperitoneal dose of $^{125}I$ labeled antibody (C17.8, C18.2), with a constant dose volume/mouse of 10 mL/kg. Retroorbital bleeds were taken from anesthetized mice at 30 minutes, 6 and 24 hours, 4, 7, 11 and 18 days. Blood samples were allowed to stand at room temperature for at least 30 minutes, but no longer than 1 hour, and were then centrifuged at approximately 2,500-3,500 rpm for 10-15 minutes. Approximately 50 uL aliquots of each serum sample were counted for 125Iusing a LKB Compugamma 1282 counter (Wallac, Gaithersburg, Md.). 10 mL aliquots of the injectates were also counted. The average fraction of injected counts at each time point was calculated and multiplied by the total mg of antibody injected to determine the total mg remaining in the serum at each time point. Data is shown as the mean mg of mAb in the sera +/−s.d. with 5-10 animals in each group.

EAE Induction and Scoring:

For EAE induction, female B10.PL mice were injected subcutaneously over four sites on the back with a total of 100 μl of CFA (containing 200 μg Mycobacterium tuberculosis Jamaica strain) combined with 200 μg guinea pig-MBP (Sigma). Mice also received 200 ng pertussis toxin (List Biological, Campbell, Calif.) i.p. in 0.2 ml PBS at the time of immunization and 48 hours later. Mice received i.p. injections of C17.8 (anti-IL-12p40) or C18.2 (anti-IL-12p35) monoclonal antibodies diluted to 100 mg/kg (C18.2) or 20 mg/kg (C17.8) in PBS, on indicated days. Control mice received PBS or Rat IgG (Biosource) at 20 mg/kg in PBS.

Animals that demonstrated clinical signs (cs) were scored as follows: limp tail or waddling gait with tail tonicity 1, waddling gait with limp tail (ataxia) 2, ataxia with partial limb paralysis 2.5, full paralysis of one limb 3, full paralysis of one limb with partial paralysis of second limb 3.5, full paralysis of two limbs 4, moribund 4.5, death 5. Animals that scored a 5 were not included in the mean daily cs analysis for the rest of the experiment. Daily cs are averaged for the group, and mean incidence, day of onset, highest acute cs, cumulative cs, cs/day, number of relapses and relapse severity ±sem are described. Mean cumulative cs per group was calculated by averaging the sum of daily clinical scores for individual animals. cs/day was calculated by dividing the cumulative cs by the number of days the animal remained in the study. To determine the mean day of onset, animals not developing EAE were not included in the analysis. To determine the mean highest cs, mice not developing EAE were assigned a value of "0" and included in the analysis. Relapses were defined by a full point drop in clinical score sustained for at least 2 observed days followed by a full point increase in clinical score sustained for at least 2 observed days.

Results and Discussion: Anti-p35 and Anti-p40 Antibodies have Identical Pharmacokinetics To establish the clearance rates of anti-p40 and anti-p35 antibodies, normal mice were injected with a single 5 mg/kg dose of $^{125}I$ labeled antibodies and circulating levels were measured for 11 days post antibody administration. Anti-p35 and anti-p40 had overlapping pharmacokinetics, demonstrating that clearance rates are identical in normal mice (2). The expected clearance rate of each mAb is approximately 7-10 days. Although this is a single dose PK study, these data support once weekly dosing for in vivo studies.

Only Anti-p40 Treatment Prior to EAE Induction is Protective

To determine the relative roles of IL-12 and IL-23 in immune-mediated diseases, we utilized a murine model for multiple sclerosis, relapsing experimental autoimmune encephalomyelitis (EAE). Upon EAE induction with myelin basic protein (MBP) in adjuvant, B10.PL mice typically exhibit an initial episode of paralysis (acute disease), then recover either partially or completely and progress through multiple relapses and/or chronic EAE. It has long been assumed that EAE is dependent upon IL-12 expression since IL-12 is believed to be a primary mediator of Th0 to Th1 differentiation. However, to distinguish the potential role of IL-23 in EAE induction, neutralizing concentrations of anti-p40 (IL-12 and IL-23) or anti-p35 (IL-12 only) antibodies were established one day prior to immunization for EAE (Day-1). Onset of disease can vary between animals; therefore, treatment was repeated 7 and 14 days later to ensure that anti-p35 and IL-p40 antibodies were present during Th1 differentiation. Several in vitro neutralization studies have demonstrated that the anti-40 mAb is 5 times more effective in neutralizing IL-12 than the anti-p35 mAb (data not shown).

Therefore, the dose of anti-p35 mAb was adjusted to be 5 fold higher than anti-p40 in all EAE experiments. In two separate experiments, mice treated with Rat IgG isotype control antibody (20 mg/kg) or anti-p35 (100 mg/kg) did not demonstrate protection from disease. It is important to note that peripheral administration of a non-specific control antibody (Rat IgG) did not alter the clinical course of disease when compared to non-treated mice with EAE. In both studies, mice treated with anti-p40 mAb (20 mg/kg) exhibited nearly complete inhibition of EAE clinical signs. Remarkably, suppression of disease extended beyond the expected rate of antibody clearance through 70 days post EAE induction. In each experiment, only one animal treated with anti-p40 exhibited two consecutive days of EAE clinical signs, and each demonstrated a late onset and significantly lower acute clinical scores, cumulative clinical scores, and no relapses in disease (Table 1). These results demonstrate that neutralization of IL-12 and IL-23 through the shared p40 subunit provided nearly complete protection from EAE. In contrast, specific neutralization of IL-12 only via anti-p35 was ineffective. These data strongly suggest that EAE is not mediated by IL-12.

Only Anti-p40 Treatment Just Prior to Disease Onset is Protective

Although prophylactic treatment completely protected mice from EAE, it remained to be determined if IL-12 specific neutralization would be protective once the Th1 population was established in vivo. Therefore, in a separate set of experiments, mice were treated with either a control antibody (Rat IgG), anti-p35, or anti-p40 monoclonal antibodies ten days after EAE induction, but prior to disease onset. Since typical immune responses occur within 7 days, this time point should reflect the effects of anti-IL-12 or anti-IL-23 mAbs on differentiated Th1 cells. EAE onset can vary between animals, therefore treatment was repeated 7 and 14 days later to ensure that anti-p35 and anti-p40 antibodies were present during the onset of disease. In two separate experiments, mice treated with isotype control antibody (20 mg/kg) or anti-p35 (100 mg/kg) were not protected from disease, when compared to untreated EAE mice. However, mice treated with anti-p40 mAb (20 mg/kg) were significantly protected from EAE. As shown in the previously described studies, disease suppression was observed well beyond the time required for clearance of peripherally administered antibody through day 70 post EAE induction. Considering that antibody was not administered until after Th1 differentiation (day 10), it was not surprising that disease incidence, day of onset, and the highest clinical score during acute EAE were not different in any group (Table 2). However, in both experiments, mice receiving anti-p40 exhibited significantly lower cumulative clinical scores, clinical scores per day, and relapse severity.

Only Anti-p40 Treatment During Established EAE is Protective

The most difficult, but clinically relevant, hurdle for any therapy is to suppress established disease. Therefore another set of experiments was performed in which mice were immunized for EAE, then divided into treatment groups once disease was ongoing. Approximately 30 days post EAE induction, mice had progressed through the acute phase of disease. At this time, animals were divided into groups with comparable cumulative and daily clinical scores. Treatment was repeated 7 and 14 days later to ensure that antibodies were available in neutralizing concentrations during the transition from acute to chronic or remitting-relapsing disease. Only anti-p40 treatment (20 mg/kg) ameliorated disease when compared to either isotype control antibody (20 mg/kg) or anti-p35 (100 mg/kg) treated animals. Disease suppression was observed through day 80 post EAE induction. In both experiments, analysis from the first day of treatment through day 80 demonstrated that mice receiving anti-p40 exhibited lower cumulative clinical scores, clinical scores per day, and the least highest clinical score post treatment. These data suggest that not only is IL-23 likely to mediate Th1 differentiation (Table 1) and EAE induction (Table 2), but IL-23 also contributes to the effector phase of chronic immune-mediated (e.g., autoimmune) responses (Table 3). Therefore, anti-p40 treatment can offer therapy at any time in the progression of immune-mediated diseases.

Conclusions

The understanding of the role of IL-12 in immune function has been based on studies of the p40 subunit of IL-12. Therefore, a side-by-side comparison of neutralization of the IL-12 specific p35 subunit versus the p40 subunit shared between IL-12 and IL-23 was conducted in an animal model of autoimmune disease. Neutralization via anti-p40 significantly inhibited EAE when mAb was administered at any time point. However, IL-12 specific neutralization was completely ineffective. Therefore, our data shows that IL-12 does not contribute to this autoimmune model and that IL-23 is expected be the more prominent mediator of autoimmune T cell responses.

Example 3

IL-23 Mediates Experimental Autoimmune Encephalomyelitis

Materials and Methods

Animals:

Female B10.PL mice (Jackson Laboratories, Bar Harbor, Me.) and female C57BL/6 mice (Charles River Laboratories, Raleigh N.C.) between 6-8 weeks of age were used and maintained according to IACUC guidelines under approved protocols.

Antibodies

Rat monoclonal antibodies to mouse IL-23 were developed at Centocor (Malvern, Pa.). Negative rat IgG (from Biosource, Camarillo, Calif.) was used as a control. Neutralizing rat anti-mouse p40 (C17.8), and rat anti-mouse IL-12 (C18.2) antibodies were provided by Dr. Giorgio Trinchieri and the Wistar Institute (Philadelphia, Pa.). Ascites was generated at Harlan Bioproducts (Indianapolis, Ind.) and antibodies were purified by protein G affinity chromatography.

Cytokines

Recombinant murine IL-12 was obtained from R&D Systems (Minneapolis, Minn.). Recombinant hIFN-γ and human IL-2 were obtained from Peprotech (Rocky Hill, N.J.). Murine IL-23 was generated using transient transfection technology and Immobilized Metal Affinity Chromatography (IMAC). Briefly, separate expression constructs for murine p40 and murine p19-His were co-transfected into HEK 293E cells using Lipofectamine 2000 (Invitrogen, Carlsbad, Calif.) as suggested by the manufacturers instructions. Alternatively, a linked IL-23 construct was generated as described and transfection of HEK 293E cells was performed. Twenty-fours hours post-transfection, the growth medium was replaced with serum-free 293 SFMII (Invitrogen) and left to condition for 5 days. The media was then removed, centrifuged, and processed by IMAC using TALON resin (BD Biosciences, Palo Alto, Calif.). His-tagged proteins were eluted with 150 mM EDTA, then dialyzed against PBS, concentrated, filtered, and stored at −80° C. Bioactivity of both co-transfected and linked IL-23 was verified by splenocyte IL-17 protein production as described below.

IL-12 and IL-23 ELISA

Murine IL-12 and murine IL-23 (1 µg/ml) were coated overnight on Nunc Maxisorp plates in PBS. After the plates were washed and blocked, rat anti-mouse p40, rat anti-mouse IL-12, and rat anti-mouse IL-23 antibodies were titrated and allowed to bind for 2 hours. Bound protein was detected using 1:10,000 HRP-conjugated goat anti-rat IgG antibody (from Jackson Immuno Research, West Grove, Pa.) followed by substrate. Data is shown as the mean optical density of replicate wells.

IL-12 Neutralization

Non-adherent human peripheral blood mononuclear cells (PBMC) were cultured for four days with 5 µg/ml PHA (Lectin, Phaseolus vulgaris, Sigma, St. Louis, Mo.) in complete RPMI-1640 (Invitrogen) with 10% heat-inactivated fetal bovine serum (JRH, Lenexa, Kans.), 1% L-glutamine (JRH), 100 Units/ml penicillin and 100 µg/ml streptomycin (Invitrogen). Cells were harvested, washed, then cultured with rhIL-2 (10 units/ml) in the presence of murine IL-12 (1 ng/ml) either alone or pre-incubated with tested antibodies for 22 hours. Supernatants were analyzed for human IFNγ protein levels by luminescence immunoassay using anti-IFNγ antibodies generated at Centocor.

IL-23 Neutralization

Single cell suspensions were prepared from spleens of C57BL/6 mice. $2 \times 10^6$ cells/ml were cultured in complete RPMI with 10 U/ml rhIL-2 (Peprotech) and 1 ng/ml mouse IL-23, either alone or pre-incubated with tested antibodies for 3 days. Supernatants were collected and analyzed for IL-17 protein by ELISA (R&D Systems) per the manufacturer's instructions.

EAE Analysis

Female B10.PL mice were injected s.c. over four sites on the back with a total of 100 µl of complete Freunds adjuvant (CFA) combined with 200 µg guinea pig-myelin basic protein (MBP) (Sigma). Mice also received 200 µg pertussis toxin (List Biological, Campbell, Calif.) i.p. in 0.2 ml PBS at the time of immunization and 48 hours later. Mice received i.p. injections of anti-p40, anti-IL-12, or anti-IL-23 monoclonal antibodies diluted to 100 mg/kg (anti-IL-12), 20 mg/kg (anti-p40, anti-IL-23), or 50 mg/kg (anti-IL-23) in PBS, on indicated days. Control mice were either not treated or received Rat IgG (Biosource, Camarillo, Calif.) at 20 mg/kg in PBS.

Animals that demonstrated clinical signs (cs) were scored as follows: limp tail or waddling gait with tail tonicity 1, waddling gait with limp tail (ataxia) 2, ataxia with partial limb paralysis 2.5, full paralysis of one limb 3, full paralysis of one limb with partial paralysis of second limb 3.5, full paralysis of two limbs 4, moribund 4.5, death 5. Scores for animals that were sacrificed or scored a 5 were not included in the mean daily cs analysis for the rest of the experiment. Daily cs are averaged for the group, and incidence, mortality, day of onset, highest acute cs, cumulative cs, cs/day, number of relapses and relapse severity ±sem are described. Mean cumulative cs per group was calculated by averaging the sum of daily clinical scores for individual animals. Cs/day was calculated by dividing the cumulative cs by the number of days the animal remained in the study. To determine the mean day of onset, animals not developing EAE were not included in the analysis. To determine the mean highest acute cs, mice that never developed EAE were assigned a value of "0" and included in the group mean. Relapses were defined by a full point drop in clinical score sustained for at least 2 observed days followed by a full point increase in clinical score sustained for at least 2 observed days. To determine the mean number of relapses per group, mice not demonstrating a defined relapse were assigned a value of "0" and included in the group mean. To determine the mean relapse severity, the highest clinical score of each relapse event was averaged and animals that did not relapse were not included in the analysis.

For ex vivo EAE analysis, spleens and peripheral lymph nodes (inguinal, axillary, brachial, and cervical) were harvested from each animal on days 10, 17, 24, or 32 post EAE induction. Single cell suspensions ($5 \times 10^5$/well) were prepared from individual animals, washed twice, then cultured in vitro in RPMI complete for 72 hours with 40 µg/ml MBP, 5 µg/ml ConA, or media alone and proliferation was measured using ATPLite (Perkin Elmer, Boston, Mass.). Data is represented as a stimulation index, which is the mean proliferation to MBP divided by the mean proliferation to media alone. Splenocytes and lymph node cells were also cultured at $4 \times 10^6$ cells/ml with 40 µg/ml MBP or media alone for 48 hours and supernatants were tested for IFNγ, IL-17, IL-4, IL-5, and IL-10 proteins by ELISA, according to the manufacturer instructions (R&D Systems). Even though minimal cytokine levels were detected in media-only cultures, those values were subtracted from the levels found in MBP-stimulated cultures so that the data presented represents only antigen-specific cytokine production.

For histopathologic examination and ranking, mouse brains and spinal columns were fixed in 10% buffered formalin by emersion. After fixation, the brains were sliced coronally into 4 segments. Spinal columns were decalcified in 5% EDTA and then sliced sagitally into 5 segments. The tissues were processed and embedded in paraffin using routine methods. Tissue blocks were sectioned at 5 µm, and stained with hematoxylin and eosin (H&E) or Luxol Blue-Cresyl Echt Violet (Poly Scientific, Bay Shore, N.J.). Additional sections were stained immunohistochemically for glial fibrillary acidic protein (GFAP) (BioGenex, San Ramon, Calif.). Sections were blinded and ranked based on the extent of inflammation. Brains and spinal cords were analyzed separately.

Results

IL-23 specific neutralization ameliorates EAE

Figure 1B:
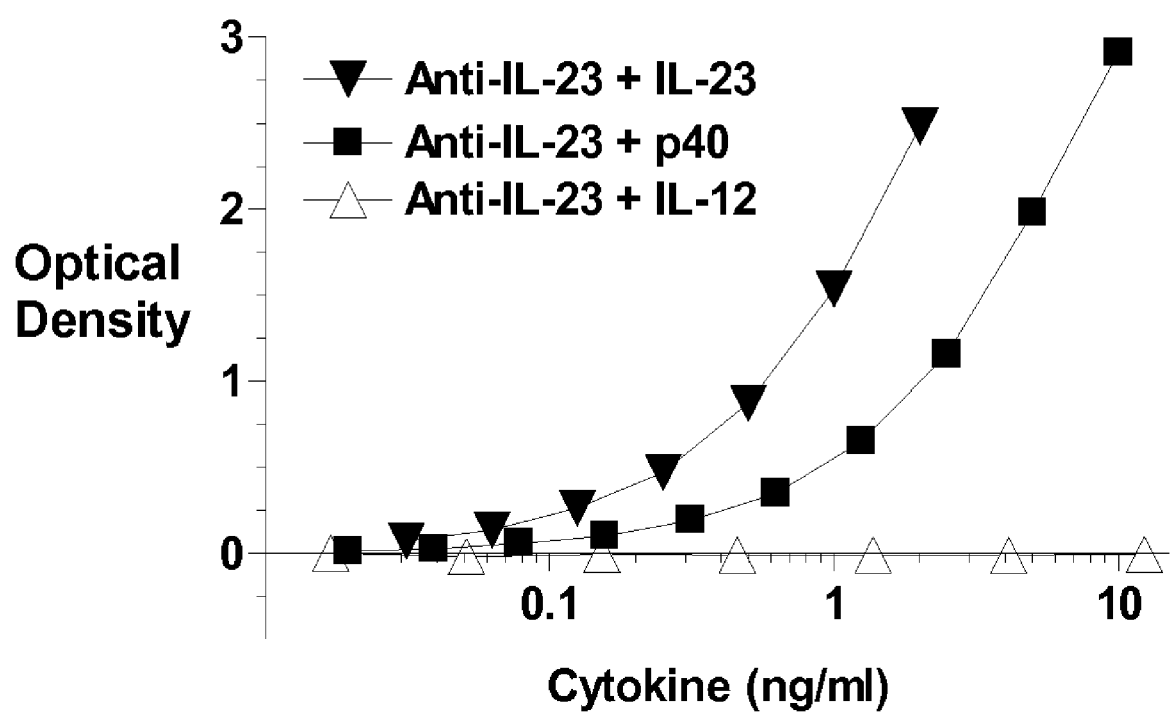
FIG. 1B is a graph showing the specificity of the anti-IL-23 antibody for the IL-23p40 subunit.

To confirm that neutralization of only IL-23 will provide effective therapy for EAE, monoclonal antibodies to mouse IL-23 were generated. As shown in FIG. 1A, an antibody specific for mouse IL-23 that demonstrated no reactivity with mouse IL-12 was identified. Subsequent studies have shown that the anti-IL-12 and anti-IL-23 antibodies do not cross react even when 100 ng/ml of the opposite cytokine is present. As shown in FIG. 1B, the anti-IL-23 specific antibody binds to the p40 subunit of IL-23 and does not bind to the p19 subunit. Accordingly, it is IL-23p40 specific.

Figure 1C:
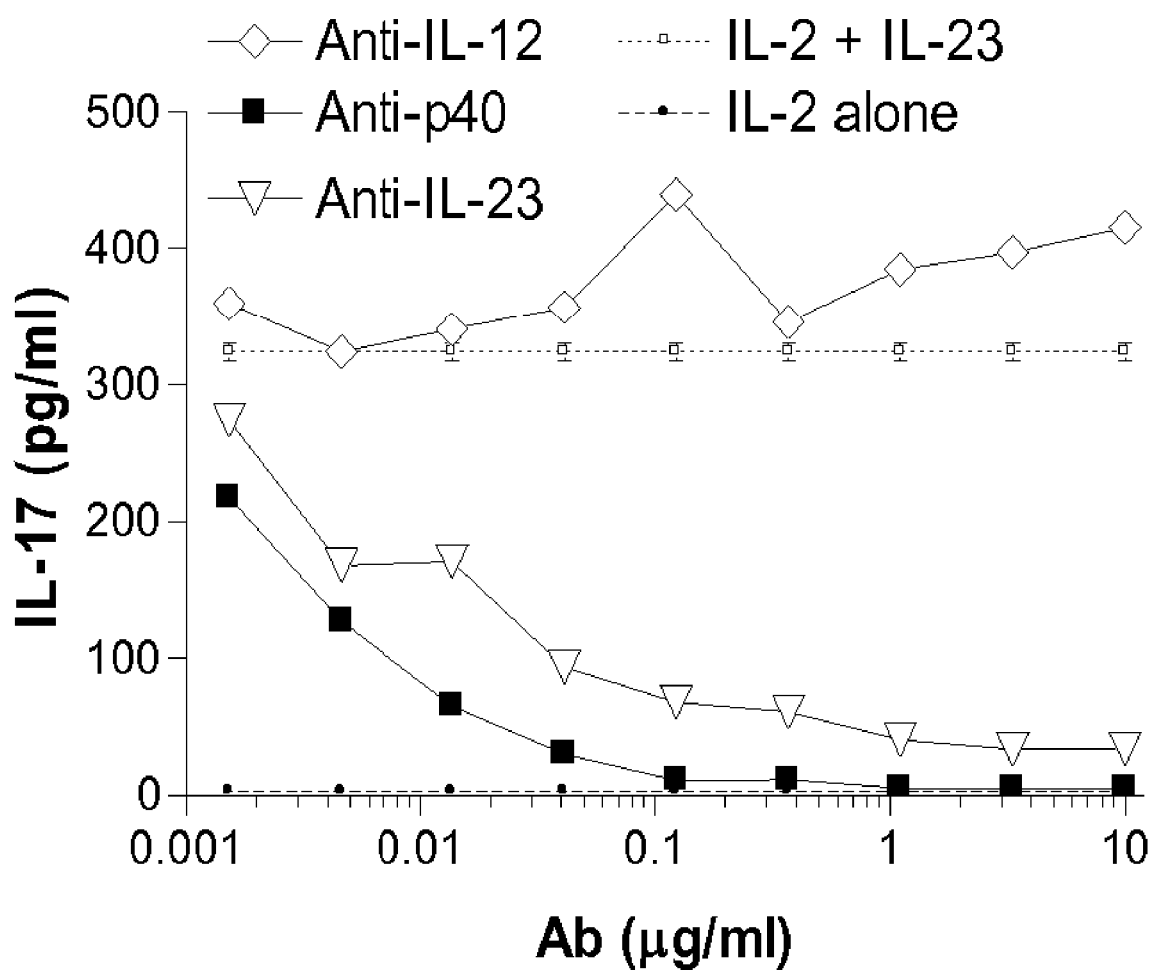
FIG. 1C is a graph showing the biological effect of antibodies on IL-23 induced IL-17 production.
Figure 1D:
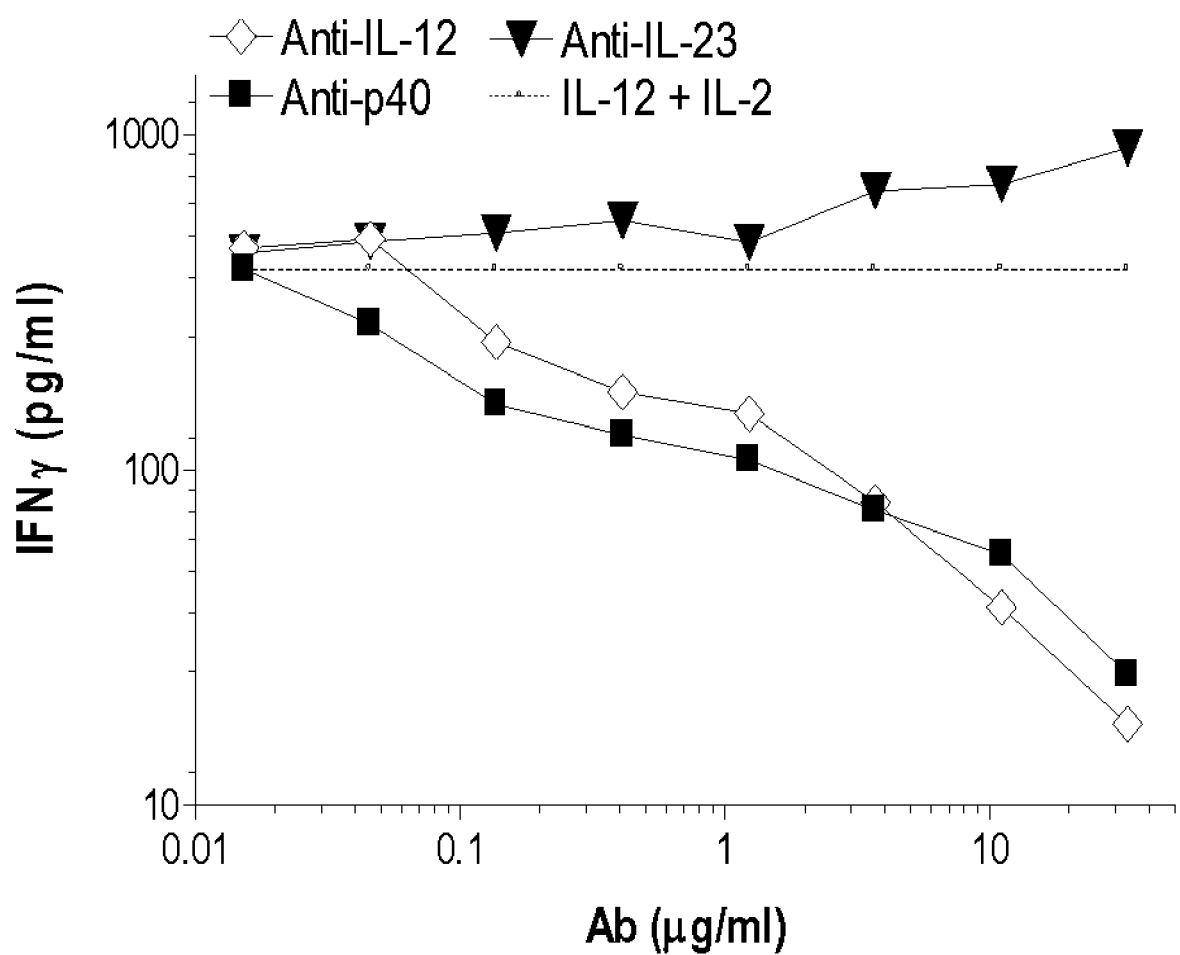
FIG. 1D is a graph showing the biological effect of antibodies on IL-12 induced IFNγ production.
Figure 1E:
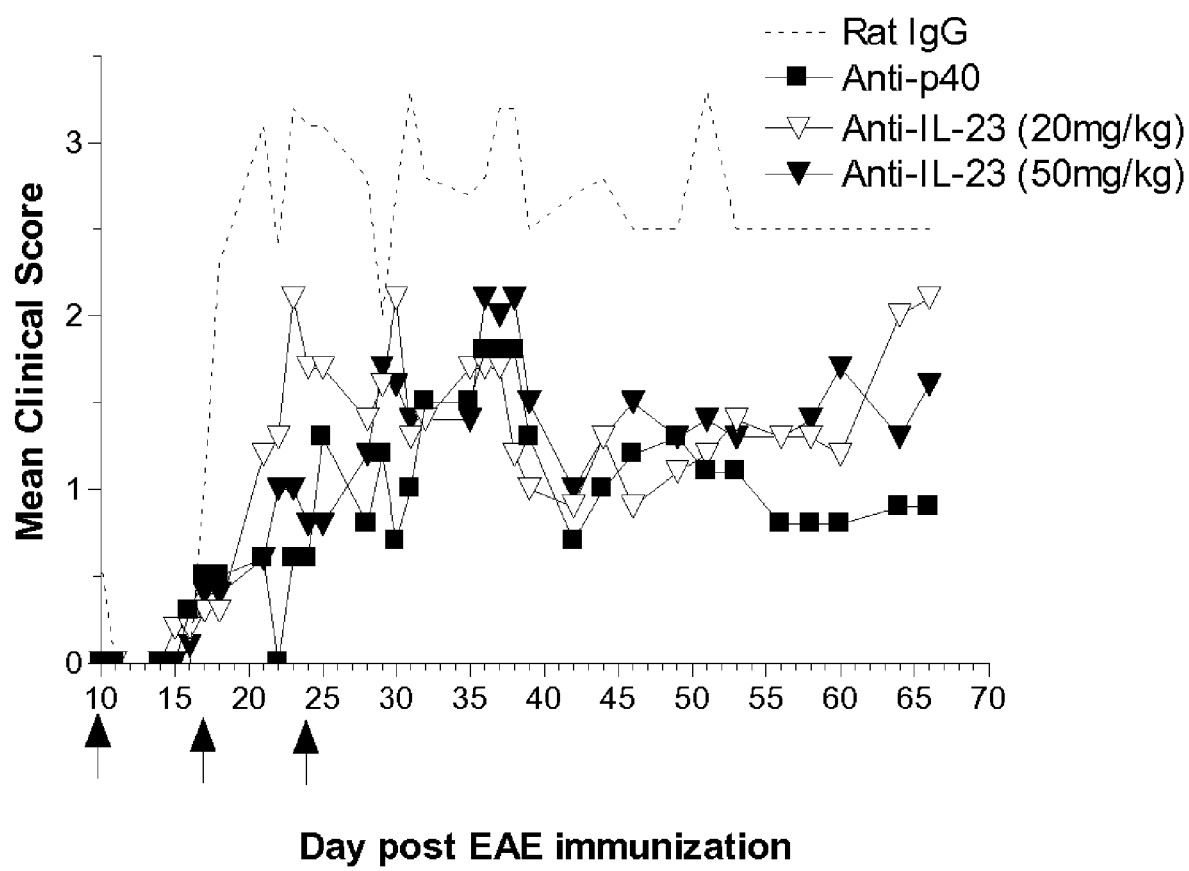
FIG. 1E is a graph showing the clinical suppression of EAE by the antibodies.

Since it was recently shown that IL-23 will induce IL-17 production, these antibodies were tested for their ability to neutralize IL-23 bioactivity. As shown in FIG. 1C, the IL-23 specific antibody inhibits IL-17 production with similar potency as anti-p40. In contrast, the anti-IL-12 antibody demonstrated no effect on IL-17 levels. Lastly, to confirm that the anti-IL-23 antibody does not interfere with IL-12 function, the antibodies' ability to inhibit IFNγ production in T cell cultures was tested. As previously demonstrated, anti-IL-12 and anti-p40 inhibited IFNγ production, however, the anti-IL-23 antibody had no effect on IFNγ levels (FIG. 1D). Therefore, a neutralizing anti-mouse IL-23 antibody that does not bind IL-12 or inhibit IL-12 mediated responses has been developed.

The anti-IL-23 and anti-p40 antibodies were compared for in vivo inhibition of EAE. Mice were dosed with a control antibody, anti-p40, or anti-IL-23 either ten days after EAE induction or during established EAE. In both paradigms, mice treated with anti-IL-23 demonstrated clinical suppression of EAE comparable to that of anti-p40 treated animals (FIG. 6A). Mice receiving anti-p40 or anti-IL-23 exhibited a later day of onset, reduced severity of acute disease and subsequent relapses, and lower clinical scores per day. These results demonstrate that even in mice that have not been genetically manipulated, IL-23, and not IL-12, is responsible for encephalitogenic T cell responses in EAE.

IL-23 Neutralization Prevents EAE Pathology in the CNS

EAE presents as an ascending hind limb paralysis and is therefore scored for severity by deficits in motor function. However, the cause of this impairment can only be observed by assessing pathology within the brain and spinal cord. Therefore, a separate study was performed in which mice were immunized for EAE, then treated with control Rat IgG, anti-IL-12, anti-p40, or anti-IL-23 antibodies on days 10 and 17. The mice were scored daily for EAE clinical signs and then sacrificed on day 24 by cardiac perfusion. Sections of the brain and spinal cord were blinded and ranked from least to most severe, then correlated to the clinical score of the animal on the day of sacrifice.

The severity of spinal cord pathology correlated with the clinical score severity, whereas brain pathology did not. This is not surprising since clinical scoring is defined by motor ability, which is primarily a measurement of spinal cord function. Histopathology rankings were then sub-divided into treatment groups to assess differences after 2 in vivo antibody treatments (day 24). All treatment groups, including anti-IL-12, had lower pathology rankings than the Rat IgG treated control animals. However, it is important to note that with treatment paradigms that are initiated 10 days post EAE induction, clinical protection with anti-p40 or anti-IL-23 is not typically observed until day 30 or later (FIG. 1D).

Figure 2A:
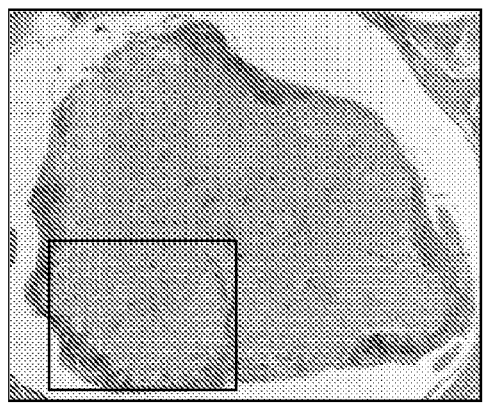
FIG. 2A is an image showing the H&E stained thoracic spinal cord from mice treated with control rat IgG (40 times magnification).
Figure 2B:
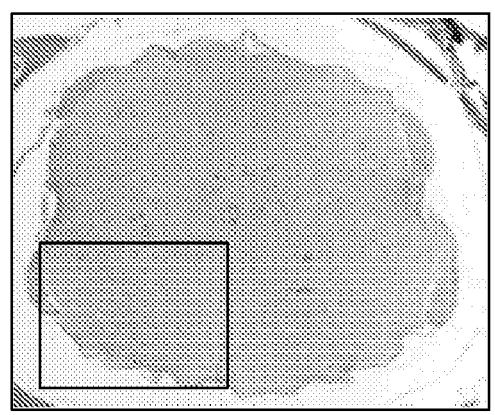
FIG. 2B is an image showing the H&E stained thoracic spinal cord from mice treated with anti-IL-23 antibody (40 times magnification).
Figure 2C:
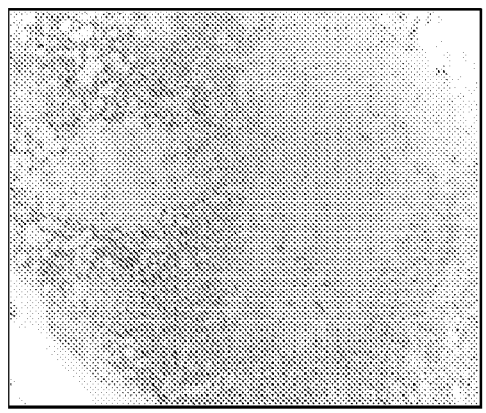
FIG. 2C is an image showing the Luxol Blue stained thoracic spinal cord from mice treated with control rat IgG (200 times magnification).
Figure 2D:
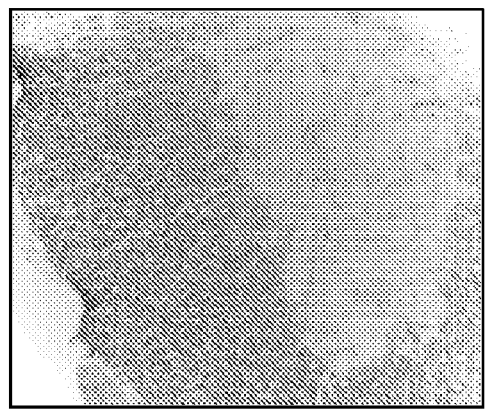
FIG. 2D is an image showing the Luxol Blue stained thoracic spinal cord from mice treated with anti-IL-23 antibody (200 times magnification).
Figure 2E:
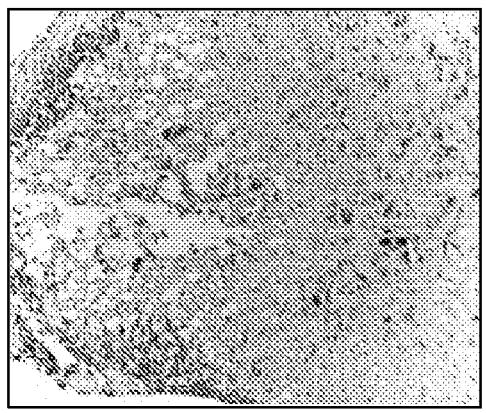
FIG. 2E is an image showing the GFAP stained thoracic spinal cord from mice treated with control rat IgG (200 times magnification).
Figure 2F:
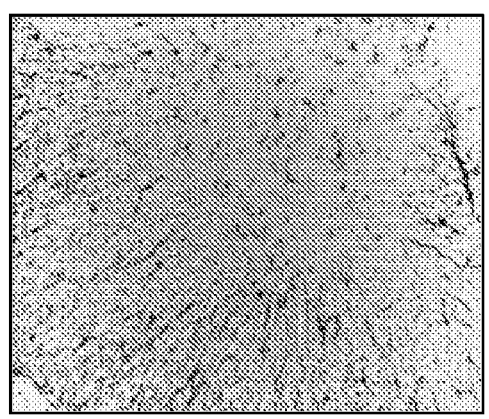
FIG. 2F is an image showing the GFAP stained thoracic spinal cord from mice treated with anti-IL-23 antibody (200 times magnification).

There were remarkable differences in spinal cord inflammation, demyelination, and astrocyte gliosis when the Rat IgG control and anti-IL-23 groups were compared. Serial sections of thoracic spinal cord from mice representative of the median clinical score ranking of the control (rat IgG) group and anti-IL-23 treated group were stained: (1) by H&E to evaluate cellular infiltration (FIGS. 2A and 2B at 40 times magnification) in which FIG. 2A represents the control group and FIG. 2B represents the anti-IL-23 treated group; (2) by Luxol Fast Blue to evaluate demyelination (FIGS. 2C and 2D at 200 times magnification) in which FIG. 2C represents the control group and FIG. 2D represents the anti-IL-23 treated group; and (3) by GFAP to evaluate astrocyte gliosis (FIGS. 2E and 2F at 200 times magnification) in which FIG. 2E represents the control group and FIG. 2F represents the anti-IL-23 treated group. These data confirm that the clinical protection that is observed after anti-IL-23 therapy is a result of partial protection from CNS pathology.

IL-23 Specific Neutralization Leaves IL-12 Pathways Intact

Mouse strains that are susceptible to *Leishmania major* are unable to contain the organism, whereas resistant strains will localize the organism and lesions will spontaneously heal. It has been previously demonstrated that administration of anti-p40 antibodies decreases the ability of resistant mice to clear *Leishmania major*, presumably due to a diminished Th1 response. To determine the specific role of IL-12, anti-IL-12 and anti-p40 antibodies in the *L. major* model in a resistant mouse strain were compared. Remarkably, despite the 5-fold lower neutralizing capacity of anti-IL-12 antibody, each antibody equally delayed immunity to *L. major* for 50 days (FIG. 6B). IL-12 specific in vivo neutralization seemed to have a longer lasting effect in delaying *L. major* immunity, when compared to anti-p40 treatment even though lesions in animals from both treatment groups were nearly resolved by the end of the observation period (day 85).

Utilizing the neutralizing murine IL-23 antibody, the in vivo responses to *L. major* upon IL-23 neutralization were investigated. As shown in FIG. 6C, anti-IL-23 did not alter immunity to *L. major* when compared to Rat IgG treated animals. In contrast, IL-12 neutralization via IL-12 or p40 specific antibodies did inhibit *L. major* immunity, as observed previously (FIG. 6B) in a slightly different model of *L. major* infection. These results confirm that neutralization of IL-23 can provide therapy for immune-mediated disease, while leaving IL-12 pathways of pathogen immunity intact.

Example 4

IL-23p40 Epitope

IL-23 functions by binding to a 2-chain receptor complex that is expressed on the surface of T cells, natural killer (NK) cells, and potentially antigen presenting cells. The IL-12Rbeta($\beta$)-1 chain is a non-signaling receptor chain that is responsible for IL-12/23p40 binding. Therefore, it is logical that IL-12R$\beta$1 is a component of both the IL-12 and the IL-23 receptor complexes. However, each receptor complex has a signaling subunit that is specific for each respective cytokine.

Figure 3:
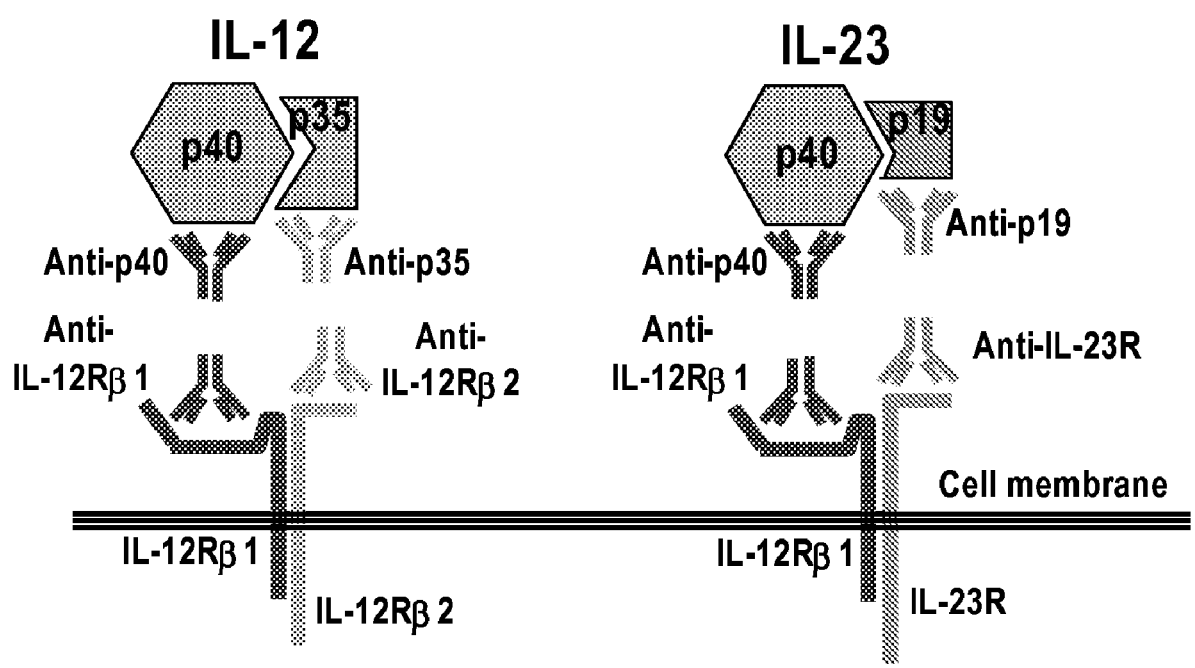
FIG. 3 shows the understood mechanisms for specific antibody neutralization of IL-12 and/or IL-23.

IL-12R$\beta$1 binds to the p35 subunit of IL-12 and is responsible for initiating IL-12 specific cellular responses. In contrast, IL-23R binds to IL-23p19 and is responsible for IL-23 specific cellular responses. It is understood that neutralizing antibodies that bind to the p40 subunit of IL-12 or IL-23, or the shared IL-12RP 1, can inhibit the bioactivity of both cytokines by preventing cytokine/receptor interaction. However, it was assumed that specific inhibition of IL-12 could only be achieved through antibodies to IL-12p35 or IL-12R$\beta$2 (see FIG. 3 showing the understood mechanisms for specific antibody neutralization of IL-12 and/or IL-23). Likewise, it was assumed that specific inhibition of IL-23 could only be achieved through antibodies to IL-23p 19 or IL-23R (FIG. 3).

The present invention provides novel p40 epitopes that are available in an IL-23 (p19/p40) complex and not in IL-12 (p35/p40) and an antibody with no reactivity to IL-12 that can bind to p40 epitope(s) and specifically inhibit IL-23 through interruption of IL-23 p40 binding to IL-12R$\beta$1. In addition, the present invention provides methods of generating anti-human or murine IL-23p40 binding agents. These agents would provide IL-23 specific therapy for immune-mediated disease without interrupting IL-12 mediated pathways.

Experimental Results:

Rats were immunized with DNA encoding murine IL-23p 19, then subsequently boosted with murine IL-23 protein. Hybridomas were generated and supernatants were tested for IL-23 and IL-12 reactivity. Hybridomas that produced IL-23 positive and IL-12 negative antibodies were subcloned twice to generate monoclonal cultures. Four rat anti-mouse monoclonal antibodies (mAb) were identified that bound IL-23 and not IL-12. These mAbs were further characterized for neutralization potency. One mAb was identified that had no reactivity to murine IL-12, yet potently neutralized the bioactivity of murine IL-23.

The mAb was further analyzed for IL-23 subunit specificity, and it was discovered to bind to the p40 monomer. Therefore, through monoclonal antibody technology, a functional p40 epitope that is present in an IL-23 (p19/p40) complex that is not present in an IL-12 (p35/p40) complex has been identified. While it might not be unexpected that 2 heterodimers would present unique epitopes, it is unexpected that the unique epitopes would be critical for interaction with the IL-12Rβ1 receptor chain shared by IL-12 p40 and IL-23 p40. In contrast, it would be assumed that critical IL-12 μl I-binding epitopes would be conserved between IL-12 and IL-23.

Figure 4:
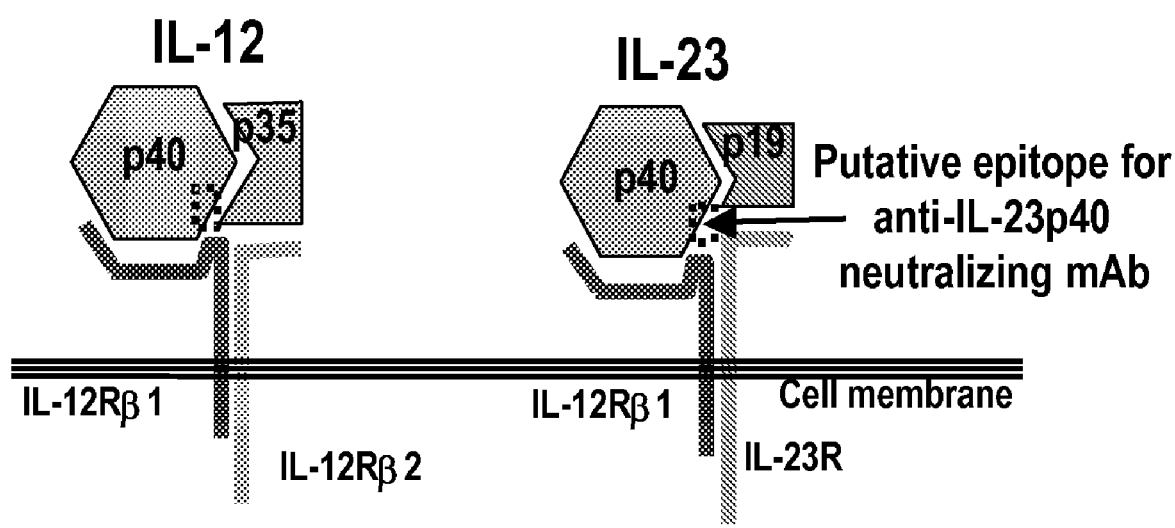
FIG. 4 illustrates an example of an IL-12RP 1 binding p40 epitope only available on IL-23.

Accordingly, the present invention identifies IL-12Rβ1-binding epitopes that are unique to IL-23 and a novel agent and mechanism for IL-23 specific neutralization that is unexpected from the present state of the art. FIG. 4 illustrates an example of an IL-12Rβ1 binding p40 epitope that would only be available on IL-23.

Two such regions are circled in FIG. 4 which shows the predicted human p40 epitopes for IL-23 specific binding. Three sequence segments within the 2 identified regions contain differences between human and murine sequences. Two sequences are located in domain 2 (D2) (amino acids 84-212 of SEQ ID NO:1) and one is located in domain 3 (D3) (amino acids 213-306 of SEQ ID NO:1) of p40; domain 1 (D1) comprises amino acids 1-83 of SEQ ID NO:1. The three potential epitope segments are underlined and labeled as Seg1, Seg2 and Seg3 in the sequence alignment between the human and murine p40 (Table 5 below). Any agent that binds these epitopes on the human or murine IL-23p40 proteins could offer specific inhibition of IL-23 bioactivity, without binding IL-12 and inhibiting IL-12.

TABLE 5

Predicted sequences for unique IL-23 p40 epitopes

IL-12/23 p40

| | | |
|---|---|---|
| hu_p40 | (1) | IWELKKDVYVVELDWYPDAPGEMVVLTCDTPEEDGITWTLDQSSEVLGSGKTLTIQVKEF |
| mu_p40 | (1) | MWELEKDVYVVEVDWTPDAPGETVNLTCDTPEEDDITWTSDQRHGVIGSGKTLTITVKEF |

| | | |
|---|---|---|
| hu_p40 | (61) | GDAGQYTCHKGGEVLSHSLLLHKKEDGIWSTDILKDQKEPKNKTFLRCEAKNYSGRFTC |
| mu_p40 | (61) | LDAGQYTCHKGGETLSHSHLLLHKKENGIWSTEILKN---FKNKTFLKCEAPNYSGRFTC |

Seg 1 spans part of this segment.

| | | |
|---|---|---|
| hu_p40 | (121) | WWLTTISTDLTFSVKSSRGSSDPQGVTCGAATLSAEKVRGDNKEYE-YSVECQEDSACPA |
| mu_p40 | (118) | SWLVQRNMBLKFNIKSSSSSPDSRAVTCGTASLSAEKVTLDQRDYEKYSVSCQEDVTCPT |

Seg 2

| | | |
|---|---|---|
| hu_p40 | (180) | AEESLPIEVMVDAVHKLKYENVTSSFFIRDIIKPKPPKNLQLKPLKNSRQVEVSWEYPDT |
| mu_p40 | (178) | AEKTLPIKLALEARQQNKYENYSTSFFIRDIIKPDPPKNLQMKPLKNS-QVEVSWEYPDS |

| | | |
|---|---|---|
| hu_p40 | (240) | WSTPHSYFSLTFCVQVQGKSK-------REKKDRVFTDKTSATVICRKNASISVRAQDR |
| mu_p40 | (237) | WSTPHSYFSLKFFVRIQRKKEKMKETEEGCNQKGALLVEKTSTEVQCKG-GNVCVQAQDR |

Seg 3

| | | |
|---|---|---|
| hu_p40 | (292) | YYSSSWSEWASVPCS |
| mu_p40 | (296) | YYNSSCSKWACVPCRVRS |

The anti-murine IL-23 p40 antibody does not bind to human IL-12, human IL-23, or human p40. Therefore, potential p40 epitopes were identified by comparing sequence and structural information for murine IL-12 versus murine IL-23, then murine IL-23 versus human IL-23.

Figure 5:
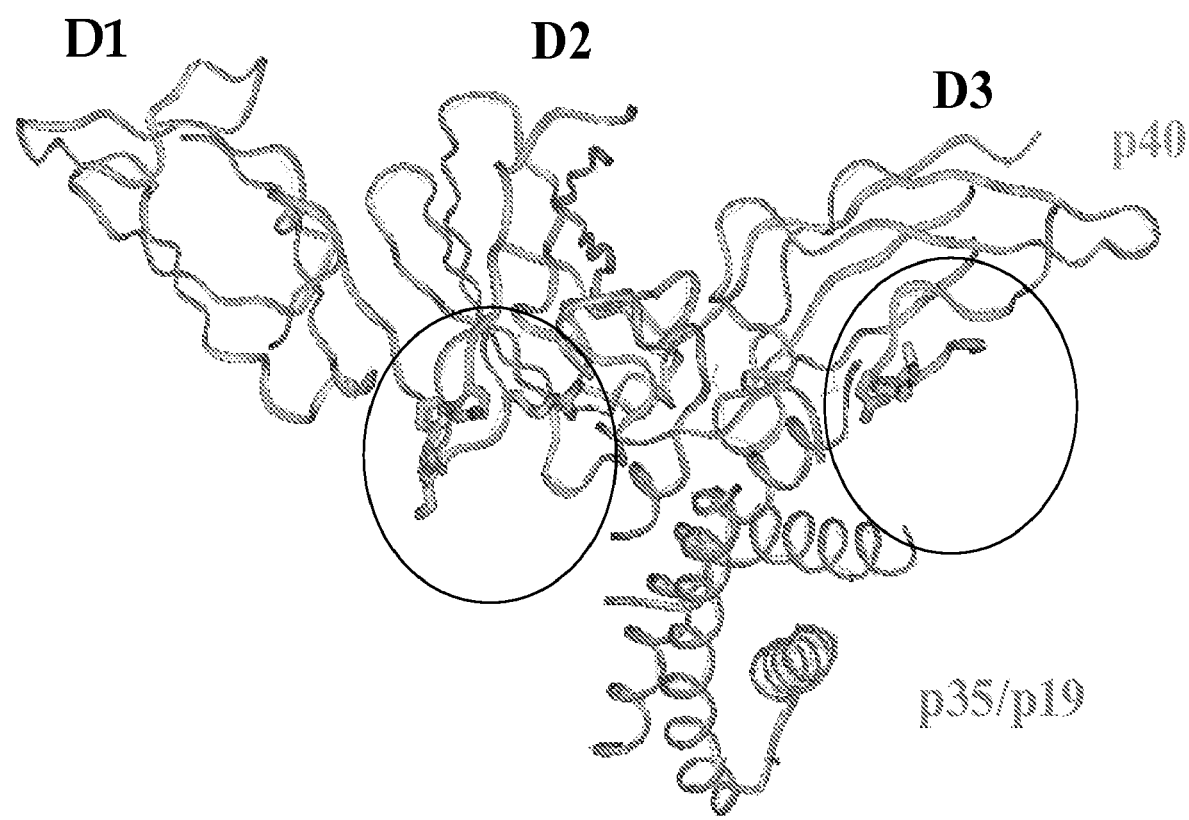
FIG. 5 shows the crystal structure of IL-12p40/p35.

The crystal structure of the human IL-12 has been reported (shown in FIG. 5). The p35 subunit is a four-helix bundle protein that is covalently linked to the p40 subunit through the inter-chain disulfide bond. It has been predicted that p19 subunit is most likely also a four-helix bundle protein. Based on sequence homology and the pattern of secondary structures of p 19 and p35, p19 should bind p40 in a similar manner. In all likelihood, the bottom portion of the structure represents both p35 (observed) and p19 (predicted). Because of the significant size differences between p35 and p19, the surface(s) on p40 that is available for antibody binding will be different between IL-12 and IL-23.

Based upon the binding data, it was hypothesized that the antibody's binding epitope must be (a) exposed on p40 surface, (b) near or covered by the p35/p19 subunits in the structures, (c) not close to the p35/p19 helices since they are most likely very similar between p 19 and p35 and would prevent antibody access, and/or (d) different between the human and murine in amino acid sequences in these regions.

This epitope information can be used to generate and/or select IL-23p40 specific binding agents. Epitope-directed mutant p40 proteins can be generated by exchanging murine and human seg1, seg2, and/or seg3 sequences into native murine or human p40 proteins. Alternatively or concurrently, individual residues of the human Seg1, Seg2, and/or Seg3 sequences can be substituted with corresponding amino acids from Murineseg1, Murineseg2, and/or Murineseg3 sequences or amino acids with similar side chain structure and/or properties to those found in the human or murine seg1, seg2, and/or seg3 sequences. For example, the following substitutions can be made:

1. human p40 with a murine seg1 sequence (residues 97-98 of murine sequence shown in Table 5, murine sequence insertion)
2. human p40 with a murine seg2 sequence (residues 135-142)
3. human p40 with a murine seg3 sequence (residues 247-274)
4. human p40 with a murine seg1 and seg2 sequence
5. human p40 with a murine seg1 and seg3 sequence
6. human p40 with a murine seg2 and seg3 sequence
7. human p40 with a murine seg1 and seg2 and seg3 sequence 8. murine p40 with a human seg1 sequence (corresponding to amino acids 97-101 of SEQ ID NO:1/sequence in Table 5), human sequence insertion)
9. murine p40 with a human seg2 sequence (residues 138-145 of SEQ ID NO:1/sequence in Table 5)
10. murine p40 with a human seg3 sequence (residues 250-269 of SEQ ID NO: 1/sequence in Table 5)
11. murine p40 with a human seg1 and seg2 sequence
12. murine p40 with a human seg1 and seg3 sequence
13. murine p40 with a human seg2 and seg3 sequence
14. murine p40 with a human seg1 and seg2 and seg3 sequence The human proteins with murine seg substitutions and the murine proteins with human seg substitutions can be used for validation and mAb generation. For example, proteins #1-7 from above can act as positive validation for Abs binding to murine IL-23. Proteins #8-14 can act as negative validation for such Abs. To validate human IL-23 binding Abs, the use of these two sets of mutants can be reversed.

The described proteins can be utilized to screen and/or select IL-23p40 specific binding agents. For example, the described proteins can be used as immunogens for hybridoma generation. Alternatively, native p40 proteins can be used as immunogens and the described proteins can be used for selection of IL-23p40 specific binding agents. Phage display libraries can be panned or screened for binding to the described proteins. Alternatively, the described proteins can be used as competitors in a native p40 binding selection process to identify IL-23p40 specific binding agents. In both cases the described proteins could be used to generate Abs either as antigens in phage display, for example, or as screening reagent for mAbs from hybridomas.

In a particular embodiment, to generate anti-human p40 (human IL-23 specific mAbs), seg1 in domain 2 can be targeted by phage display. There are several schemes that can be adopted. In one scheme, human p40 can be used to select the phage library, and use protein #1 from above (human p40 with murine Seg1) to screen the Abs, because the Abs reactive toward this epitope would not bind this chimeric protein and would only bind the wild type human p40. Abs reactive against both WT and protein #1 would not be of interest as they would not be specific for the epitope region on p40.

Protein #8 (murine p40 containing human Seg1) may also be used for screening, because only Abs binding to Seg1 containing epitope would potentially recognize this chimeric molecule assuming the chimeric protein presents an epitope containing Seg1 similar to the human p40. This is generally believed to be the case, since the structural and differences are rather small between human and mouse Abs.

In a second embodiment, protein #1 can be used as a competitor in the phage panning to remove all Abs binding human p40 except for those targeting the Seg1 containing epitopes. During screening, Abs that bind WT p40 and not protein #1 are the ones of interest and those that bind both would target other epitopes and not be specific for the epitopes identified herein (Segs. 1-3). Similar schemes can be applied to hybridoma generation and screening.

The present invention describes IL-23 specific inhibition through certain epitopes on the p40 protein. This provides a therapeutic advantage in that targeting IL-23 will provide significant benefit for immune-mediated disease. An agent that accomplishes IL-23 inhibition (binding) (i.e., prevent the bioactivity of IL-23) without binding and/or inhibiting IL-12 would suppress pathogenic biological processes and leave important IL-12 mediated pathogen immunity responses intact. In other words, primary immune responses that are dependent on IL-12 would not be affected. Whereas chronic immune responses, such as immune-mediated disease, that are dependent upon IL-23 would be inhibited. This could provide a therapeutic agent that is applicable to a broader patient population, particularly those patients with immune-mediated disease that might be at a higher risk for infection.

In addition, the biological actions of IL-12 have been associated with controlling tumor growth and eliminating tumor cells. Therefore, IL-23 specific inhibition could be a more appropriate alternative for patients with immune-mediated disease that might be at a higher risk for certain types of tumors.

The present invention provides a potency advantage as IL-12Rβ1 is thought to have a high "affinity" binding to IL-12/23p40. Therefore, inhibition of IL-23 p40 and IL-12RP 1 interaction could offer more potent therapy than agents targeted to IL-23p 19/IL-23R interaction.

Additionally, the present invention provides a cross-reactivity advantage because, if p40 can associate with alternative protein subunits other than p35 or p19, an agent that binds to the described p40 epitopes could also bind and neutralize novel p40-based cytokines.

Example 5

Mutant IL-23 Proteins

To confirm the accuracy of the epitope region on the human IL-23p40, referred to above as human seg2 (amino acids 138-145: $_{138}$RGSSDPQG$_{145}$), mutant mouse and human IL-23p40 proteins were prepared. In the human IL-23p40, the human seg2 was replaced by the murine seg2 (amino acids 135-142: $_{135}$SSSPDSRA$_{142}$) and, in the murine IL-23p40, the murine seg2 was replaced by the human seg2. The mutant and wild-type human and murine proteins were then tested for binding to the anti-human IL-23 and anti-murine IL-23 antibodies.

Materials

IL-23p40 mutants were transiently-expressed from HEK293E cells. The different mutants used in this study are listed below:

mIL-23 with hup40Seg2 swap mutant (labeled 3009):

Murine IL-23 p40 [(mu) $_{135}$SSSPDSRA$_{142}$→(hu)$_{138}$RGSSDPQG$_{145}$]

hIL-23 with mup40seg2 swap mutant (labeled 3209):

Human IL-23 p40 [(hu) $_{138}$RGSSDPQG$_{145}$→(mu)$_{135}$SSSPDSRA$_{142}$]

murine IL-23 (wild-type)

human IL-23 (wild-type)

The samples were used for binding assays.

Experimental Procedures

MSD high bind plates (Meso Scale Discovery, Gaithersburg, Md.) were coated with 5 µl of serially diluted samples, from 100 to 0 µg/ml, of different protein reagents, including human IL-23, murine IL-23 and two Seg 2-swapped mutant proteins for 2 hours at room temperature. One hundred fifty (150) µl of 5% MSD Blocker A buffer was added to each well and incubated for 1 hour at room temperature. Plates were washed three times with 0.1 M HEPES buffer, pH 7.4. These protein-charged ELISA micro-wells were incubated with 25 µl of 2 µg/mL MSD Sulfo-TAG labeled CNTO 1836 (anti murine IL-23p40 antibody) or CNTO 1275 mAb (anti-IL-112/IL-23p40 antibody). After incubation for 2 hours with shaking at room temperature, plates were washed 3 times with 0.1 M HEPES buffer (pH 7.4). MSD Read Buffer T was diluted with distilled water (4-fold) and dispensed at a volume of 150 µl/well and analyzed with a SECTOR imager 6000.

Figure 7:
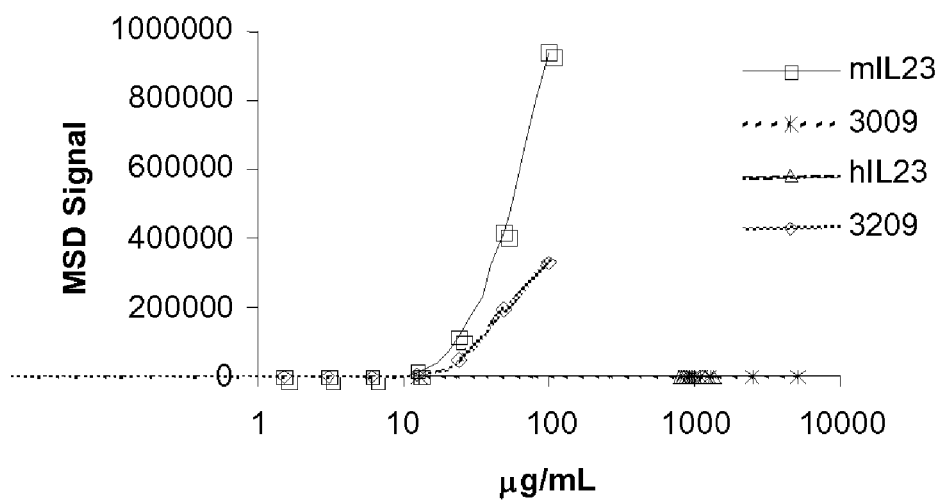
FIG. 7 shows the results of an ELISA evaluation of CNTO 1836 binding to wild-type human and murine IL-23 and mutated forms of human and murine IL-23.

Results:

Previous segment swapping work indicated that the mutated region, (murine) $_{135}$SSSPDSRA$_{142}$→(human)$_{138}$RGSSDPQG$_{145}$ located at Domain II of IL-23p40 is the binding epitope on the mouse IL-23p40 protein for CNTO 1836. To evaluate the impact of seg2 on IL-23 binding to CNTO 1836, ELISA binding assays were carried out. FIG. 7 shows the binding results of these mutant proteins for CNTO 1836. CNTO 1836 did not bind to the murine p40 with the human region corresponding to the seg2 CNTO 1836 epitope and the wild-type human IL-23. In contrast, CNTO 1836 did bind to wild-type murine IL-23 and the human p40 with the CNTO 1836 seg2 epitope transferred from mouse IL-23 protein.

Figure 8:
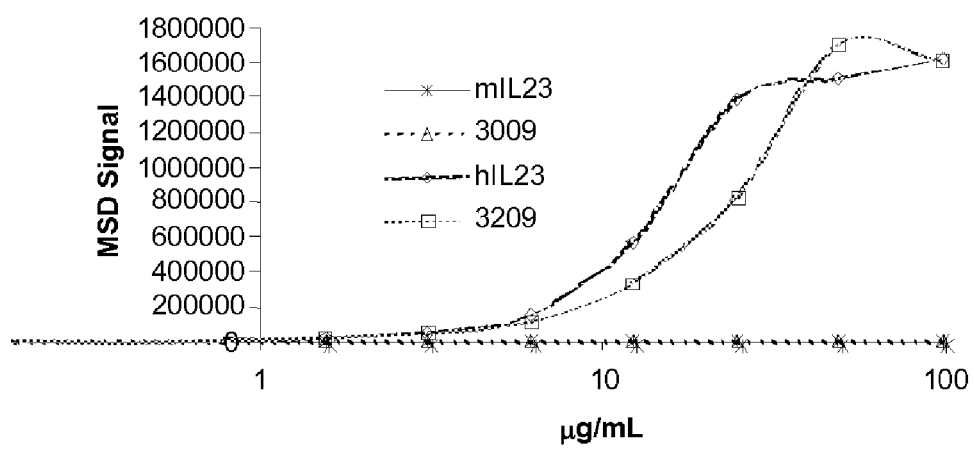
FIG. 8 shows the results of an ELISA evaluation of CNTO 1275 binding to wild-type human and murine IL-23 and mutated forms of human and murine IL-23.

Additionally, the segment-swapped and wild-type human and murine IL-23 proteins were also analyzed for their binding affinity to CNTO 1275. FIG. 8 shows that CNTO 1275 does not bind to murine wild-type IL-23 and the murine IL-23 swapped mutant (murine p40 with the human region corresponding to the CNTO 1836 epitope). In contrast, CNTO 1275 does bind to human wild-type IL-23 and the human IL-23 swapped mutant (human p40 with the murine CNTO 1836 epitope inserted in place of the IL-23p40 specific epitope). These results confirm that CNTO 1275, which binds IL-12p40 and IL-23p40 (i.e., it is not selective for IL-23p40), binds to the first domain of the p40 subunit. This finding is consistent with human seg2 being the IL-23p40-specific epitope for an antibody that only binds and neutralized IL-23p40 and does not bind and neutralize IL-12p40.

It will be clear that the invention can be practiced otherwise than as particularly described in the foregoing description and examples. Numerous modifications and variations of the present invention are possible in light of the above teachings and, therefore, are within the scope of the appended claims.

TABLE 1

EAE clinical scores with IL-12 and IL-23 neutralization initiated on day −1 (prior to Th1 differentiation).

| Group | Incidence | Mortality | Day of onset | Highest acute cs[a] | Cumul cs[b] | Cs/day | No. of relapses | Relapse severity |
|---|---|---|---|---|---|---|---|---|
| P-2001-060 | | | | | | | | |
| Rat IgG | 13/13 | 4/13 | 30.5 ± 3.2 | 3.6 ± 0.3 | 71.4 ± 14.1 | 1.2 ± 0.2 | 1.3 ± 0.2 | 3.6 ± 0.2 |
| Anti-p35 | 11/13 | 8/13 | 29.6 ± 3.4 | 3.5 ± 0.5 | 45.5 ± 11.5 | 0.8 ± 0.2 | 1.2 ± 0.1 | 4.0 ± 0.3 |
| Anti-p40 | 1/13 | 0/13 | 40.0 | 0.1 | 1.2 ± 0.5 | 0.0 ± 0.0 | 0.0 ± 0.0 | 0.0 ± 0.0 |
| P-2001-079 | | | | | | | | |
| No treatment | 6/7 | 0/7 | 24.7 ± 2.7 | 3.2 ± 0.6 | 110.4 ± 20.4 | 1.7 ± 0.3 | 1.0 ± 0.4 | 3.8 ± 0.1 |
| Rat IgG | 9/9 | 2/9 | 29.1 ± 2.9 | 3.8 ± 0.2 | 90.6 ± 10.1 | 1.5 ± 0.1 | 0.3 ± 0.2 | 4.7 ± 0.3 |
| Anti-p35 | 10/10 | 1/10 | 30.0 ± 2.6 | 3.9 ± 0.2 | 94.9 ± 17.8 | 1.4 + 0.2 | 0.7 ± 0.3 | 3.9 ± 0.2 |
| Anti-p40 | 1/10 | 0/10 | 61.0 | 0.3 | 1.6 ± 1.1 | 0.0 ± 0.0 | 0.0 + 0.0 | 0.0 + 0.0 |

[a]clinical score (cs)

[b]cumulative cs

Mice were treated as described and clinical scores were analyzed from day 0 through 70 days post EAE induction. Data is shown as the mean per group ± s.e.m.

TABLE 2

EAE clinical scores with IL-12 and IL-23 neutralization initiated on day 10 (after Th1 differentiation).

| Group | Incidence | Mortality | Day of onset | Highest acute cs[a] | Cumul cs[b] | Cs/day | # relapses | Relapse severity |
|---|---|---|---|---|---|---|---|---|
| P-2001-037 | | | | | | | | |
| No treatment | 7/8 | 0/8 | 30.6 ± 2.7 | 3.2 ± 0.5 | 51.5 ± 14.4 | 0.8 ± 0.2 | 0.3 ± 0.2 | 3.3 ± 0.8 |
| Rat IgG | 9/10 | 0/10 | 25.9 ± 2.7 | 2.7 ± 0.5 | 74.7 ± 15.8 | 1.2 ± 0.2 | 0.6 ± 0.2 | 3.7 ± 0.4 |
| Anti-p35 | 9/10 | 0/10 | 25.8 ± 2.6 | 2.5 ± 0.4 | 58.8 ± 15.6 | 1.0 ± 0.2 | 0.7 ± 0.3 | 3.2 ± 0.3 |
| Anti-p40 | 6/7 | 0/7 | 34.7 ± 6.3 | 1.6 ± 0.5 | 14.9 ± 7.5 | 0.2 ± 0.1 | 0.3 ± 0.2 | 1.5 ± 0.5 |
| P-2001-053 | | | | | | | | |
| No treatment | 8/9 | 2/9 | 15.8 ± 2.2 | 2.1 ± 0.6 | 56.4 ± 19.1 | 0.9 ± 0.3 | 0.6 ± 0.3 | 3.3 ± 0.5 |
| Rat IgG | 9/10 | 4/10 | 20.0 ± 2.5 | 3.8 ± 0.5 | 70.1 ± 17.7 | 1.3 ± 0.2 | 0.3 ± 0.2 | 4.2 ± 0.4 |
| Anti-p35 | 10/10 | 1/10 | 16.5 ± 1.1 | 3.2 ± 0.3 | 93.8 ± 15.7 | 1.4 ± 0.2 | 0.8 ± 0.2 | 3.2 ± 0.3 |
| Anti-p40 | 10/10 | 2/10 | 13.6 ± 1.1 | 2.7 ± 0.5 | 23.2 ± 7.9 | 0.4 ± 0.1 | 0.4 ± 0.3 | 2.0 ± 0.4 |

[a]clinical score (cs)

[b]cumulative cs

Mice were treated on days 10, 17, and 24 and clinical scores were analyzed from day 0 through 70 days post EAE induction. Data is shown as the mean per group ± s.e.m.

TABLE 3

EAE clinical scores with IL-12 and IL-23 neutralization initiated on day 30
(during established EAE).
From first treatment through 80 days post EAE induction

| Group | Pre-Tx[a] | Mortality | Cumul cs[b] | Cs/day | Highest cs | Lowest cs | # relapses | Relapse severity |
|---|---|---|---|---|---|---|---|---|
| P-2002-01 | | | | | | | | |
| No treatment | 2.7 ± 0.6 | 1/5 | 132.9 ± 29.3 | 3.3 ± 0.3 | 4.1 ± 0.2 | 2.4 ± 0.5 | 0.6 ± 0.4 | 3.7 ± 0.0 |
| Anti-p35 | 2.3 ± 0.7 | 1/5 | 135.9 ± 16.5 | 2.7 ± 0.3 | 3.8 ± 0.4 | 1.8 ± 0.3 | 2.0 ± 0.4 | 3.7 ± 0.3 |
| Anti-p40 | 2.0 ± 0.2 | 1/6 | 75.6 ± 16.1 | 1.9 ± 0.3 | 2.8 ± 0.5 | 1.0 ± 0.4 | 0.7 ± 0.3 | 2.5 ± 1.0 |
| P-2002-093 | | | | | | | | |
| Rat IgG | 1.7 ± 0.8 | 1/5 | 87.7 ± 16.4 | 2.1 ± 0.2 | 3.7 ± 0.4 | 1.2 ± 0.5 | 1.5 ± 0.5 | 3.8 ± 1.0 |
| Anti-p35 | 1.9 ± 0.7 | 1/5 | 98.2 ± 9.7 | 2.2 ± 0.1 | 3.7 ± 0.4 | 1.4 ± 0.4 | 1.5 ± 0.3 | 3.3 ± 0.2 |
| Anti-p40 | 2.4 ± 0.8 | 0/5 | 71.7 ± 21.6 | 1.5 ± 0.4 | 2.9 ± 0.6 | 0.8 ± 0.5 | 1.3 ± 0.3 | 2.7 ± 0.6 |

[a]mean clinical score per group on the first day of treatment (Tx)
[b]clinical score (cs)

TABLE 4

EAE clinical score analysis with IL-23 specific neutralization initiated on day 10 (after Th1 differentiation).

| Group | Incid[a] | Mort[b] | Day of Onset | Highest Acute cs | Cumul cs[c] | Cs/day[d] | No. of relapses | Relapse severity |
|---|---|---|---|---|---|---|---|---|
| Expt 1 | | | | | | | | |
| Rat IgG | 9/9 | 7/9 | 18.2 ± 0.6 | 4.7 ± 0.1 | 47.5 ± 15.6 | 1.1 ± 0.1 | 0.1 ± 0.0 | 5.0 ± 0.0 |
| Anti-IL-23 (20 mg/kg) | 9/9 | 3/9 | 28.0 ± 4.6 | 3.4 ± 0.5 | 46.1 ± 14.9 | 0.8 ± 0.2 | 0.4 ± 0.2 | 2.8 ± 0.4 |
| Anti-IL-23 (50 mg/kg) | 7/9 | 1/9 | 29.9 ± 4.6 | 2.8 ± 0.6 | 57.3 ± 16.9 | 0.9 ± 0.2 | 0.3 ± 0.2 | 3.7 ± 0.2 |
| Expt 2 | | | | | | | | |
| Anti-IL-12 | 10/10[e] | 4/10 | 24.2 ± 2.0 | 3.9 ± 0.4 | 99.9 ± 18.9 | 1.6 ± 0.3 | 0.7 ± 0.3 | 3.4 ± 0.6 |
| Anti-IL-23 (20 mg/kg) | 9/9 | 1/9 | 35.1 ± 3.1 | 2.8 ± 0.5 | 60.3 ± 16.9 | 0.9 ± 0.2 | 0.0 | 0.0 |
| Anti-IL-23 (50 mg/kg) | 6/9 | 1/9 | 30.7 ± 3.3 | 1.7 ± 0.4 | 38.1 ± 11.2 | 0.6 ± 0.2 | 0.6 ± 0.3 | 1.9 ± 0.4 |

Mice were given 3 once weekly doses of Rat IgG or anti-IL-23 starting on day 10 post EAE immunization. Clinical scores were analyzed as described in the Materials and Methods for 70 days post EAE induction. Data is shown as the mean per group ± s.e.m.
[a]Incidence,
[b]Mortality,
[c]Cumulative clinical score,
[d]Clinical score per day.

---

What is claimed is:

1. A method of selecting an anti-IL-23 antibody, comprising panning an antibody library with a variant murine p40 subunit of IL-23 and recovering the antibody binding to the variant murine p40subunit of IL-23, wherein the variant murine p40 subunit of IL-23 comprises at least one replacement from the group consisting of: (i) replacing residues 97 and 98 of the amino acid sequence of SEQ ID NO:2 with residues 97-101 of the amino acid sequence of SEQ ID NO:1, (ii) replacing residues 135-142 of the amino acid sequence of SEQ ID NO:2 with residues 138-145 of the amino acid sequence of SEQ ID NO:1, and (iii) replacing residues 247-274 of the amino acid sequence of SEQ ID NO:2 with residues 250-269 of the amino acid sequence of SEQ ID NO:1.

2. The method of claim 1, wherein the variant murine P40 subunit of IL-23 comprises a replacement of residues 135-142 of the amino acid sequence of SEQ ID NO:2 with residues 138-145 of the amino acid sequence of SEQ ID NO:1.

3. The method of claim 1, wherein the variant murine P40 subunit of IL-23 comprises a replacement of residues 97 and 98 of the amino acid sequence of SEQ ID NO:2 with residues 97-101 of the amino acid sequence of SEQ ID NO:1.

4. The method of claim 3, wherein the variant murine P40 subunit of IL-23 comprises a replacement of residues 247-274 of the amino acid sequence of SEQ ID NO:2 with residues 250-269 of the amino acid sequence of SEQ ID NO:1.

5. The method of claim 1, wherein the variant murine P40 subunit of IL-23 comprises: (i) a replacement of residues 97 and 98 of the amino acid sequence of SEQ ID NO:2 with residues 97-101 of the amino acid sequence of SEQ ID NO:1, (ii) a replacement of residues 135-142 of the amino acid sequence of SEQ ID NO:2 with residues 138-145 of the amino acid sequence of SEQ ID NO:1, and (iii) a replacement of residues 247-274 of the amino acid sequence of SEQ ID NO:2 with residues 250-269 of the amino acid sequence of SEQ ID NO:1.

6. A method of generating an anti-IL-23 antibody, comprising immunizing an animal producing antibodies with a variant murine p40 subunit of IL-23 and recovering an antibody binding to the variant murine p40 subunit of IL-23, wherein the variant murine p40 subunit of IL-23 comprises at least one replacement from the group consisting of (i) replacing residues 97 and 98 of the amino acid sequence of SEQ ID NO:2 with residues 97-101 of the amino acid sequence of SEQ ID NO:1, (ii) replacing residues 135-142 of the amino acid sequence of SEQ ID NO:2 with residues 138-145 of the amino acid sequence of SEQ ID NO:1, and (iii) replacing residues 247-274 of the amino acid sequence of SEQ ID NO:2 with residues 250-269 of the amino acid sequence of SEQ ID NO:1.

7. The method of claim 6, wherein the variant murine P40 subunit of IL-23 comprises a replacement of residues 135-142 of the amino acid sequence of SEQ ID NO:2 with residues 138-145 of the amino acid sequence of SEQ ID NO:1.

8. The method of claim 6, wherein the variant murine P40 subunit of IL-23 comprises a replacement of residues 97 and 98 of the amino acid sequence of SEQ ID NO:2 with residues 97-101 of the amino acid sequence of SEQ ID NO:1.

9. The method of claim 6, wherein the variant murine P40 subunit of IL-23 comprises a replacement of residues 247-274 of the amino acid sequence of SEQ ID NO:2 with residues 250-269 of the amino acid sequence of SEQ ID NO:1.

10. The method of claim 6, wherein the variant murine p40 subunit of IL-23 comprises: (i) a replacement of residues 97 and 98 of the amino acid sequence of SEQ ID NO:2 with residues 97-101 of the amino acid sequence of SEQ ID NO:1, (ii) a replacement of residues 135-142 of the amino acid sequence of SEQ ID NO:2 with residues 138-145 of the amino acid sequence of SEQ ID NO:1, and (iii) a replacement of residues 247-274 of the amino acid sequence of SEQ ID NO:2 with residues 250-269 of the amino acid sequence of SEQ ID NO:1.

* * * * *

SEQUENCE LISTING

```
<160> NUMBER OF SEQ ID NOS: 2

<210> SEQ ID NO 1
<211> LENGTH: 306
<212> TYPE: PRT
<213> ORGANISM: Homo sapiens

<400> SEQUENCE: 1

Ile Trp Glu Leu Lys Lys Asp Val Tyr Val Val Glu Leu Asp Trp Tyr
  1               5                  10                  15

Pro Asp Ala Pro Gly Glu Met Val Val Leu Thr Cys Asp Thr Pro Glu
             20                  25                  30

Glu Asp Gly Ile Thr Trp Thr Leu Asp Gln Ser Ser Glu Val Leu Gly
         35                  40                  45

Ser Gly Lys Thr Leu Thr Ile Gln Val Lys Glu Phe Gly Asp Ala Gly
     50                  55                  60

Gln Tyr Thr Cys His Lys Gly Gly Glu Val Leu Ser His Ser Leu Leu
```

```
                 65                  70                  75                  80
Leu Leu His Lys Lys Glu Asp Gly Ile Trp Ser Thr Asp Ile Leu Lys
                 85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
            130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
            165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
            210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
            245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
            290                 295                 300

Cys Ser
305

<210> SEQ ID NO 2
<211> LENGTH: 313
<212> TYPE: PRT
<213> ORGANISM: Mus musculus

<400> SEQUENCE: 2

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
            35                  40                  45

Ser Gly Lys Thr Leu Thr Ile Thr Val Lys Glu Phe Leu Asp Ala Gly
            50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
            115                 120                 125
```

```
                                    -continued

Phe Asn Ile Lys Ser Ser Ser Ser Pro Asp Ser Arg Ala Val Thr
    130             135             140

Cys Gly Thr Ala Ser Leu Ser Ala Glu Lys Val Thr Leu Asp Gln Arg
145             150              155                 160

Asp Tyr Glu Lys Tyr Ser Val Ser Cys Gln Glu Asp Val Thr Cys Pro
                165             170                 175

Thr Ala Glu Glu Thr Leu Pro Ile Glu Leu Ala Leu Glu Ala Arg Gln
            180             185                 190

Gln Asn Lys Tyr Glu Asn Tyr Ser Thr Ser Phe Phe Ile Arg Asp Ile
        195             200             205

Ile Lys Pro Asp Pro Pro Lys Asn Leu Gln Met Lys Pro Leu Lys Asn
    210             215             220

Ser Gln Val Glu Val Ser Trp Glu Tyr Pro Asp Ser Trp Ser Thr Pro
225             230             235                 240

His Ser Tyr Phe Ser Leu Lys Phe Phe Val Arg Ile Gln Arg Lys Lys
                245             250             255

Glu Lys Met Lys Glu Thr Glu Glu Gly Cys Asn Gln Lys Gly Ala Leu
            260             265             270

Leu Val Glu Lys Thr Ser Thr Glu Val Gln Cys Lys Gly Gly Asn Val
            275             280             285

Cys Val Gln Ala Gln Asp Arg Tyr Tyr Asn Ser Ser Cys Ser Lys Trp
    290             295             300

Ala Cys Val Pro Cys Arg Val Arg Ser
305             310
```